(12) United States Patent
Mao et al.

(10) Patent No.: US 7,153,685 B2
(45) Date of Patent: Dec. 26, 2006

(54) TAMOXIFEN AND 4-HYDROXYTAMOXIFEN-ACTIVATED SYSTEM FOR REGULATED PRODUCTION OF PROTEINS IN EUKARYOTIC CELLS

(75) Inventors: Chengjian Mao, Savoy, IL (US); David J. Shapiro, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 563 days.

(21) Appl. No.: 10/095,373

(22) Filed: Mar. 11, 2002

(65) Prior Publication Data

US 2003/0199022 A1   Oct. 23, 2003

(51) Int. Cl.
*C12N 5/00*  (2006.01)
*C12N 15/00* (2006.01)
*C07H 21/00* (2006.01)

(52) U.S. Cl. .................... 435/325; 435/320.1; 536/23.1

(58) Field of Classification Search ............... 536/23.1, 536/24.1; 435/320.1, 69.1, 325, 455; 514/44
See application file for complete search history.

(56) References Cited

U.S. PATENT DOCUMENTS

| 4,522,811 | A | 6/1985 | Eppstein et al. |
| 4,736,866 | A | 4/1988 | Leder et al. |
| 4,870,009 | A | 9/1989 | Evans et al. |
| 4,873,191 | A | 10/1989 | Wagner et al. |
| 4,987,071 | A | 1/1991 | Cech et al. |
| 5,116,742 | A | 5/1992 | Cech et al. |
| 5,328,470 | A | 7/1994 | Nabel et al. |
| 5,830,720 | A | 11/1998 | Bock et al. |
| 6,133,027 | A | 10/2000 | Yee et al. |
| 6,455,300 | B1 * | 9/2002 | Htun et al. ............... 435/252.3 |

FOREIGN PATENT DOCUMENTS

| WO | WO 89/10134 A1 | 11/1989 |
| WO | WO 90/11354 A1 | 10/1990 |
| WO | WO 91/01140 A1 | 2/1991 |
| WO | WO 93/04169 A1 | 3/1993 |

OTHER PUBLICATIONS

Predki et al., Biochem J, 305, 805-810, 1995.*
Gene (1989), vol. 83. No. 1, pp. 137-146 (ABSTRACT only currently available).*
Zhao et al. GenBank Accession No. BH053030, available Jul. 17, 2001.*
Ali, S., et al., "Modulation of transcriptional activation by ligand-dependent phosphorylation of the human oestrogen receptor A/B region," *EMBO Journal*, 12(3):1153-1160 (1993).
Austin, C. and C. Cepko, "Cellular migration patterns in the developing mouse cerebral cortex," *Development*, 110:713-732 (1990).

Baim, S., et al., "A Chimeric Mammalian Transactivator Based on the lac Repressor that is Regulated by Temperature and Isopropyl β-D-Thiogalactopyranoside," *Proc. Natl. Acad. Sci. USA*, 88(12):5072-5076 (1991).
Barkhem, T., et al., "Characterization of the "Estrogenicity" of Tamoxifen and Raloxifene in HepG2 Cells: Regulation of Gene Expression from an ERE Controlled Reporter Vector Versus Regulation of the Endogenous SHBG and PS2 Genes," *J. Steroid Biochem. Molec. Biol.*, 62(1):53-64 (1997).
Bartel, D. and J. Szostak, "Isolation of New Ribozymes from a Large Pool of Random Sequences," *Science*, 261(5127):1411-1418 (1993).
Bechtold, N. and G. Pelletier, "In Planta Agrobacterium-Mediated Transformation of Adult *Arabidopsis thaliana* Plants by Vacuum Infiltration," *Meth. Mol. Biol.*, 82:259-266 (1998).
Becker, D.M. and L. Guarente, "High-Efficiency Transformation of Yeast by Electroporation," *Meth. In Enzymology*, 194:182-187 (1991).
Beggs, J.D., "Transformation of yeast by a replicating hybrid plasmid," *Nature*, 275:104-109 (1978).
Belshaw, P., et al., "Controlling Protein Association and Subcellular Localization with a Synthetic Ligand that Induces Heterodimerization of Proteins," *Proc. Natl. Acad. Sci. USA*, 93(10):4604-4607 (1996).
Biowire.com, "Inducible Mammalian Expression System with pIND," Sep. 27, 2001.
Bodine, et al., "Survival and Retrovirus Infection of Murine Hematopoietic Stem Cells in vitro: Effects of 5-FU and Method of Infection," *Exp. Hematol.*, 19:206-212, (1991).
Boorsma, M., et al., "A temperature-regulated replicon-based DNA expression system," *Nat. Biotechnol.*, 18:429-432 (2000).
Bradley, A., "Modifying the mammalian genome by gene targeting," *Curr. Opin. Biotechnol.*, 2:823-829, (1991).
Braselmann, S., et al., "A selective transcriptional induction system for mammalian cells based on Ga14-estrogen receptor fusion proteins," *Proc. Natl. Acad. Sci. USA*, 90:1657-1661 (1993).
Capecchi, M., "High Efficiency Transformation by Direct Microinjection of DNA into Cultured Mammalian Cells," *Cell*, 22:479-488 (1980).
Carter, P., "Site-directed mutagenesis," *Biochem. J.*, 237:1-7 (1986).
Cepko, C., et al., "Construction and Applications of a Highly Transmissible Murine Retrovirus Shuttle Vector," *Cell*, 37:1053-1062 (1984).
Chaney, W.G., et al., "High-Efficiency Transfection of CHO Cells Using Polybrene," *Somatic Cell and Mol. Genetics*, 12(3):237-244 (1986).
Chen, C.A. and H. Okayama, "Calcium Phosphate-Mediated Gene Transfer: A Highly Efficient Transfection System for Stably Transforming Cells with Plasmid DNA," *BioTechniques*, 6(7):632-638 (1988).

(Continued)

*Primary Examiner*—Janet L Epps-Ford
(74) *Attorney, Agent, or Firm*—Evan Law Group LLC

(57) ABSTRACT

Novel tamoxifen inducible and ICI 182,780 repressible expression systems comprising mutant estrogen receptors and mutant estrogen response element are disclosed. Such systems have a wide variety of applications, including gene therapy and in vivo and in vitro expression, as well as their use in transgenic animals.

30 Claims, 14 Drawing Sheets

OTHER PUBLICATIONS

Chen, S., et al., "Gene Therapy for Brain Tumors: Regression of Experimental Gliomas by Adenovirus-Mediated Gene Transfer in vivo," *Proc. Natl. Acad. Sci. USA*, 91(8):3054-3057 (1994).

Chusacultanachai, S., et al., "Analysis of Estrogen Response Element Binding by Genetically Selected Steroid Receptor DNA Binding Domain Mutants Exhibiting Altered Specificity and Enhanced Affinity," *J. Biol. Chem.*, 274(33):23591-23598 (1999).

Cohen, S., et al., "Nonchromosomal Antibiotic Resistance in Bacteria: Genetic Transformation of *Escherichia coli* by R-Factor DNA," *Proc. Natl. Acad. Sci. USA*, 69(8):2110-2114 (1972).

Danielian, P.S., et al., "Identification of a conserved region required for hormone dependent transcriptional activation by steroid hormone receptors," *EMBO J.*, 11(3):1025-1033 (1992).

David, M., "Transcription Factors in Interferon Signaling," *Pharmac. The.*, 65:149-161 (1995).

De Haan, G., et al., "Estrogen Receptor-KRAB Chimeras Are Potent Ligand-dependent Repressors of Estrogen-regulated Gene Expression," *J. Biol. Chem.*, 275(18):13493-13501 (2000).

Deuschle, U., et al., "RNA Polymerase II Transcription Blocked by *Escherichia coli* Lac Repressor," *Science*, 248(4954):480-483 (1990).

Doly, J., et al., "Type I interferons: expression and signalization," *CMLS Cell. Mol. Life Sci.*, 54:1109-1121 (1998).

Elroy-Stein, O. and B. Moss, "Cytoplasmic Expression System Based on Constitutive Synthesis of Bacteriophage T7 RNA Polymerase in Mammalian Cells," *Proc. Natl. Acad. Sci. USA*, 87(17):6743-6747 (1990).

Escudero, J. and B. Hohn, "Transfer and Integration of T-DNA without Cell Injury in the Host Plant," *The Plant Cell*, 9:2135-2142 (1997).

Fekete, D. and C. Cepko, "Retroviral Infection Coupled with Tissue Transplantation Limits Gene Transfer in the Chicken Embryo," *Proc. Natl. Acad. Sci. USA*, 90(6):2350-2354 (1993).

Felgner, P., et al., "Lipofection: A Highly Efficient, Lipid-Mediated DNA-Transfection Procedure," *Proc. Natl. Acad. Sci. USA*, 84(21):7413-7417 (1987).

Filmus, J., et al., "Synergistic induction of promoters containing metal- and glucocorticoid-responsive elements," *Nucleic Acids Res.*, 20(11);2755-2760 (1992).

Finer, J.J., et al., "Particle Bombardment Mediated Transformation," *Curr. Topics in Microbiology And Immunology*, vol. 240, pp. 60-80 (1999).

Fromm, M., et al., "Expression of Genes Transferred into Monocot and Dicot Plant Cells by Electroporation," *Proc. Natl. Acad. Sci. USA*, 82(17):5824-5828 (1985).

Fuhrmann-Benzakein, E., et al., "Inducible and irreversible control of gene expression using a single transgene," *Nucleic Acids Res.*, 28(23):1-5, e99 (2000).

Fujita, T., et al., "Regulation of Human Interleukin-2 Gene: Functional DNA Sequences in the 5' Flanking Region for the Gene Expression in Activated T Lymphocytes," *Cell*, 46:401-407 (1986).

Gautier, C., et al., "α-DNA IV: α-anomeric and β-anomeric tetrahymidylates covalently linked to intercalating oxazolopyridocarbazole. Synthesis, physiochemical properties and poly (rA) binding," *Nucleic Acids Res.*, 15(16):6625-6641 (1987).

Gietz, et al. "Growth & Transformation of s. cerevicae," *in* "Cells: A Laboratory Manual," vol. I, pp. 21.1-21.22 . D. Spector, R. Goldman and L. Leinwand, eds. Cold Spring Harbor Press, Cold Spring Harbor, NY, (1998).

Gingrich, J. and J. Roder, "Inducible Gene Expression in the Nervous System of Transgenic Mice," *Annu. Rev. Neurosci.*, 21:377-405 (1998).

Gossen, M. and H. Bujard, "Tight control of gene expression in mammalian cells by tetracycline-responsive promoters," *Proc. Natl. Acad. Sci. USA*, 89:5547-5551 (1992).

Gossen, M., et al., "Transcriptional Activation by Tetracyclines in Mammalian Cells," *Science*, 268:1766-1769 (1995).

Graham, F.L. and A.J. van der Eb, "A New Technique for the Assay of Infectivity of Human Adenovirus 5 DNA," *Virology*, 52:456-467 (1973).

Hanahan, D., "Studies on Transformation of *Eschirichia coli* with Plasmids," *J. Mol. Biol.*, 166:557-580 (1983).

Hansen, G. and M.D. Chilton, "Lessons in Gene Transfer to Plants by a Gifted Microbe," *Novartis Agribus. Biotechnol. Res.*, pp. 22-57 (1999) *in Current Topics in Microbiology and Immunology*, 240:21-57 (1999).

Hansen, G. and M. Wright, "Recent advances in the transformation of plants," *Trends in Plant Science*, 4(6):226-231 (1999).

Haseloff, J. and W. Gerlach, "Simple RNA enzymes with new and highly specific endoribonuclease activities," *Nature*, 334:585-591 (1988).

Hinnen, A., et al., "Transformation of Yeast," *Proc. Natl. Acad. Sci. USA*, 75(4):1929-1933 (1978).

Hoffmann, F., "Laser microbeams for the manipulation of plant cells and subcellular structures," *Plant Science*, 113:1-11 (1996).

Htun, H., et al., "Direct Visualization of the Human Estrogen Receptor α Reveals a Role for Ligand in the Nuclear Distribution of the Receptor," *Mol. Biol. Cell*, 10:471-486 (1999).

Hyrup, B. and P. Nielsen, "Peptide Nucleic Acids (PNA): Synthesis, Properties and Potential Applications," *Bioorganic & Med. Chem.*, 4(1):5-23 (1996).

Indra, A., et al., "Temporally-controlled site-specific mutagenesis in the basal layer of the epidermis: comparison of the recombinase activity of the tamoxifen-inducible Cre-ER$^T$ and CRE-ER$^{T2}$ recombinases," *Nuc. Acids Res.*, 27(22):4324-4327 (1999).

Inoue, H., et al., "Sequence-dependent hydrolysis of RNA using modified oligonucleotide splints and RNase H," *FEBS Letters*, 215(2);327-330 (1987).

Inoue, H., et al., "Synthesis and hybridization studies on two complementary nona(2'-O-methyl)ribonucleotides," *Nucl. Acids Res.*, 15(15):6131-6148 (1987).

Ishiura, M., et al., "Phage Particle-Mediated Gene Transfer to Cultured Mammalian Cells," *Mol. Cell. Biol.*, 2(6):607-616 (1982).

Ito, H., et al., "Transformation of Intact Yeast Cells Treated with Alkali Cations," *J. Bacteriol.*, 153(1):163-168 (1983).

Kato, S., et al., "Activation of the Estrogen Receptor Through Phosphorylation by Mitogen-Activated Protein Kinase," *Science*, 270(5241):1491-1494 (1995).

Kaufman, R., et al., "Selection and Amplification of Heterologous Genes Encoding Adenosine Deaminase in Mammalian Cells," *Proc. Natl. Acad. Sci. USA*, 83(10):3136-3140 (1986).

Kawai, S. and M. Nishizawa, "New Procedure for DNA Transfection with Polycation and Dimethyl Sulfoxide," *Mol. Cell. Biol.*, 4(6):1172-1174 (1984).

Kothary, R., et al., "Inducible expression of an hsp68-lacZ hybrid gene in transgenic mice," *Development*, 105:707-714 (1989).

Kuhn, R., et al., "Inducible Gene Targeting in Mice," *Science*, 269(5229):1427-1429 (1995).

Kuo, W., et al., "Inducible Expression and Cellular Localization of Insulin-degrading Enzyme in a Stably Transfected Cell Line," *J. Biol. Chem.*, 269(36):22599-22606 (1994).

Labow, M., et al., "Conversion of the *lac* Repressor into an Allosterically Regulated Transcriptional Activator for Mammalian Cells," *Mol. And Cell. Biology*, 10(7):3343-3356 (1990).

Lakso, M., et al., "Targeted Oncogene Activation by Site-Specific Recombination in Transgenic Mice," *Proc. Natl. Acad. Sci.*, 89(14)6232-6236 (1992).

Leduc, N., et al., "Isolated Maize Zygotes Mimic *in Vivo* Embryonic Development and Express Microinjected Genes When Cultured *in Vitro*," *Develop. Biol.*, 177:190-203 (1996).

Lemaitre, M., et al., "Specific Antiviral Activity of a Poly(L-lysine)-Conjugated Oligodeoxyribonucleotide Sequence Complementary to Vesicular Stomatitis Virus N Protein mRNA Initiation Site," *Proc. Natl. Acad. Sci. USA*, 84(3):648-652 (1987).

Lemischka, I., et al., "Developmental Potential and Dynamic Behavior of Hematopoietic Stem Cells," *Cell*, 45:917-927 (1986).

Letsinger, R., et al., "Cholesteryl-Conjugated Oligonucleotides: Synthesis, Properties, and Activity as Inhibitors of Replication of Human Immunodeficiency Virus in Cell Culture," *Proc. Natl. Acad. Sci. USA*, 86(17):6553-6556 (1989).

Levenson, A., et al., "Estrogenic Activity is Increased for an Antiestrogen by a Natural Mutation of the Estrogen Receptor," *J. Steroid Biochem. Molec. Biol.*, 60(5-6):261-268 (1997).

Levenson, A.S. and V.C. Jordan, "The Key to the Antiestrogenic Mechanism of Raloxifene Is Amino Acid 351 (Aspartate) in the Estrogen Receptor1," *Cancer Res.*, 58:1872-1875 (1998).

Li, E., et al., "Targeted Mutation of the DNA Methyltransferase Gene Results in Embryonic Lethality," *Cell*, 69:915-926 (1992).

Littlefield, J., "Selection of Hybrids from Matings of Fibroblasts in vitro and Their Presumed Recombinants," *Science*, 145(3633):709-710 (1964).

Lopata, M.A., et al., "High level transient expression of a chloramphenicol acetyl transferase gene by DEAE-dextran mediated DNA transfection coupled with a dimethyl sulfoxide or glycerol shock treatment," *Nucl. Acids Res.*, 12(14):5707-5717 (1984).

Luckow, V., "Cloning and Expression of Heterologous Genes in Insect Cells with Baculovirus Vectors," *In* Recomb. DNA Technol. & Appl., 97-152, (1991).

Maher III, L.J., "DNA Triple-Helix Formation: An Approach to Artificial Gene Repressors?," *BioEssays*, 14(12):807-815 (1992).

Mandel, M. and A. Higa, "Calcium-dependent Bacteriophage DNA Infection," *J. Mol. Biol.*, 53:159-162 (1970).

Martin, M., et al., "A Role for Akt in Mediating the Estrogenic Functions of Epidermal Growth Factor and Insulin-Like Growth Factor I," *Endocrinology*, 141(12):4503-4511 (2000).

Martinez, E. and W. Wahli, "Cooperative binding of estrogen receptor to imperfect estrogen-responsive DNA elements correlates with their synergistic hormone-dependent enhancer activity," *EMBO J.*, 8(12):3781-3791 (1989).

Mattick, S., et al., "Analysis of Ligand Dependence and Hormone Response Element Synergy in Transcription by Estrogen Receptor," *J. Steroid Biochem. Molec. Biol.*, 60(5-6):285-294 (1997).

McInerney, E. and B. Katzenellenbogen, "Different Regions in Activation Function-1 of the Human Estrogen Receptor Required for Antiestrogen- and Estradiol-dependent Transcription Activation," *J. Biol. Chem.*, 271(39):24172-24178 (1996).

Miller, A.D. and C. Buttimore, "Redesign of Retrovirus Packaging Cell Lines To Avoid Recombination Leading to Helper Virus Production," *Mol. Cell. Biology*, 6(8):2895-2902 (1986).

Miller, L.K., "Baculoviruses As Gene Expression Vectors," *Ann. Rev. Microbiol.*, 42:177-199 (1988).

Neumann, F., et al., "Gene transfer into mouse lyoma cells by electroporation in high electric fields," *EMBO J.*, 1(7):841-845 (1982).

No, D., et al., "Ecdysone-inducible gene expression in mammalian cells and transgenic mice," *Proc. Natl. Acad. Sci. USA*, 93:3346-3351 (1996).

Nunez,A-M, et al., "The 5' flanking region of the pS2 gene contains a complex enhancer region responsive to oestrogens, epidermal growth factor, a tumour promoter (TPA), the c-Ha-ras oncoprotein and the c-jun protein," *EMBO J.*, 8(3):823-829 (1989).

O'Brien, K., et al., "Construction and characterization of a one-plasmid system for the controlled expression of genes in mammalian cells by tetracycline," *Gene*, 184:115-120 (1997).

O'Gorman, S., et al., "Recombinase-Mediated Gene Activation and Site-Specific Integration in Mammalian Cells," *Science*, 251(4999):1351-1355 (1991).

Ou-Lee, T., et al., "Expression of a Foreign Gene Linked to Either a Plant-Virus or a Drosophila Promoter, after Electroporation of Protoplasts of Rice, Wheat, and Sorghum," *Proc. Natl. Acad. Sci. USA*, 83(18):6815-6819 (1986).

Palmer, T., et al., "Efficient Retrovirus-Mediated Transfer and Expression of a Human Adenosine Deaminase Gene in Diploid Skin Fibroblasts from an Adenosine Deaminase-Deficient Human," *Proc. Natl. Acad. Sci. USA*, 84(4):1055-1059 (1987).

Pear, W., et al., "Production of High-Titer Helper-Free Retroviruses by Transient Transfection," *Proc. Natl. Acad. Sci. USA*, 90(18):8392-8396 (1993).

Perry-O'Keefe, H., et al., "Peptide Nucleic Acid Pre-Gel Hybridization: An Alternative to Southern Hybridization," *Proc. Natl. Acad. Sci. USA*, 93(25):14670-14675 (1996).

Peyrade, F., et al. "Age-related difference in tamoxifen disposition," *Clin. Pharmacol. & Therap.* 59:401-410 (1996).

Ponglikitmongkol, M., et al., "Synergistic activation of transcription by the human estrogen receptor bound to tandem responsive elements," *EMBO J.*, 9(7):2221-2231 (1990).

Potter, H., et al., "Enhancer-Dependent Expression of Human κ-Immunoglobulin Genes Introduced into Mouse pre-B Lymphocytes by Electroporation," *Proc. Natl. Acad. Sci. USA*, 81(22):7161-7165 (1984).

Potter, H., "Electroporation in Biology: Methods, Applications, and Instrumentation," *Anal. Biochem.*, 174:361-373 (1988).

Rassoulzadegan, M., et al., "High frequencey of gene transfer after fusion between bacteria and eukaryotic cells," *Nature*, 295:257-259 (1982).

Rhodes, C., et al., "Genetically Transformed Maize Plants from Protoplasts," *Science*, 240(4849):204-207 (1988).

Rose, J.K., et al., "A New Cationic Liposome Reagent Mediating Nearly Quantitative Transfection of Animal Cells," *BioTechniques*, 10(4):520-525 (1991).

Sadowski, I., et al., "GAL4-VP16 is an unusually potent transcriptional activator," *Nature*, 335:563-564 (1988).

Sandri-Goldin, R., et al., "High-Frequency Transfer of Cloned Herpes Simplex Virus Type 1 Sequences to Mammalian Cells by Protoplast Fusion," *Mol. Cell. Biol.*, 1(8):743-752 (1981).

Saunders, J., et al., "Plant Gene Transfer Using Electrofusion and Electroporation." , *In Electroporate & Electrofusion Biol.*, ch. 22, pp. 343-354 (1989).

Schaffner, W., "Direct Transfer of Cloned Genes from Bacteria to Mammalian Cells," *Proc. Natl. Acad. Sci. USA*, 77(4):2163-2167 (1980).

Schweinfest, C., et al., "A heat-shock-inducible eukaryotic expression vector," *Gene*, 71:207-210 (1988).

Selden, R., et al., "Human Growth Hormone as a Reporter Gene in Regulation Studies Employing Transient Gene Expression," *Mol. Cell. Biol.*, 6(9):3173-3179 (1986).

Shang, Y., et al., "Cofactor Dynamics and Sufficiency in Estrogen Receptor-Regulated Transcription," *Cell*, 103:843-852 (2000).

Shiau, A., et al., "The Structural Basis of Estrogen Receptor/Coactivator Recognition and the Antagonism of This Interaction by Tamoxifen," *Cell*, 95:927-937 (1998).

Shigekawa, K. and W. Dower, "Electroporation of Eukaryotes and Prokaryotes: A General Approach to the Introduction of Macromolecules into Cells," *BioTechniques*, 6(8):742-751 (1988).

Shillito, R., "Methods of genetic transformations: Electroporation and Polyethylene Glycol Treatment," *In Molecular Improvement of Cereal Crop*, pp. 9-20 (1999).

Shockett, P., et al., "A modified tetracycline-regulated system provides autoregulatory, inducible gene expression in cultured cells and transgenic mice," *Proc. Natl. Acad. Sci. USA*, 92:6522-6526 (1995).

Simonsen, C. and A. Levinson, "Isolation and Expression of an Altered Mouse Dihydrofolate Reductase cDNA," *Proc. Natl. Acad. Sci. USA*, 80(9):2495-2499 (1983).

Somia, N., et al., "Piecing together more efficient gene expression," *Nat. Biotechnol.*, 17:224-225 (1999).

Southern, P.J. and P. Berg, "Transformation of Mammalian Cells to Antibiotic Resistance with a Bacterial Gene Under Control of the SV40 Early Region Promoter," *J. Mol. Appl. Genetics*, 1:327-341 (1982).

Spencer, D., et al., "Controlling Signal Transduction with Synthetic Ligands," *Science*, 262(5136):1019-1024 (1993).

Stein, C. and J. Cohen, "Oligodeoxynucleotides as Inhibitors of Gene Expression: A Review," *Cancer Res.*, 48:2659-2668 (1998).

Stratagene.com, "Complete Control® Inducible Mammalian Expression System," Sep. 27, 2001.

Stratagene.com, "LacSwitch® II Inducible Mammalian Expression System," Sep. 27, 2001.

Thomas, K. and M. Capecchi, "Site-Directed Mutagenesis by Gene Targeting in Mouse Embryo-Derived Stem Cells," *Cell*, 51:503-512 (1987).

Thompson, J.A., et al., "Maize transformation utilizing silicon carbide whiskers: a review," *Euphytica*, 85:75-80 (1995).

Touraev, A., et al., "Plant male germ line transformation," *The Plant Journal*, 12(4):949-956 (1997).

Trick, H., R. Dinkins, E. Santarem, R. Di, et al., "Recent advances in soybean transformation," *Plant Tissue Cult. Bitechnol.*, 3:9-26, (1997).

Triezenberg, S., et al., "Functional dissection of VP16, the transactivator of herpes simplex virus immediate early gene expression," *Genes & Devel.*, 2:718-729 (1988).

Turner, D., et al., "Lineage-Independent Determination of Cell Type in the Embryonic Mouse Retina," *Neuron*, 4:833-845 (1990).

van der Krol, A., et al., "Modulation of Eukaryotic Gene Expression by Complementary RNA or DNA Sequences," *BioTechniques*, 6(10):958-976 (1988).

Wang, Y., et al., "A regulatory system for use in gene transfer," *Proc. Natl. Acad. Sci. USA*, 91:8180-8184 (1994).

Wang, Y., et al., "Ligand-inducible and liver-specific target gene expression in transgenic mice," *Nat. Biotechnol.*, 15:239-243 (1997).

Webb, P., et al., "Tamoxifen Activation of the Estrogen Receptor/AP-1 Pathway: Potential Origin for the Cell-Specific Estrogen-Like Effects of Antiestrogens," *Mol. Endocrinol.*, 9(4):443-456 (1995).

Webb, P., et al., "An Antiestrogen-responsive Estrogen Receptor-α Mutant (D351Y) Shows Weak AF-2 Activity in the Presence of Tamoxifen," *J. Biol. Chem.*, 275(48):37552-37558 (2000).

Wells, J., et al., "Cassette mutagenesis: an efficient method for generation of multiple mutations at defined sites," *Gene*, 34:315-323 (1985).

Whitt, M., et al., "TransfectACE™ Reagent: Transient Transfection Frequencies > 90%," *Focus*, 13:8-12, (1990).

Wigler, M., et al., "Biochemical Transfer of Single-Copy Eucaryotic Genes Using Total Cellular DNA as Donor," *Cell*, 14:725-731 (1978).

Williams, D., et al., "Introduction of new genetic material into pluripotent haematopoietic stem cells of the mouse," *Nature*, 310:476-480 (1984).

Wilmut, I., et al., "Viable offspring derived from fetal and adult mammalian cells," *Nature*, 385:810-813 (1997).

Wong, T-K and E. Neumann, "Electric Field Mediated Gene Transfer," *Biochem. Biophys. Res. Comm.*, 107(2):584-587 (1982).

Zhang, C., et al., "HMG-1 Stimulates Estrogen Response Element Binding by Estrogen Receptor from Stably Transfected HeLa Cells," *Mol. Endocrinol.*, 13:632-643 (1999).

Zhang, Y., et al., "Inducible site-directed recombination in mouse embryonic stem cells," *Nuc. Acids Res.*, 24(4):543-548 (1996).

Zhou, G-Y, et al., "Introduction opf Exogenous DNA into Cotton Embryos," *Meth. Enzymol.*, 101:433-481 (1983).

Zoller, M. and M. Smith, "Oligonucleotide-Directed Mutagenesis: A Simple Method using Two Oligonucleotide Primers and a Single-Stranded DNA Template," *Methods Enzymol.*, 154:329-350 (1987).

Zon, G., "Oligonucleotide Analogues as Potential Chemotherapeutic Agents," *Pharmaceut. Res.*, 5(9):539-549 (1988).

Zuo, J. and N. Chua, "Chemical-inducible systems for regulated expression of plant genes," *Curr. Opin. Biotechnol.*, 11:146-151 (2000).

* cited by examiner

ATL8/PAL-N-79:

ATL8/PAL-LUC:

SEQUENCE LISTING

<160> NUMBER OF SEQ ID NOS: 83

<210> SEQ ID NO 1
<211> LENGTH: 1785
<212> TYPE: DNA
<213> ORGANISM: Homo sapiens

<400> SEQUENCE: 1

| | | | | | |
|---|---|---|---|---|---|
| atgaccatga | ccctccacac | caaagcatct | gggatggccc | tactgcatca | gatccaaggg | 60 |
| aacgagctgg | agcccctgaa | ccgtccgcag | ctcaagatcc | cctggagcg | gcccctgggc | 120 |
| gaggtgtacc | tggacagcag | caagcccgcc | gtgtacaact | accccgaggg | cgccgcctac | 180 |
| gagttcaacg | ccgcggccgc | cgccaacgcg | caggtctacg | gtcagaccgg | cctcccctac | 240 |
| ggccccgggt | ctgaggctgc | ggcgttcggc | tccaacggcc | tggggggttt | cccccactc | 300 |
| aacagcgtgt | ctccgagccc | gctgatgcta | ctgcacccgc | cgccgcagct | gtcgccttc | 360 |
| ctgcagcccc | acggccagca | ggtgccctac | tacctggaga | cgagcccag | cggctacacg | 420 |
| gtgcgcgagg | ccggcccgcc | ggcattctac | aggccaaatt | cagataatcg | acgccagggt | 480 |
| ggcagagaaa | gattggccag | taccaatgac | aagggaagta | tggctatgga | atctgccaag | 540 |
| gagactcgct | actgtgcagt | gtgcaatgac | tatgcttcag | gctaccatta | tggagtctgg | 600 |
| tcctgtgagg | gctgcaaggc | cttcttcaag | agaagtattc | aaggacataa | cgactatatg | 660 |
| tgtccagcca | ccaaccagtg | caccattgat | aaaaacagga | ggaagagctg | ccaggcctgc | 720 |
| cggctccgca | aatgctacga | agtgggaatg | atgaaaggtg | ggatacgaaa | agaccgaaga | 780 |
| ggagggagaa | tgttgaaaca | caagcgccag | agagatgatg | gggagggcag | gggtgaagtg | 840 |
| gggtctgctg | gagacatgag | agctgccaac | ctttggccaa | gcccgctcat | gatcaaacgc | 900 |
| tctaagaaga | acagcctggc | cttgtccctg | acggccgacc | agatggtcag | tgccttgttg | 960 |
| gatgctgagc | ccccatact | ctattccgag | tatgatccta | ccagaccctt | cagtgaagct | 1020 |
| tcgatgatgg | gcttactgac | caacctggca | gacagggagc | tggttcacat | gatcaactgg | 1080 |
| gcgaagaggg | tgccaggctt | tgtggatttg | accctccatg | atcaggtcca | ccttctagaa | 1140 |
| tgtgcctggc | tagagatcct | gatgattggt | ctcgtctggc | gctccatgga | gcacccagtg | 1200 |
| aagctactgt | ttgctcctaa | cttgctcttg | gacaggaacc | agggaaaatg | tgtagagggc | 1260 |
| atggtggaga | tcttcgacat | gctgctggct | acatcatctc | ggttccgcat | gatgaatctg | 1320 |
| cagggagagg | agtttgtgtg | cctcaaatct | attattttgc | ttaattctgg | agtgtacaca | 1380 |
| tttctgtcca | gcaccctgaa | gtctctggaa | gagaaggacc | atatccaccg | agtcctggac | 1440 |
| aagatcacag | acactttgat | ccacctgatg | gccaaggcag | gcctgaccct | gcagcagcag | 1500 |
| caccagcggc | tgggcccagct | cctcctcatc | ctctcccaca | tcaggcacat | gagtaacaaa | 1560 |
| ggcatggagc | atctgtacag | catgaagtgc | aagaacgtgg | tgcccctcta | tgacctgctg | 1620 |
| ctggagatgc | tggacgccca | ccgcctacat | gcgcccacta | gccgtggagg | ggcatccgtg | 1680 |
| gaggagacgg | accaaagcca | cttggccact | gcgggctcta | cttcatcgca | ttccttgcaa | 1740 | aagtattaca tcacggggga ggcagagggt ttccctgcca cagtc     1785

<210> SEQ ID NO 2
<211> LENGTH: 595
<212> TYPE: PRT
<213> ORGANISM: Homo sapiens

<400> SEQUENCE: 2

```
Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
             20                  25                  30

Ile Pro Leu Glu Arg Pro Leu Gly Glu Val Tyr Leu Asp Ser Ser Lys
         35                  40                  45

Pro Ala Val Tyr Asn Tyr Pro Glu Gly Ala Ala Tyr Glu Phe Asn Ala
     50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Ala Phe Gly Ser Asn Gly Leu Gly Gly
                 85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365
```

```
Asp Leu Thr Leu His Asp Gln Val His Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
    515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
    580                 585                 590

Ala Thr Val
    595

<210> SEQ ID NO 3
<211> LENGTH: 48
<212> TYPE: DNA
<213> ORGANISM: Artificial Sequence
<220> FEATURE:
<223> OTHER INFORMATION: Mutant DBD of ER

<400> SEQUENCE: 3
tggggctgca aggccttctt caagagatct attgcaggag gtaacgac          48

<210> SEQ ID NO 4
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 4

Trp Gly Cys Lys Ala Phe Phe Lys Arg Ser Ile Ala Gly Gly Asn Asp
1               5                   10                  15

Tyr

<210> SEQ ID NO 5
<211> LENGTH: 48
<212> TYPE: DNA
<213> ORGANISM: Artificial Sequence
<220> FEATURE:
<223> OTHER INFORMATION: Mutant DBD of ER
```

```
<400> SEQUENCE: 5
tggggctgca aggccttctt caagagatct attaaccgac ataactcc              48

<210> SEQ ID NO 6
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 6

Trp Gly Cys Lys Ala Phe Phe Lys Arg Ser Ile Asn Arg His Asn Ser
1               5                   10                  15

Tyr

<210> SEQ ID NO 7
<211> LENGTH: 48
<212> TYPE: DNA
<213> ORGANISM: Artificial Sequence
<220> FEATURE:
<223> OTHER INFORMATION: Mutant DBD of ER

<400> SEQUENCE: 7
tggggctgca aggccttctt caagagatct attgtacgac ctaccgac              48

<210> SEQ ID NO 8
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 8

Trp Gly Cys Lys Ala Phe Phe Lys Arg Ser Ile Val Arg Pro Thr Asp
1               5                   10                  15

Tyr

<210> SEQ ID NO 9
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 9
gagggctgca aggccttctt caagagaagt attgcaagac gtctcgac              48

<210> SEQ ID NO 10
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 10

Glu Gly Cys Lys Ala Phe Phe Lys Arg Ser Ile Ala Arg Arg Leu Asp
1               5                   10                  15

Tyr

<210> SEQ ID NO 11
<211> LENGTH: 48
<212> TYPE: DNA
<213> ORGANISM: Artificial sequence
```

-continued

```
<220> FEATURE:
<223> OTHER INFORMATION: Mutant DBD of ER

<400> SEQUENCE: 11
tggggctgca aggccttctt caagagatct attgcaagac ataacgac              48

<210> SEQ ID NO 12
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 12

Trp Gly Cys Lys Ala Phe Phe Lys Arg Ser Ile Ala Arg His Asn Asp
1               5                   10                  15
Tyr

<210> SEQ ID NO 13
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 13
tggggctgca aggccttctt caagagatct attgcaagag gtaacgac              48

<210> SEQ ID NO 14
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 14

Trp Gly Cys Lys Ala Phe Phe Lys Arg Ser Ile Ala Arg Gly Asn Asp
1               5                   10                  15
Tyr

<210> SEQ ID NO 15
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 15
tggagctgca aggccttctt caagagatct attgcaggag gtaacgac              48

<210> SEQ ID NO 16
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 16

Trp Ser Cys Lys Ala Phe Phe Lys Arg Ser Ile Ala Gly Gly Asn Asp
1               5                   10                  15
Tyr

<210> SEQ ID NO 17
<211> LENGTH: 48
```

```
<212> TYPE: DNA
<213> ORGANISM: Artificial sequence
<220> FEATURE:
<223> OTHER INFORMATION: Mutant DBD of ER

<400> SEQUENCE: 17
gagggctgca aggccttctt caagagaagt attcaaagac atccccgc                48

<210> SEQ ID NO 18
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 18

Glu Gly Cys Lys Ala Phe Phe Lys Arg Ser Ile Gln Arg His Pro Arg
1               5                   10                  15

Tyr

<210> SEQ ID NO 19
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 19
gagagctgca aggccttctt caagagaagt attggaggac ataactac                48

<210> SEQ ID NO 20
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 20

Glu Ser Cys Lys Ala Phe Phe Lys Arg Ser Ile Gly Gly His Asn Tyr
1               5                   10                  15

Tyr

<210> SEQ ID NO 21
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 21
tggagctgca agggcttctt caagagatct aagcaaggac ataacgac                48

<210> SEQ ID NO 22
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 22

Trp Ser Cys Lys Gly Phe Phe Lys Arg Ser Lys Gln Gly His Asn Asp
1               5                   10                  15

Tyr
```

<210> SEQ ID NO 23
<211> LENGTH: 48
<212> TYPE: DNA
<213> ORGANISM: Artificial sequence
<220> FEATURE:
<223> OTHER INFORMATION: Mutant DBD of ER

<400> SEQUENCE: 23
tggagctgca agggcttctt caagagatct attaaaggag ttcccacc         48

<210> SEQ ID NO 24
<211> LENGTH: 17
<212> TYPE: PRT
<213> ORGANISM: Artificial sequence
<220> FEATURE:
<223> OTHER INFORMATION: Mutant DBD of ER

<400> SEQUENCE: 24

Trp Ser Cys Lys Gly Phe Phe Lys Arg Ser Ile Lys Gly Val Pro Thr
1               5                   10                  15

Tyr

<210> SEQ ID NO 25
<211> LENGTH: 390
<212> TYPE: DNA
<213> ORGANISM: Homo sapiens

<400> SEQUENCE: 25
tccgcgtaca gccgcgcgcg tacgaaaaac aattacgggt ctaccatcga gggcctgctc     60
gatctcccgg acgacgacgc ccccgaagag gcggggctgg cggctccgcg cctgtccttt    120
ctccccgcgg gacacacgcg cagactgtcg acggcccccc cgaccgatgt cagcctgggg    180
gacgagctcc acttagacgg cgaggacgtg gcgatggcgc atgccgacgc gctagacgat    240
ttcgatctgg acatgttggg ggacggggat tccccgggtc cgggatttac ccccacgac    300 tccgcccct acggcgctct ggatatggcc gacttcgagt ttgagcagat gtttaccgat    360
gcccttggaa ttgacgagta cggtgggtag                                     390

<210> SEQ ID NO 26
<211> LENGTH: 129
<212> TYPE: PRT
<213> ORGANISM: Homo sapiens

<400> SEQUENCE: 26

Ser Ala Tyr Ser Arg Ala Arg Thr Lys Asn Asn Tyr Gly Ser Thr Ile
1               5                   10                  15

Glu Gly Leu Leu Asp Leu Pro Asp Asp Ala Pro Glu Glu Ala Gly
            20                  25                  30

Leu Ala Ala Pro Arg Leu Ser Phe Leu Pro Ala Gly His Thr Arg Arg
        35                  40                  45

Leu Ser Thr Ala Pro Pro Thr Asp Val Ser Leu Gly Asp Glu Leu His
    50                  55                  60

Leu Asp Gly Glu Asp Val Ala Met Ala His Ala Asp Ala Leu Asp Asp
65                  70                  75                  80

Phe Asp Leu Asp Met Leu Gly Asp Gly Asp Ser Pro Gly Pro Gly Phe
                85                  90                  95

Thr Pro His Asp Ser Ala Pro Tyr Gly Ala Leu Asp Met Ala Asp Phe
            100                 105                 110

Glu Phe Glu Gln Met Phe Thr Asp Ala Leu Gly Ile Asp Glu Tyr Gly
        115                 120                 125

Gly

<210> SEQ ID NO 27
<211> LENGTH: 58
<212> TYPE: DNA
<213> ORGANISM: Artificial sequence
<220> FEATURE:
<223> OTHER INFORMATION: Primer oligo

<400> SEQUENCE: 27
agcttaggtc actgtgacct atcaagatat cgagataggt cactgtgacc tatcgact        58

<210> SEQ ID NO 28
<211> LENGTH: 58
<212> TYPE: DNA
<213> ORGANISM: Artificial sequence
<220> FEATURE:
<223> OTHER INFORMATION: Primer oligo

<400> SEQUENCE: 28
ctagagtcga taggtcacag tgacctatct cgatatcttg ataggtcaca gtgaccta        58

<210> SEQ ID NO 29
<211> LENGTH: 58
<212> TYPE: DNA
<213> ORGANISM: Artificial sequence
<220> FEATURE:
<223> OTHER INFORMATION: Primer oligo

<400> SEQUENCE: 29
agcttaggtc actgtggccc atcaagatat cgagataggt cactgtggcc catcgact        58

<210> SEQ ID NO 30
<211> LENGTH: 58
<212> TYPE: DNA
<213> ORGANISM: Artificial sequence
<220> FEATURE:
<223> OTHER INFORMATION: primer oligo

<400> SEQUENCE: 30
ctagagtcga tgggccacag tgacctatct cgatatcttg atgggccaca gtgaccta        58

<210> SEQ ID NO 31
<211> LENGTH: 58
<212> TYPE: DNA
<213> ORGANISM: Artificial sequence
<220> FEATURE:
<223> OTHER INFORMATION: primer oligo

<400> SEQUENCE: 31
agcttgggcc actgtggccc atcaagatat cgagatgggc cactgtggcc catcgact        58

<210> SEQ ID NO 32
<211> LENGTH: 58
<212> TYPE: DNA
<213> ORGANISM: Artificial sequence
<220> FEATURE:
<223> OTHER INFORMATION: primer oligo

<400> SEQUENCE: 32
ctagagtcga tgggccacag tggcccatct cgatatcttg atgggccaca gtggccca        58

<210> SEQ ID NO 33
<211> LENGTH: 60
<212> TYPE: DNA

<213> ORGANISM: Artificial sequence
<220> FEATURE:
<223> OTHER INFORMATION: primer oligo

<400> SEQUENCE: 33
agcttaggtc actgtgacct atcaagatat cgagataggt cactgtgacc tatcgacagg        60

<210> SEQ ID NO 34
<211> LENGTH: 60
<212> TYPE: DNA
<213> ORGANISM: Artificial sequence
<220> FEATURE:
<223> OTHER INFORMATION: primer oligo

<400> SEQUENCE: 34
aattcctgtc gataggtcac agtgacctat ctcgatatct tgataggtca cagtgaccta        60

<210> SEQ ID NO 35
<211> LENGTH: 60
<212> TYPE: DNA
<213> ORGANISM: Artificial sequence
<220> FEATURE:
<223> OTHER INFORMATION: primer oligo

<400> SEQUENCE: 35
aattcacagg tcactgtgac ctatcaagat atcgagatag gtcactgtga cctatcgact        60

<210> SEQ ID NO 36
<211> LENGTH: 60
<212> TYPE: DNA
<213> ORGANISM: artificial sequence
<220> FEATURE:
<223> OTHER INFORMATION: primer oligo

<400> SEQUENCE: 36
ctagagtcga taggtcacag tgacctatct cgatatcttg ataggtcaca gtgacctgtg        60

<210> SEQ ID NO 37
<211> LENGTH: 60
<212> TYPE: DNA
<213> ORGANISM: artificial sequence
<220> FEATURE:
<223> OTHER INFORMATION: primer oligo

<400> SEQUENCE: 37
agcttgggcc actgtggccc atcaagatat cgagatgggc cactgtggcc catcgacagg        60

<210> SEQ ID NO 38
<211> LENGTH: 60
<212> TYPE: DNA
<213> ORGANISM: Artificial sequence
<220> FEATURE:
<223> OTHER INFORMATION: primer oligo

<400> SEQUENCE: 38
aattcctgtc gatgggccac agtggcccat ctcgatatct tgatgggcca cagtggccca        60

<210> SEQ ID NO 39
<211> LENGTH: 60
<212> TYPE: DNA
<213> ORGANISM: Artificial sequence
<220> FEATURE:
<223> OTHER INFORMATION: primer oligo

<400> SEQUENCE: 39
aattcacggg ccactgtggc ccatcaagat atcgagatgg gccactgtgg cccatcgact        60

<210> SEQ ID NO 40
<211> LENGTH: 60
<212> TYPE: DNA
<213> ORGANISM: artificial sequence
<220> FEATURE:
<223> OTHER INFORMATION: primer oligo

<400> SEQUENCE: 40
ctagagtcga tgggccacag tggcccatct cgatatcttg atgggccaca gtggcccgtg    60

<210> SEQ ID NO 41
<211> LENGTH: 62
<212> TYPE: DNA
<213> ORGANISM: artificial sequence
<220> FEATURE:
<223> OTHER INFORMATION: primer oligo

<400> SEQUENCE: 41
ctagcgggcc actgtggccc tgacaactag taagtcgggc cactgtggcc cgacgtacta    60
tc                                                                   62

<210> SEQ ID NO 42
<211> LENGTH: 62
<212> TYPE: DNA
<213> ORGANISM: artificial sequence
<220> FEATURE:
<223> OTHER INFORMATION: primer oligo

<400> SEQUENCE: 42
tcgagatagt acgtcgggcc acagtggccc gacttactag ttgtcagggc cacagtggcc    60
cg                                                                   62

<210> SEQ ID NO 43
<211> LENGTH: 62
<212> TYPE: DNA
<213> ORGANISM: artificial sequence
<220> FEATURE:
<223> OTHER INFORMATION: primer oligo

<400> SEQUENCE: 43
tcgaggggcc actgtggccc tagagctgca ggtatcgggc cactgtggcc ctagttcatt    60
aa                                                                   62

<210> SEQ ID NO 44
<211> LENGTH: 62
<212> TYPE: DNA
<213> ORGANISM: artificial sequence
<220> FEATURE:
<223> OTHER INFORMATION: primer oligo

<400> SEQUENCE: 44
agctttaatg aactagggcc acagtggccc gatacctgca gctctagggc cacagtggcc    60
cc                                                                   62

<210> SEQ ID NO 45
<211> LENGTH: 62
<212> TYPE: DNA
<213> ORGANISM: artificial sequence
<220> FEATURE:
<223> OTHER INFORMATION: primer oligo

<400> SEQUENCE: 45
ctagcaggtc actgtgacct tgacaactag taagtcaggt cactgtgacc tgacgtacta    60
tc    62

<210> SEQ ID NO 46
<211> LENGTH: 62
<212> TYPE: DNA
<213> ORGANISM: artificial sequence
<220> FEATURE:
<223> OTHER INFORMATION: primer oligo

<400> SEQUENCE: 46
tcgagatagt acgtcaggtc acagtgacct gacttactag ttgtcaaggt cacagtgacc    60
tg    62

<210> SEQ ID NO 47
<211> LENGTH: 62
<212> TYPE: DNA
<213> ORGANISM: artificial sequence
<220> FEATURE:
<223> OTHER INFORMATION: primer oligo

<400> SEQUENCE: 47
tcgagaggtc actgtgacct tagagctgca ggtatcaggt cactgtgacc ttagttcatt    60
aa    62

<210> SEQ ID NO 48
<211> LENGTH: 62
<212> TYPE: DNA
<213> ORGANISM: artificial sequence
<220> FEATURE:
<223> OTHER INFORMATION: primer oligo

<400> SEQUENCE: 48
agctttaatg aactaaggtc acagtgacct gatacctgca gctctaaggt cacagtgacc    60
tc    62

<210> SEQ ID NO 49
<211> LENGTH: 46
<212> TYPE: DNA
<213> ORGANISM: artificial sequence
<220> FEATURE:
<223> OTHER INFORMATION: primer oligo

<400> SEQUENCE: 49
cggggtaccg gccacggacc atgtccgcgt acagccgcgc gcgtac    46

<210> SEQ ID NO 50
<211> LENGTH: 31
<212> TYPE: DNA
<213> ORGANISM: artificial sequence
<220> FEATURE:
<223> OTHER INFORMATION: primer oligo

<400> SEQUENCE: 50
ctagtctaga cccaccgtac tcgtcaattc c    31

<210> SEQ ID NO 51
<211> LENGTH: 44
<212> TYPE: DNA
<213> ORGANISM: artificial sequence
<220> FEATURE:
<223> OTHER INFORMATION: primer oligo

<400> SEQUENCE: 51

```
cggggtaccg gccacggacc atgacggccc ccccgaccga tgtc          44
```

<210> SEQ ID NO 52
<211> LENGTH: 31
<212> TYPE: DNA
<213> ORGANISM: artificial sequence
<220> FEATURE:
<223> OTHER INFORMATION: primer oligo

<400> SEQUENCE: 52

```
tctagctagc atgaccatga ccctccacac c                        31
```

<210> SEQ ID NO 53
<211> LENGTH: 28
<212> TYPE: DNA
<213> ORGANISM: artificial sequence
<220> FEATURE:
<223> OTHER INFORMATION: primer oligo

<400> SEQUENCE: 53

```
ataagaatgc ggccgcggcg ttgaactc                            28
```

<210> SEQ ID NO 54
<211> LENGTH: 33
<212> TYPE: DNA
<213> ORGANISM: artificial sequence
<220> FEATURE:
<223> OTHER INFORMATION: primer oligo

<400> SEQUENCE: 54

```
atcgggtacc tccgcgtaca gccgcgcgcg tac                      33
```

<210> SEQ ID NO 55
<211> LENGTH: 21
<212> TYPE: DNA
<213> ORGANISM: artificial sequence
<220> FEATURE:
<223> OTHER INFORMATION: primer oligo

<400> SEQUENCE: 55

```
cttatcatgt ctggatcctc g                                   21
```

<210> SEQ ID NO 56
<211> LENGTH: 31
<212> TYPE: DNA
<213> ORGANISM: artificial sequence
<220> FEATURE:
<223> OTHER INFORMATION: primer oligo

<400> SEQUENCE: 56

```
atcgggtacc acggcccccc cgaccgatgt c                        31
```

<210> SEQ ID NO 57
<211> LENGTH: 22
<212> TYPE: DNA
<213> ORGANISM: artificial sequence
<220> FEATURE:
<223> OTHER INFORMATION: primer oligo

<400> SEQUENCE: 57

```
caggtccacc ttctagaatg tg                                  22
```

<210> SEQ ID NO 58
<211> LENGTH: 30
<212> TYPE: DNA

```
<213> ORGANISM: artificial sequence
<220> FEATURE:
<223> OTHER INFORMATION: primer oligo

<400> SEQUENCE: 58
cggggtaccg actgtggcag ggaaaccctc                                          30

<210> SEQ ID NO 59
<211> LENGTH: 25
<212> TYPE: DNA
<213> ORGANISM: artificial sequence
<220> FEATURE:
<223> OTHER INFORMATION: primer oligo

<400> SEQUENCE: 59
cacggaccat ggcggccccc ccgac                                               25

<210> SEQ ID NO 60
<211> LENGTH: 28
<212> TYPE: DNA
<213> ORGANISM: artificial sequence
<220> FEATURE:
<223> OTHER INFORMATION: primer oligo

<400> SEQUENCE: 60
ataagaatgc ggccgcggcg ttgaactc                                            28

<210> SEQ ID NO 61
<211> LENGTH: 39
<212> TYPE: DNA
<213> ORGANISM: artificial sequence
<220> FEATURE:
<223> OTHER INFORMATION: probe oligo

<400> SEQUENCE: 61
agcttctcta ttaggtcact gtgaccttca tctgaagct                                39

<210> SEQ ID NO 62
<211> LENGTH: 39
<212> TYPE: DNA
<213> ORGANISM: artificial sequence
<220> FEATURE:
<223> OTHER INFORMATION: probe oligo

<400> SEQUENCE: 62
agcttctcta ttgggccact gtgaccttca tctgaagct                                39

<210> SEQ ID NO 63
<211> LENGTH: 39
<212> TYPE: DNA
<213> ORGANISM: artificial sequence
<220> FEATURE:
<223> OTHER INFORMATION: probe oligo

<400> SEQUENCE: 63
agcttctcta ttgggccact gtggccctca tctgaagct                                39

<210> SEQ ID NO 64
<211> LENGTH: 39
<212> TYPE: DNA
<213> ORGANISM: artificial sequence
<220> FEATURE:
<223> OTHER INFORMATION: probe oligo

<400> SEQUENCE: 64
agcttcagat gagggccaca gtggcccaat agagaagct                                39
```

<210> SEQ ID NO 65
<211> LENGTH: 6
<212> TYPE: DNA
<213> ORGANISM: artificial sequence
<220> FEATURE:
<223> OTHER INFORMATION: cERE half site

<400> SEQUENCE: 65 aggtca                                                                          6

<210> SEQ ID NO 66
<211> LENGTH: 2181
<212> TYPE: DNA
<213> ORGANISM: Artificial sequence
<220> FEATURE:
<223> OTHER INFORMATION: construct

<400> SEQUENCE: 66

```
atgtccgcgt acagccgcgc gcgtacgaaa acaattacg  ggtctaccat cgagggcctg        60
ctcgatctcc cggacgacga cgcccccgaa gaggcgggc  tggcggctcc gcgcctgtcc       120
tttctccccg cgggacacac gcgcagactg tcgacggccc cccgaccga  tgtcagcctg       180
ggggacgagc tccacttaga cggcgaggac gtggcgatgg cgcatgccga cgcgctagac       240
gatttcgatc tggacatgtt gggggacggg gattccccgg gtccgggatt accccccac        300
gactccgccc cctacggcgc tctggatatg gccgacttcg agtttgagca gatgtttacc       360
gatgcccttg gaattgacga gtacggtggg tctagcatga ccatgaccct ccacaccaaa       420
gcatctggga tggccctact gcatcagatc aagggaacg  agctggagcc cctgaaccgt       480
ccgcagctca agatccccct ggagcggccc ctgggcgagg tgtacctgga cagcagcaag       540
cccgccgtgt acaactaccc cgagggcgcc gcctacgagt tcaacgccgc ggccgccgcc       600
aacgcgcagg tctacggtca gaccggcctc ccctacggcc ccgggtctga ggctgcggcg       660
ttcggctcca acggcctggg gggtttcccc ccactcaaca gcgtgtctcc gagcccgctg       720
atgctactgc acccgccgcc gcagctgtcg ccttttcctgc agccccacgg ccagcaggtg       780
ccctactacc tggagaacga gcccagcggc tacacggtgc gcgaggccgg cccgccggca       840
ttctacaggc aaattcaga  taatcgacgc cagggtggca gagaaagatt ggccagtacc       900
aatgacaagg gaagtatggc tatggaatct gccaaggaga ctcgctactg tgcagtgtgc       960
aatgactatg cttcaggcta ccattatgga gtctggtcct gttggggctg caaggccttc      1020
ttcaagagat ctattgcagg aggtaacgac tatatgtgtc cagccaccaa ccagtgcacc      1080
attgataaaa acaggaggaa gagctgccag gcctgccggc tccgcaaatg ctacgaagtg      1140
ggaatgatga aggtgggat  acgaaaagac cgaagaggag ggagaatgtt gaaacacaag      1200
cgccagagag atgatgggga gggcaggggt gaagtgggg  ctgctggaga catgagagct      1260
gccaaccttt ggccaagccc gctcatgatc aaacgctcta agaagaacag cctggccttg      1320
tccctgacgg ccgaccagat ggtcagtgcc ttgttggatg ctgagccccc catactctat      1380
tccgagtatg atcctaccag acccttcagt gaagcttcga tgatgggctt actgaccaac      1440
ctggcagaca gggagctggt tcacatgatc aactgggcga agagggtgcc aggctttgtg      1500
gatttgaccc tccatgatca ggtccacctt ctagaatgtg cctggctaga gatcctgatg      1560
attggtctcg tctggcgctc catggagcac ccagtgaagc tactgtttgc tcctaacttg      1620
ctcttggaca ggaaccaggg aaaatgtgta gagggcatgg tggagatctt cgacatgctg      1680
```

-continued

```
ctggctacat catctcggtt ccgcatgatg aatctgcagg gagaggagtt tgtgtgcctc    1740
aaatctatta ttttgcttaa ttctggagtg tacacatttc tgtccagcac cctgaagtct    1800
ctggaagaga aggaccatat ccaccgagtc ctggacaaga tcacagacac tttgatccac    1860
ctgatggcca aggcaggcct gaccctgcag cagcagcacc agcggctggc ccagctcctc    1920
ctcatcctct cccacatcag gcacatgagt aacaaaggca tggagcatct gtacagcatg    1980
aagtgcaaga acgtggtgcc cctctatgac ctgctgctgg agatgctgga cgcccaccgc    2040
ctacatgcgc ccactagccg tggaggggca tccgtggagg agacggacca aagccacttg    2100
gccactgcgg gctctacttc atcgcattcc ttgcaaaagt attacatcac gggggaggca    2160
gagggtttcc ctgccacagt c                                              2181
```

<210> SEQ ID NO 67
<211> LENGTH: 727
<212> TYPE: PRT
<213> ORGANISM: Artificial sequence
<220> FEATURE:
<223> OTHER INFORMATION: fusion polypeptide

<400> SEQUENCE: 67

```
Met Ser Ala Tyr Ser Arg Ala Arg Thr Lys Asn Asn Tyr Gly Ser Thr
1               5                   10                  15
Ile Glu Gly Leu Leu Asp Leu Pro Asp Asp Ala Pro Glu Glu Ala
            20                  25                  30
Gly Leu Ala Ala Pro Arg Leu Ser Phe Leu Pro Ala Gly His Thr Arg
        35                  40                  45
Arg Leu Ser Thr Ala Pro Pro Thr Asp Val Ser Leu Gly Asp Glu Leu
    50                  55                  60
His Leu Asp Gly Glu Asp Val Ala Met Ala His Ala Asp Ala Leu Asp
65                  70                  75                  80
Asp Phe Asp Leu Asp Met Leu Gly Asp Gly Asp Ser Pro Gly Pro Gly
                85                  90                  95
Phe Thr Pro His Asp Ser Ala Pro Tyr Gly Ala Leu Asp Met Ala Asp
            100                 105                 110
Phe Glu Phe Glu Gln Met Phe Thr Asp Ala Leu Gly Ile Asp Glu Tyr
        115                 120                 125
Gly Gly Ser Ser Met Thr Met Thr Leu His Thr Lys Ala Ser Gly Met
    130                 135                 140
Ala Leu Leu His Gln Ile Gln Gly Asn Glu Leu Glu Pro Leu Asn Arg
145                 150                 155                 160
Pro Gln Leu Lys Ile Pro Leu Glu Arg Pro Leu Gly Glu Val Tyr Leu
                165                 170                 175
Asp Ser Ser Lys Pro Ala Val Tyr Asn Tyr Pro Glu Gly Ala Ala Tyr
            180                 185                 190
Glu Phe Asn Ala Ala Ala Ala Asn Ala Gln Val Tyr Gly Gln Thr
        195                 200                 205
Gly Leu Pro Tyr Gly Pro Gly Ser Glu Ala Ala Phe Gly Ser Asn
    210                 215                 220
Gly Leu Gly Gly Phe Pro Pro Leu Asn Ser Val Ser Pro Ser Pro Leu
225                 230                 235                 240
Met Leu Leu His Pro Pro Gln Leu Ser Pro Phe Leu Gln Pro His
                245                 250                 255
Gly Gln Gln Val Pro Tyr Tyr Leu Glu Asn Glu Pro Ser Gly Tyr Thr
            260                 265                 270
Val Arg Glu Ala Gly Pro Pro Ala Phe Tyr Arg Pro Asn Ser Asp Asn
        275                 280                 285
Arg Arg Gln Gly Gly Arg Glu Arg Leu Ala Ser Thr Asn Asp Lys Gly
    290                 295                 300
Ser Met Ala Met Glu Ser Ala Lys Glu Thr Arg Tyr Cys Ala Val Cys
305                 310                 315                 320
Asn Asp Tyr Ala Ser Gly Tyr His Tyr Gly Val Trp Ser Cys Trp Gly
                325                 330                 335
Cys Lys Ala Phe Phe Lys Arg Ser Ile Ala Gly Asn Asp Tyr Met
            340                 345                 350
Cys Pro Ala Thr Asn Gln Cys Thr Ile Asp Lys Asn Arg Arg Lys Ser
        355                 360                 365
Cys Gln Ala Cys Arg Leu Arg Lys Cys Tyr Glu Val Gly Met Met Lys
    370                 375                 380
Gly Gly Ile Arg Lys Asp Arg Arg Gly Gly Arg Met Leu Lys His Lys
385                 390                 395                 400
Arg Gln Arg Asp Asp Gly Glu Gly Arg Gly Glu Val Gly Ser Ala Gly
```

```
                        405                 410                 415
Asp Met Arg Ala Ala Asn Leu Trp Pro Ser Pro Leu Met Ile Lys Arg
                420                 425                 430
Ser Lys Lys Asn Ser Leu Ala Leu Ser Leu Thr Ala Asp Gln Met Val
            435                 440                 445
Ser Ala Leu Leu Asp Ala Glu Pro Pro Ile Leu Tyr Ser Glu Tyr Asp
        450                 455                 460
Pro Thr Arg Pro Phe Ser Glu Ala Ser Met Met Gly Leu Leu Thr Asn
465                 470                 475                 480
Leu Ala Asp Arg Glu Leu Val His Met Ile Asn Trp Ala Lys Arg Val
                485                 490                 495
Pro Gly Phe Val Asp Leu Thr Leu His Asp Gln Val His Leu Leu Glu
                500                 505                 510
Cys Ala Trp Leu Glu Ile Leu Met Ile Gly Leu Val Trp Arg Ser Met
                515                 520                 525
Glu His Pro Val Lys Leu Leu Phe Ala Pro Asn Leu Leu Leu Asp Arg
            530                 535                 540
Asn Gln Gly Lys Cys Val Glu Gly Met Val Glu Ile Phe Asp Met Leu
545                 550                 555                 560
Leu Ala Thr Ser Ser Arg Phe Arg Met Met Asn Leu Gln Gly Glu Glu
                565                 570                 575
Phe Val Cys Leu Lys Ser Ile Ile Leu Leu Asn Ser Gly Val Tyr Thr
            580                 585                 590
Phe Leu Ser Ser Thr Leu Lys Ser Leu Glu Glu Lys Asp His Ile His
        595                 600                 605
Arg Val Leu Asp Lys Ile Thr Asp Thr Leu Ile His Leu Met Ala Lys
    610                 615                 620
Ala Gly Leu Thr Leu Gln Gln Gln His Gln Arg Leu Ala Gln Leu Leu
625                 630                 635                 640
Leu Ile Leu Ser His Ile Arg His Met Ser Asn Lys Gly Met Glu His
                645                 650                 655
Leu Tyr Ser Met Lys Cys Lys Asn Val Val Pro Leu Tyr Asp Leu Leu
                660                 665                 670
Leu Glu Met Leu Asp Ala His Arg Leu His Ala Pro Thr Ser Arg Gly
                675                 680                 685
Gly Ala Ser Val Glu Glu Thr Asp Gln Ser His Leu Ala Thr Ala Gly
            690                 695                 700
Ser Thr Ser Ser His Ser Leu Gln Lys Tyr Tyr Ile Thr Gly Glu Ala
705                 710                 715                 720
Glu Gly Phe Pro Ala Thr Val
                725

<210> SEQ ID NO 68
<211> LENGTH: 2031
<212> TYPE: DNA
<213> ORGANISM: Artificial sequence
<220> FEATURE:
<223> OTHER INFORMATION: construct

<400> SEQUENCE: 68
atgacggccc ccccgaccga tgtcagcctg ggggacgagc tccacttaga cggcgaggac      60
gtggcgatgg cgcatgccga cgcgctagac gatttcgatc tggacatgtt ggggacgggg     120
gattccccgg gtccgggatt taccccccac gactccgccc cctacggcgc tctggatatg     180
gccgacttcg agtttgagca gatgtttacc gatgcccttg gaattgacga gtacggtggg     240
tctagcatga ccatgacccc ccacaccaaa gcatctggga tggccctact gcatcagatc     300
caagggaacg agctggagcc cctgaaccgt ccgcagctca agatccccct ggagcggccc     360
ctgggcgagg tgtacctgga cagcagcaag cccgccgtgt acaactaccc cgagggcgcc     420
gcctacgagt tcaacgccgc ggccgccgcc aacgcgcagg tctacggtca gaccggcctc     480
ccctacggcc ccgggtctga ggctgcggcg ttcggctcca acggcctggg ggtttccccc     540
ccactcaaca gcgtgtctcc gagcccgctg atgctactgc accgccgcc gcagctgtcg     600 cctttcctgc agcccacgg ccagcaggtg ccctactacc tggagaacga gcccagcggc     660
tacacggtgc gcgaggccgg cccgccggca ttctacaggc caattcaga taatcgacgc     720 cagggtggca gagaaagatt ggccagtacc aatgacaagg gaagtatggc tatggaatct     780
gccaaggaga ctcgctactg tgcagtgtgc aatgactatg cttcaggcta ccattatgga     840
```

-continued

```
gtctggtcct gttggggctg caaggccttc ttcaagagat ctattgcagg aggtaacgac      900
tatatgtgtc cagccaccaa ccagtgcacc attgataaaa acaggaggaa gagctgccag      960
gcctgccggc tccgcaaatg ctacgaagtg ggaatgatga aagtgggat acgaaaagac      1020
cgaagaggag ggagaatgtt gaaacacaag cgccagagag atgatgggga gggcagggggt    1080
gaagtggggt ctgctggaga catgagagct gccaacctttt ggccaagccc gctcatgatc    1140
aaacgctcta agaagaacag cctggccttg tccctgacgg ccgaccagat ggtcagtgcc     1200
ttgttggatg ctgagccccc catactctat tccgagtatg atcctaccag acccttcagt     1260
gaagcttcga tgatgggctt actgaccaac ctggcagaca gggagctggt tcacatgatc     1320
aactgggcga gagggtgcc aggctttgtg gatttgaccc tccatgatca ggtccacctt      1380
ctagaatgtg cctggctaga gatcctgatg attggtctcg tctggcgctc catggagcac     1440
ccagtgaagc tactgtttgc tcctaacttg ctcttggaca ggaaccaggg aaaatgtgta     1500
gagggcatgg tggagatctt cgacatgctg ctggctacat catctcggtt ccgcatgatg     1560
aatctgcagg gagaggagtt tgtgtgcctc aaatctatta ttttgcttaa ttctggagtg     1620
tacacatttc tgtccagcac cctgaagtct ctggaagaga aggaccatat ccaccgagtc     1680
ctggacaaga tcacagacac tttgatccac ctgatggcca aggcaggcct gaccctgcag     1740
cagcagcacc agcggctggc ccagctcctc ctcatcctct cccacatcag gcacatgagt     1800
aacaaaggca tggagcatct gtacagcatg aagtgcaaga acgtggtgcc cctctatgac     1860
ctgctgctgg agatgctgga cgcccaccgc ctacatgcgc ccactagccg tggaggggca    1920
tccgtggagg agacggacca aagccacttg gccactgcgg gctctacttc atcgcattcc     1980
ttgcaaaagt attacatcac gggggaggca gagggtttcc ctgccacagt c              2031
```

<210> SEQ ID NO 69
<211> LENGTH: 677
<212> TYPE: PRT
<213> ORGANISM: Artificial sequence
<220> FEATURE:
<223> OTHER INFORMATION: fusion polypeptide

<400> SEQUENCE: 69

```
Met Thr Ala Pro Pro Thr Asp Val Ser Leu Gly Asp Glu Leu His Leu
1               5                   10                  15

Asp Gly Glu Asp Val Ala Met Ala His Ala Asp Ala Leu Asp Asp Phe
            20                  25                  30

Asp Leu Asp Met Leu Gly Asp Gly Asp Ser Pro Gly Pro Gly Phe Thr
        35                  40                  45

Pro His Asp Ser Ala Pro Tyr Gly Ala Leu Asp Met Ala Asp Phe Glu
    50                  55                  60

Phe Glu Gln Met Phe Thr Asp Ala Leu Gly Ile Asp Glu Tyr Gly Gly
65                  70                  75                  80

Ser Ser Met Thr Met Thr Leu His Thr Lys Ala Ser Gly Met Ala Leu
                85                  90                  95

Leu His Gln Ile Gln Gly Asn Glu Leu Glu Pro Leu Asn Arg Pro Gln
            100                 105                 110

Leu Lys Ile Pro Leu Glu Arg Pro Leu Gly Glu Val Tyr Leu Asp Ser
        115                 120                 125

Ser Lys Pro Ala Val Tyr Asn Tyr Pro Glu Gly Ala Ala Tyr Glu Phe
    130                 135                 140

Asn Ala Ala Ala Ala Ala Asn Ala Gln Val Tyr Gly Gln Thr Gly Leu
```

-continued

```
            145                 150                 155                 160
Pro Tyr Gly Pro Gly Ser Glu Ala Ala Phe Gly Ser Asn Gly Leu
                165                 170                 175
Gly Gly Phe Pro Pro Leu Asn Ser Val Ser Pro Ser Pro Leu Met Leu
                180                 185                 190
Leu His Pro Pro Pro Gln Leu Ser Pro Phe Leu Gln Pro His Gly Gln
                195                 200                 205
Gln Val Pro Tyr Tyr Leu Glu Asn Glu Pro Ser Gly Tyr Thr Val Arg
                210                 215                 220
Glu Ala Gly Pro Pro Ala Phe Tyr Arg Pro Asn Ser Asp Asn Arg Arg
225                 230                 235                 240
Gln Gly Gly Arg Glu Arg Leu Ala Ser Thr Asn Asp Lys Gly Ser Met
                245                 250                 255
Ala Met Glu Ser Ala Lys Glu Thr Arg Tyr Cys Ala Val Cys Asn Asp
                260                 265                 270
Tyr Ala Ser Gly Tyr His Tyr Gly Val Trp Ser Cys Trp Gly Cys Lys
                275                 280                 285
Ala Phe Phe Lys Arg Ser Ile Ala Gly Gly Asn Asp Tyr Met Cys Pro
                290                 295                 300
Ala Thr Asn Gln Cys Thr Ile Asp Lys Asn Arg Arg Lys Ser Cys Gln
305                 310                 315                 320
Ala Cys Arg Leu Arg Lys Cys Tyr Glu Val Gly Met Met Lys Gly Gly
                325                 330                 335
Ile Arg Lys Asp Arg Arg Gly Gly Arg Met Leu Lys His Lys Arg Gln
                340                 345                 350
Arg Asp Asp Gly Glu Gly Arg Gly Glu Val Gly Ser Ala Gly Asp Met
                355                 360                 365
Arg Ala Ala Asn Leu Trp Pro Ser Pro Leu Met Ile Lys Arg Ser Lys
                370                 375                 380
Lys Asn Ser Leu Ala Leu Ser Leu Thr Ala Asp Gln Met Val Ser Ala
385                 390                 395                 400
Leu Leu Asp Ala Glu Pro Pro Ile Leu Tyr Ser Glu Tyr Asp Pro Thr
                405                 410                 415
Arg Pro Phe Ser Glu Ala Ser Met Met Gly Leu Leu Thr Asn Leu Ala
                420                 425                 430
Asp Arg Glu Leu Val His Met Ile Asn Trp Ala Lys Arg Val Pro Gly
                435                 440                 445
Phe Val Asp Leu Thr Leu His Asp Gln Val His Leu Leu Glu Cys Ala
                450                 455                 460
Trp Leu Glu Ile Leu Met Ile Gly Leu Val Trp Arg Ser Met Glu His
465                 470                 475                 480
Pro Val Lys Leu Leu Phe Ala Pro Asn Leu Leu Leu Asp Arg Asn Gln
                485                 490                 495
Gly Lys Cys Val Glu Gly Met Val Glu Ile Phe Asp Met Leu Leu Ala
                500                 505                 510
Thr Ser Ser Arg Phe Arg Met Met Asn Leu Gln Gly Glu Glu Phe Val
                515                 520                 525
Cys Leu Lys Ser Ile Ile Leu Leu Asn Ser Gly Val Tyr Thr Phe Leu
                530                 535                 540
Ser Ser Thr Leu Lys Ser Leu Glu Glu Lys Asp His Ile His Arg Val
545                 550                 555                 560
Leu Asp Lys Ile Thr Asp Thr Leu Ile His Leu Met Ala Lys Ala Gly
                565                 570                 575
```

```
Leu Thr Leu Gln Gln Gln His Gln Arg Leu Ala Gln Leu Leu Leu Ile
            580                 585                 590

Leu Ser His Ile Arg His Met Ser Asn Lys Gly Met Glu His Leu Tyr
            595                 600                 605

Ser Met Lys Cys Lys Asn Val Val Pro Leu Tyr Asp Leu Leu Glu
            610                 615                 620

Met Leu Asp Ala His Arg Leu His Ala Pro Thr Ser Arg Gly Gly Ala
625                 630                 635                 640

Ser Val Glu Glu Thr Asp Gln Ser His Leu Ala Thr Ala Gly Ser Thr
                645                 650                 655

Ser Ser His Ser Leu Gln Lys Tyr Tyr Ile Thr Gly Glu Ala Glu Gly
            660                 665                 670

Phe Pro Ala Thr Val
            675

<210> SEQ ID NO 70
<211> LENGTH: 2178
<212> TYPE: DNA
<213> ORGANISM: Artificial sequence
<220> FEATURE:
<223> OTHER INFORMATION: construct

<400> SEQUENCE: 70
```

| | | |
|---|---|---|
| atgaccatga ccctccacac caaagcatct gggatggccc tactgcatca gatccaaggg | 60 |
| aacgagctgg agcccctgaa ccgtccgcag ctcaagatcc ccctggagcg gccccctggg c | 120 |
| gaggtgtacc tggacagcag caagcccgcc gtgtacaact ccccgaggg cgccgcctac | 180 |
| gagttcaacg ccgcggccgc cgccaacgcg caggtctacg gtcagaccgg cctcccctac | 240 |
| ggccccgggt ctgaggctgc ggcgttcggc tccaacggcc tggggggtttt ccccccactc | 300 |
| aacagcgtgt ctccgagccc gctgatgcta ctgcacccgc gccgcagct gtcgcctttc | 360 |
| ctgcagcccc acgccagca ggtgccctac tacctggaga cgagcccag cggctacacg | 420 |
| gtgcgcgagg ccgccccgcc ggcattctac aggccaaatt cagataatcg acgccagggt | 480 |
| ggcagagaaa gattggccag taccaatgac aagggaagta tggctatgga atctgccaag | 540 |
| gagactcgct actgtgcagt gtgcaatgac tatgcttcag gctaccatta tggagtctgg | 600 |
| tcctgttggg gctgcaaggc cttcttcaag agatctattg caggaggtaa cgactatatg | 660 |
| tgtccagcca ccaaccagtg caccattgat aaaaacagga ggaagagctg ccaggcctgc | 720 |
| cggctccgca atgctacga agtgggaatg atgaaaggtg ggatacgaaa agaccgaaga | 780 |
| ggagggagaa tgttgaaaca caagcgccag agagatgatg gggagggcag gggtgaagtg | 840 |
| gggtctgctg gagacatgag agctgccaac ctttggccaa gcccgctcat gatcaaacgc | 900 |
| tctaagaaga cagcctggc cttgtccctg acggccgacc agatggtcag tgccttgttg | 960 |
| gatgctgagc cccccatact ctattccgag tatgatccta ccagacccTT cagtgaagct | 1020 |
| tcgatgatgg gcttactgac caacctggca gacagggagc tggttcacat gatcaactgg | 1080 |
| gcgaagaggg tgccaggctt tgtggatttg accctccatg atcaggtcca ccttctagaa | 1140 |
| tgtgcctggc tagagatcct gatgattggt ctcgtctggc gctccatgga gcacccagtg | 1200 |
| aagctactgt ttgctcctaa cttgctcttg acaggaacc aggaaaaatg tgtagagggc | 1260 |
| atggtggaga tcttcgacat gctgctggct acatcatctc ggttccgcat gatgaatctg | 1320 |
| cagggagagg agtttgtgtg cctcaaatct attattttgc ttaattctgg agtgtacaca | 1380 |
| tttctgtcca gcaccctgaa gtctctggaa gagaaggacc atatccaccg agtcctggac | 1440 |

-continued

```
aagatcacag acactttgat ccacctgatg gccaaggcag gcctgaccct gcagcagcag      1500
caccagcggc tggcccagct cctcctcatc ctctcccaca tcaggcacat gagtaacaaa      1560
ggcatggagc atctgtacag catgaagtgc aagaacgtgg tgcccctcta tgacctgctg      1620
ctggagatgc tggacgccca ccgcctacat gcgcccacta gccgtggagg ggcatccgtg      1680
gaggagacgg accaaagcca cttggccact gcgggctcta cttcatcgca ttccttgcaa      1740 agtattaca  tcacggggga ggcagagggt ttccctgcca cagtcggtac ctccgcgtac      1800
agccgcgcgc gtacgaaaaa caattacggg tctaccatcg agggcctgct cgatctcccg      1860
gacgacgacg cccccgaaga ggcggggctg gcggctccgc gcctgtcctt tctccccgcg      1920
ggacacacgc gcagactgtc gacggccccc ccgaccgatg tcagcctggg ggacgagctc      1980
cacttagacg gcgaggacgt ggcgatggcg catgccgacg cgctagacga tttcgatctg      2040
gacatgttgg gggacgggga ttccccgggt ccgggattta cccccacga  ctccgccccc      2100 tacggcgctc tggatatggc cgacttcgag tttgagcaga tgtttaccga tgcccttgga      2160
attgacgagt acggtggg                                                   2178
```

<210> SEQ ID NO 71
<211> LENGTH: 726
<212> TYPE: PRT
<213> ORGANISM: Artificial sequence
<220> FEATURE:
<223> OTHER INFORMATION: fusion polypeptide

<400> SEQUENCE: 71

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Trp Gly Cys Lys Ala Phe
        195                 200                 205

Phe Lys Arg Ser Ile Ala Gly Gly Asn Asp Tyr Met Cys Pro Ala Thr
    210                 215                 220
```

-continued

```
Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
            245                 250                 255

Lys Asp Arg Arg Gly Gly Arg Met Leu Lys His Lys Arg Gln Arg Asp
        260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Gly Thr Ser Ala Tyr Ser Arg Ala Arg Thr Lys Asn Asn
        595                 600                 605

Tyr Gly Ser Thr Ile Glu Gly Leu Leu Asp Leu Pro Asp Asp Asp Ala
    610                 615                 620

Pro Glu Glu Ala Gly Leu Ala Ala Pro Arg Leu Ser Phe Leu Pro Ala
625                 630                 635                 640

Gly His Thr Arg Arg Leu Ser Thr Ala Pro Pro Thr Asp Val Ser Leu
```

```
                      645                 650                 655
        Gly Asp Glu Leu His Leu Asp Gly Glu Asp Val Ala Met Ala His Ala
                660                 665                 670

Asp Ala Leu Asp Asp Phe Asp Leu Asp Met Leu Gly Asp Gly Asp Ser
                675                 680                 685

Pro Gly Pro Gly Phe Thr Pro His Asp Ser Ala Pro Tyr Gly Ala Leu
                690                 695                 700

Asp Met Ala Asp Phe Glu Phe Glu Gln Met Phe Thr Asp Ala Leu Gly
        705                 710                 715                 720

Ile Asp Glu Tyr Gly Gly
                    725

<210> SEQ ID NO 72
<211> LENGTH: 2028
<212> TYPE: DNA
<213> ORGANISM: Artificial sequence
<220> FEATURE:
<223> OTHER INFORMATION: construct

<400> SEQUENCE: 72
atgaccatga ccctccacac caaagcatct gggatggccc tactgcatca gatccaaggg      60
aacgagctgg agcccctgaa ccgtccgcag ctcaagatcc ccctggagcg gcccctgggc     120
gaggtgtacc tggacagcag caagcccgcc gtgtacaact accccgaggg cgccgcctac     180
gagttcaacg ccgcggccgc cgccaacgcg caggtctacg tcagaccgg cctcccctac      240 ggccccgggt ctgaggctgc ggcgttcggc tccaacggcc tgggggttt ccccccactc      300 aacagcgtgt ctccgagccc gctgatgcta ctgcacccgc cgccgcagct gtcgcctttc     360
ctgcagcccc acgccagca gtgcccctac tacctggaga cgagcccag cggctacacg       420 gtgcgcgagg ccggcccgcc ggcattctac aggccaaatt cagataatcg acgccagggt    480
ggcagagaaa gattggccag taccaatgac aagggaagta tggctatgga atctgccaag    540
gagactcgct actgtgcagt gtgcaatgac tatgcttcag gctaccatta tggagtctgg     600
tcctgttggg gctgcaaggc cttcttcaag agatctattg caggaggtaa cgactatatg     660
tgtccagcca ccaaccagtg caccattgat aaaaacagga ggaagagctg ccaggcctgc    720
cggctccgca atgctacga agtgggaatg atgaaggtg ggatacgaaa agaccgaaga      780
ggagggagaa tgttgaaaca caagcgccag agagatgatg ggagggcag gggtgaagtg     840 gggtctgctg gagacatgag agctgccaac ctttggccaa gcccgctcat gatcaaacgc    900
tctaagaaga acagcctggc cttgtccctg acggccgacc agatggtcag tgccttgttg    960
gatgctgagc cccccatact ctattccgag tatgatccta ccagaccctt cagtgaagct   1020
tcgatgatgg gcttactgac caacctggca gacagggagc tggttcacat gatcaactgg   1080
gcgaagaggg tgccaggctt tgtggatttg accctccatg atcaggtcca ccttctagaa   1140
tgtgcctggc tagagatcct gatgattggt ctcgtctggc gctccatgga gcacccagtg   1200
aagctactgt ttgctcctaa cttgctcttg gacaggaacc agggaaaatg tgtagagggc   1260
atggtggaga tcttcgacat gctgctggct acatcatctc ggttccgcat gatgaatctg   1320
cagggagagg agtttgtgtg cctcaaatct attattttgc ttaattctgg agtgtacaca   1380
tttctgtcca gcaccctgaa gtctctggaa gagaaggacc atatccaccg agtcctggac   1440
aagatcacag acactttgat ccacctgatg gccaaggcag gcctgaccct gcagcagcag   1500
caccagcggc tggcccagct cctcctcatc ctctcccaca tcaggcacat gagtaacaaa   1560
```

| | | |
|---|---|---|
| ggcatggagc atctgtacag catgaagtgc aagaacgtgg tgcccctcta tgacctgctg | 1620 | |
| ctggagatgc tggacgccca ccgcctacat gcgcccacta gccgtggagg ggcatccgtg | 1680 | |
| gaggagacgg accaaagcca cttggccact gcgggctcta cttcatcgca ttccttgcaa | 1740 | |
| aagtattaca tcacggggga ggcagagggt ttccctgcca cagtcggtac cacggccccc | 1800 | |
| ccgaccgatg tcagcctggg ggacgagctc cacttagacg gcgaggacgt ggcgatggcg | 1860 | |
| catgccgacg cgctagacga tttcgatctg gacatgttgg gggacgggga ttccccgggt | 1920 | |
| ccgggattta ccccccacga ctccgccccc tacggcgctc tggatatggc cgacttcgag | 1980 | |
| tttgagcaga tgtttaccga tgcccttgga attgacgagt acggtggg | 2028 | |

<210> SEQ ID NO 73
<211> LENGTH: 676
<212> TYPE: PRT
<213> ORGANISM: Artificial sequence
<220> FEATURE:
<223> OTHER INFORMATION: fusion polypeptide

<400> SEQUENCE: 73

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Trp Gly Cys Lys Ala Phe
            195                 200                 205

Phe Lys Arg Ser Ile Ala Gly Gly Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285
```

```
Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
    435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
    515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Gly Thr Thr Ala Pro Pro Thr Asp Val Ser Leu Gly Asp
    595                 600                 605

Glu Leu His Leu Asp Gly Glu Asp Val Ala Met Ala His Ala Asp Ala
610                 615                 620

Leu Asp Asp Phe Asp Leu Asp Met Leu Gly Asp Gly Asp Ser Pro Gly
625                 630                 635                 640

Pro Gly Phe Thr Pro His Asp Ser Ala Pro Tyr Gly Ala Leu Asp Met
                645                 650                 655

Ala Asp Phe Glu Phe Glu Gln Met Phe Thr Asp Ala Leu Gly Ile Asp
            660                 665                 670

Glu Tyr Gly Gly
        675

<210> SEQ ID NO 74
<211> LENGTH: 15
<212> TYPE: DNA
```

```
<213> ORGANISM: Artificial sequence
<220> FEATURE:
<223> OTHER INFORMATION: construct

<400> SEQUENCE: 74
aggtcactgt ggccc                                                    15

<210> SEQ ID NO 75
<211> LENGTH: 15
<212> TYPE: DNA
<213> ORGANISM: Artificial sequence
<220> FEATURE:
<223> OTHER INFORMATION: construct

<400> SEQUENCE: 75
gggccactgt ggccc                                                    15

<210> SEQ ID NO 76
<211> LENGTH: 64
<212> TYPE: DNA
<213> ORGANISM: Artificial sequence
<220> FEATURE:
<223> OTHER INFORMATION: construct

<400> SEQUENCE: 76
aagcttaggt cactgtgacc tatcaagata tcgagatagg tcactgtgac ctatcgactc    60
taga                                                                64

<210> SEQ ID NO 77
<211> LENGTH: 64
<212> TYPE: DNA
<213> ORGANISM: Artificial sequence
<220> FEATURE:
<223> OTHER INFORMATION: construct

<400> SEQUENCE: 77
aagcttaggt cactgtggcc catcaagata tcgagatagg tcactgtggc ccatcgactc    60
taga                                                                64

<210> SEQ ID NO 78
<211> LENGTH: 64
<212> TYPE: DNA
<213> ORGANISM: Artificial sequence
<220> FEATURE:
<223> OTHER INFORMATION: construct

<400> SEQUENCE: 78
aagcttgggc cactgtggcc catcaagata tcgagatggg ccactgtggc ccatcgactc    60
taga                                                                64

<210> SEQ ID NO 79
<211> LENGTH: 126
<212> TYPE: DNA
<213> ORGANISM: Artificial sequence
<220> FEATURE:
<223> OTHER INFORMATION: construct

<400> SEQUENCE: 79
aagcttaggt cactgtgacc tatcaagata tcgagatagg tcactgtgac ctatcgacag    60
gaattcacag gtcactgtga cctatcaaga tatcgagata ggtcactgtg acctatcgac   120
tctaga                                                             126
```

-continued

```
<210> SEQ ID NO 80
<211> LENGTH: 126
<212> TYPE: DNA
<213> ORGANISM: Artificial sequence
<220> FEATURE:
<223> OTHER INFORMATION: construct

<400> SEQUENCE: 80
aagcttgggc cactgtggcc catcaagata tcgagatggg ccactgtggc ccatcgacag     60
gaattcacgg gccactgtgg cccatcaaga tatcgagatg ggccactgtg gcccatcgac    120
tctaga                                                                126

<210> SEQ ID NO 81
<211> LENGTH: 250
<212> TYPE: DNA
<213> ORGANISM: Artificial sequence
<220> FEATURE:
<223> OTHER INFORMATION: construct

<400> SEQUENCE: 81
gctagcaggt cactgtgacc ttgacaacta gtaagtcagg tcactgtgac ctgacgtact     60
atctcgagag gtcactgtga ccttagagct gcaggtatca ggtcactgtg accttagttc    120
attaaagctt aggtcactgt gacctatcaa gatatcgaga taggtcactg tgacctatcg    180
acaggaattc acaggtcact gtgacctatc aagatatcga gataggtcac tgtgacctat    240
cgactctaga                                                           250

<210> SEQ ID NO 82
<211> LENGTH: 250
<212> TYPE: DNA
<213> ORGANISM: Artificial sequence
<220> FEATURE:
<223> OTHER INFORMATION: construct

<400> SEQUENCE: 82
gctagcgggc cactgtggcc ctgacaacta gtaagtcggg ccactgtggc ccgacgtact     60
atctcgaggg gccactgtgg ccctagagct gcaggtatcg ggccactgtg gccctagttc    120
attaaagctt gggccactgt ggcccatcaa gatatcgaga tgggccactg tgcccatcg    180 acaggaattc acgggccact gtggcccatc aagatatcga gatgggccac tgtggcccat    240
cgactctaga                                                           250

<210> SEQ ID NO 83
<211> LENGTH: 15
<212> TYPE: DNA
<213> ORGANISM: Artificial sequence
<220> FEATURE:
<223> OTHER INFORMATION: consensus sequence

<400> SEQUENCE: 83
aggtcactgt gacct                                                      15
```

TAMOXIFEN AND 4-HYDROXYTAMOXIFEN-ACTIVATED SYSTEM FOR REGULATED PRODUCTION OF PROTEINS IN EUKARYOTIC CELLS

FEDERALLY SPONSORED RESEARCH OR DEVELOPMENT

The subject matter of this application was in part funded by the National Institutes of Health (Grant Nos. RO1 HD-16720 and RO1 CA-60514). The US government may have certain rights in this invention.

BACKGROUND OF THE INVENTION

As a light switch can provide instant illumination (ON) or sudden darkness (OFF), so, too, can gene expression systems provide a gene product at will. Such regulated gene expression systems, wherein specific promoters and regulatory elements that play the role of a light switch are functionally-linked to a gene of interest, are important tools that facilitate gene function studies and enable exogenous control in gene therapies. While endogenous gene expression is tightly regulated, being turned ON and OFF according to developmental state, extracellular and intracellular cues and environmental signals, exogenous gene expression has most often been accomplished by constitutive expression (the light is always ON) wherein transcription is controlled from an unregulated, strong promoter sequence. However, such expression can result in over-expression, temporal mis-expression and cell lethality; hampering gene function studies and gene therapy interventions, and even rendering them ineffective. Although today, regulated (inducible) gene expression systems are readily available, they often suffer from high basal expression (even OFF, the light still flickers), low protein synthesis (the light bulb is dimly illuminated) and over-riding cellular circuits (factors) that interfere with the intended molecular switch. In many cases, the agent that flips the switch itself often exerts pleiotropic effects, becomes ineffective over time, or the safety of its administration to an organism or cell is unknown.

To obviate these and other difficulties, inducible expression systems have been developed. Such systems subjugate the gene(s) of interest under the control of an "inducible" promoter—that is, a promoter to which transcription factors, etc., can be made to bind at will, using exogenous factors such as metals, temperature, hormones, or other polypeptides provided in trans. However, most inducible systems are not completely "turned off" in the absence of the inducer—low levels of basal expression are often observed. Such basal expression reduces the advantages of an inducible expression when the gene to be induced is lethal to the target cell (Ausubel et al., 1987). Desirable characteristics of inducible gene expression systems are presented in Table 1.

TABLE 1

Desirable characteristics of inducible expression systems[1]

| Element | Desirable characteristics |
| --- | --- |
| Basal (uninduced) expression | Very low to none of operably-linked sequence |
| Inducibility | High inducibility and specificity |
| | High inducer specificity |
| | High response dynamic range with respect to inducer concentrations |
| | Quick response to inducer |
| | Rapid switch-off after removing inducer |
| Inducing agent | Non-toxic to preferably the organism, or at least target tissues and cells |
| | Inducer exerts no other physiological effects |
| | Inducer is absent from target tissues and cells |
| | Inducer is appropriate for use in cell culture, animal models and humans |

[1]Adapted from (Zuo and Chua, 2000).

Common eukaryotic (or adaptable to eukarayotes) inducible expression systems, their characteristics, advantages and disadvantages are presented in Table 2.

TABLE 2

Common eukaryotic inducible gene expression systems[2]

| System | Induction ratio (fold induction) | Advantages | Disadvantages | References |
| --- | --- | --- | --- | --- |
| Heat shock | 4–10 | 1. Inducing agent readily available and inexpensive, 2. Very fast induction kinetics (1 h). | 1. Many pleiotropic effects. 2. Limited utility in mammalian systems. 3. First reported to likely have low leakiness; however, due to low induction, more likely that leakiness is high. | (Kothary et al., 1989) |
| Heavy metal ions | 5–10 | 1. Fast induction kinetics (16 h). | 1. Many pleiotropic effects. 2. High leakiness. | (Filmus et al., 1992) |
| Interferon | 2–50 | 1. Low leakiness. | 1. Slow induction kinetics (3–4 days). 2. Function dependent on cell type. 3. Induction causes many pleiotropic effects. | (Kuhn et al., 1995) |
| FK506 dimer | 0–1.5 | 1. Very fast kinetics (16 h). 2. Very low leakiness. 3. Few pleiotropic effects. | 1. Limited usefulness; mostly in vitro to activate endogenous signaling pathways. | (Belshaw et al., 1996) |
| Steroid hormone | 0–200 | 1. Fast induction kinetics (24 h). | 1. High leakiness, 2. Many pleiotropic effects. 3. In vivo utility unknown. | (Kuo et al., 1994) |
| Gal4-Er | 0–100 | 1. Very fast induction kinetics (1–2 h). 2. Low leakiness. 3. No pleiotropic effects. | 1. In vivo utility unknown. | (Braselmann et al., 1993) |

TABLE 2-continued

Common eukaryotic inducible gene expression systems[2]

| System | Induction ratio (fold induction) | Advantages | Disadvantages | References |
|---|---|---|---|---|
| Progesterone antagonist/ RU486 | 10–50 | 1. Fast induction kinetics (10 h, in vitro). 2. Low leakiness 3. Few pleiotropic effects in most subjects. 4. Receptor is endogenous to many subjects 5. Inducer is readily available and commonly used | 1. RU486 is unspecific for progesterone receptors. 2. Not an ideal induction agent, especially for potentially-pregnant/ pregnant subjects. 3. Lower induction. 4. Receptors are not expressed by every cell types; limited tissue distribution. | (Wang et al., 1994) |
| Mutant estrogen receptor | unknown | 1. Low leakiness. 2. Few pleiotropic effects in most subjects. | 1. Slow induction kinetics (3–4 days). | (Zhang et al., 1996) |
| Ecdysone | $0-10^4$ | 1. Ecdysone is not produced by most sublects. 2. Fast induction kinetics (20 h). 3. Very low leakiness, 4. No pleiotropic effects, | 1. Low polypeptide production. 2. Effects of ecdysone (or synthetic analogues) on mammalian physiology over time are unknown. | (No et al., 1996) |
| Tetracycline | $1000-10^5$ | 1. Tetracycline is not endogenous to subjects 2. Tetracycline is readily available and commonly used 3. Low leakiness 4. Induction occurs upon the introduction of tetracycline— thus eliminating continuous tetracycline administration (in the version that is OFF in the absence of tetracycline). | 1. Higher basal expression of operably-linked subcloned nucleic acid 2. Tetracycline is continuously administered to a cell or subject (in the version that is OFF in the presence of tetracycline) 3. tetracycline has undesirable side effects, such as squelching non-specifically gene expression. 4. In cultured cells, tetracycline is difficult to wash out and thus it is difficult to synchronize polypeptide production 5. Unreliable; does not always work. | (Gossen et al., 1995) |
| lac repressor-based | 5–1000 | 1. Fast induction kinetics (12–24 h) 2. IPTG inducing agent is not produced in subjects. 3. IPTG is easily available. | 1. Induced expression is commonly limited to only 40 to 50-fold 2. IPTG can exert cytotoxic effects. 3. Unreliable; moderate success. 4. High leakiness. | (Baim et al., 1991) |

Heat Shock

The initial constructs took advantage of the *D. melanogaster* hsp70 promoter that relied on the highly conserved endogenous heat shock transcription factors for binding upon heat shock. Upon transfer from physiological to elevated temperatures in transient transfections, induction was rapid, subsided after cells were returned to physiological temperatures, and basal expression was low (Schweinfest et al., 1988). An in vivo vector was also constructed for transgenic mice, although induction was non-uniform throughout analyzed embryos, most likely due to uneven access of the induction agent (heat) to the different parts of the animal, as well as tissue differences in the ability to respond to heat shock stress (Kothary et al., 1989). However, heat shock inducible systems are best suited for short-term studies, since subjects will pleiotropically respond to heat shock (Gingrich and Roder, 1998).

Heavy Metal Ions

These systems exploit the regulatory elements of metallothionein genes; the most useful heavy metal ions being zinc ($Zn^{2+}$) and cadmium ($Cd^{2+}$). These systems comprise metal responsive elements within metallothionein gene promoters that are bound by metal-activated factors. Because metallothionein promoters are also recognized by constitutively expressed transcription factors and are also sensitive to glucocorticoids, progesterone, interleukin-5 and interferon, basal expression levels are high; consequently, induction is often low (Gingrich and Roder, 1998). To improve their usefulness, these promoters are combined with other inducible elements, often with other transcription factor-sensitive regions deleted, resulting in synergistic induction (Filmus et al., 1992). For example, melding of a metal-sensitive promoter region with that of a dexamethasone region results in 65-fold induction, while either the metal ion or dexamethasone gave less than 10% of those levels by themselves. However, in addition to high basal expression levels, heavy metals are toxic over time to mammalian subjects, limiting these system's usefulness.

Interferon

Interferon is produced in response to viral infection, double stranded RNA, mycoplasma, bacteria, endotoxin and antigens (David, 1995). When interferon cell surface receptors are liganded, signaling pathways are activated that result in the binding of transcription factors to interferon stimulated response elements in the promoter regions of interferon-sensitive genes. However, because many genes are interferon-sensitive and mammals constitutively express low levels of interferon, using interferon stimulated response elements results in uneven expression, even between genetically identical organisms and exerts pleiotropic effects. Constitutive high levels of interferon may also be adverse to a subject (Gingrich and Roder, 1998).

Specific Induction of Signaling Pathways (e.g., FK506 Dimer)

In this system, controlled gene expression is mediated by activating specific signal transduction pathways. Signaling is induced by a lipid-soluble synthetic ligand that promotes the oligomerization (cross-linking) of cell surface receptors that lack transmembrane and extracellular regions. This signaling then promotes specific transcription factors to bind to their promoter regions, inducing gene expression. The prototype of this system was first performed using a dimer of the synthetic ligand FK506, specific for immunophilin FKBP12. NFAT-responsive promoter regions, once bound by NFAT transcription factor, promote gene expression (Spencer et al., 1993). However, while useful for investigating signal transduction pathways, this approach has limited usefulness for specific inducible gene expression, since such transduction pathways usefully affect many other genes in addition to the target (Gingrich and Roder, 1998).

Steroid-based Inducible Expression Systems

Glucocorticoid (Glucocorticoid Responsive Elements)

Glucocorticoid-induced expression systems take advantage of glucocorticoid responsive elements found in various promoters. While some improvements have been made—such as combining glucocorticoid responsive elements with other inducible systems, such as heavy metals, combining with tissue-specific promoters, modified ligands/receptors, etc.—these systems are fraught with high basal expression and the possibility for many pleiotropic effects.

Gal4-Estrogen Receptor

This system uses a fusion protein of yeast Gal4 (DNA binding domain) and mammalian estrogen receptor hormone-binding domain (Braselmann et al., 1993). This system is more selective than most: no mammalian cells express Gal4 and few express estrogen receptors in vitro (although in vivo, many tissues do). Target genes are operably-linked to Gal4-binding sites, preferably artificial ones such that basal expression is low. Upon estrogen administration, the fusion receptor binds estrogen and then binds to the Gal4 binding sites, initiating transcription. Because estrogen receptors exhibit cell-type specificity due to two monacidic transactivation functions (TAF-1 and -2), the Herpes simplex virus virion protein 16 acidic activation domain (VP16; a strong activator (Triezenberg et al., 1988)) was added to the fusion protein, thus increasing transcription. Even though the VP16 fusion results in good (100-fold) induction; the system is unattractive in that estrogen has many non-specific effects.

Mutant Progestrone Receptor

In this system, a 42 amino acid C-terminal deletion mutant of the human progesterone receptor that poorly binds progesterone but does bind RU486 (Mifepristone) and other progesterone receptor antagonists, is exploited. Fused with the VP16 activation domain, this chimeric protein can induce expression from those sequences operably-linked to Gal4 DNA binding domains. While exhibiting fast induction, only modest expression is observed. While the RU486 doses sufficient for induction are modest and less than that required for anti-progesterone activity and in vivo efficacy (Wang et al., 1994), the long-term effects of chronic RU486 administration at these doses causes concern. Induction is high, basal expression is moderate and the system is suitable for gene therapy because RU-486 is a human pharmaceutical. The main disadvantage lies in the use of a progesterone receptor mutant that activates many cellular genes usually regulated by progesterone receptors.

Mutant Estrogen Receptor

These systems are based on mutant estrogen receptors that bind the anti-estrogen pharmaceuticals tamoxifen or 4-hydroxytamoxifen, but not estrogen (17β-estradiol) (Zhang et al., 1996). Fusing the mutant estrogen receptor to Cre recombinase and assaying the ability to mediate lox-based recombination demonstrated efficacy of this system. High tamoxifen doses induced recombination, although even slightly higher doses were cytotoxic. Over time, the basal activity of this chimeric protein increased; however, fusing the mutant estrogen receptor to the fusion protein termini reduced basal activity levels. However, this system has not been useful for inducing expression from an operably-linked polynucleotide to estrogen receptor DNA binding domains. These Cre-estrogen receptor chimeras are useful for producing knockout and transgenic mice but are not used for the production of recombinant polypeptides in cultured cells.

Ecdysone

Ecdysone, an insect steroid, triggers morphological changes in *D. melanogaster*. To mediate ecdysone activity, ecdysone receptors form heterodimers with an insect homolog of vertebrate retinoid X receptor (RXR), ultraspiricle. Ecdysone's effects are exerted even if ultraspiricle is replaced with the human ultraspiricle homolog, RXR, in mammalian cells. An optimized ecdysone promoter is operably linked to a polynucleotide of interest, and a modified ecdysone receptor (fused with VP16) is expressed. Ecdysone (or muristerone) induction results in liganded ecdysone receptors, which then bind to the promoter, inducing expression. In short-term studies, mice did not exhibit side effects from muristerone administration (No et al., 1996). Generally, induction is very high, basal expression levels are low; however, protein synthesis is also low. Because the system uses a synthetic hormone related to those seen in fruit flies, this system may not be suitable for human gene therapy applications if, for example, muristerone engenders pleiotropic effects.

Prokaryote-based Inducible Systems

*E. coli* lac Repressor

When bound to lac operator DNA sequences, lac repressor inhibits transcription of operably-linked polynucleotide sequences. When bound to lactose or non-metabolizable isopropyl-β-D-thiogalactopyranoside (IPTG), the lac repressor releases the operator sequences, thus allowing transcription to proceed. Adding lac operator sites near the TATA-box or promoter start sites enables the operably-linked polynucleotides to be regulated by lac repressor in eukaryotes.

Because lac operator/lac repressor complexes also efficiently terminate transcription, lac operator site(s) inserted downstream of an operably-linked promoter can also be used to manipulate gene expression (Deuschle et al., 1990).

In another version, lac repressor is fused to VP16, and operator sites are operably-linked upstream of a minimal promoter. The lac repressor was converted to a mammalian transcriptional activator by adding a nuclear localization signal and VP16. IPTG or lactose thus do not induce expression, but silence it. While induction levels are high, chronic administration of IPTG reduces precise control of gene expression (Labow et al., 1990). The reverse of this system was created, although in to this instance, lac repressor binding to operator sites was found to be heat-sensitive (Baim et al., 1991). Other attempted improvements resulted in various problems (Gingrich and Roder, 1998).

Tetracycline

Currently this system is the most popular for controlling exogenous gene expression in many types of cultured cells. Fusing *E. coli* tet repressor with VP16 creates a tetracycline-controlled transactivator that in the presence of tetracycline or derivatives, can induce expression from polynucleotides operably linked to tet operators (Gossen et al., 1995); this approach was an improvement on an earlier one that lacked the VP16 fusion, wherein tetracycline is chronically administered to silence expression; removal of tetracycline induces expression. However, sufficient tet repression levels could not be consistently obtained (Gossen and Bujard, 1992). While the system exhibits desirable characteristics, it suffers from the problems of clearing tetracycline and derivatives from cells (Gingrich and Roder, 1998). In general, fold induction is good and the expression level is high.

While many inducible expression systems are available, systems that incorporate and exhibit the largest number of desirable characteristics (Table 1) and overcome the majority of limitations of current systems will give the medical and research fields excellent tools to treat (via gene therapy, for example) and discover basic biological mechanisms in development, cell biology and molecular biology.

SUMMARY

In a first aspect, the invention provides for polynucleotides of SEQ ID NOS: 3, 5, 7, 9, 11, 13, 15, 17, 19, 21, 23, 75, 78, 80 and 82, or complements thereof.

In a second aspect, the invention provides for polynucleotides having at least more than 80% sequence identity to the sequences of SEQ ID NOS: 3, 5, 7, 9, 11, 13, 15, 17, 19, 21, 23, 75, 78, 80 and 82, or complements thereof.

In a third aspect, the invention is drawn to vectors containing a sequence of SEQ ID NOS: 3, 5, 7, 9, 11, 13, 15, 17, 19, 21 or 23, or complement thereof,or containing a sequence of SEQ ID NOS: 75, 78, 80 or 82, or complement thereof. The vector may also have any combination of SEQ ID NOS: 3, 5, 7, 9, 11, 13, 15, 17, 19, 21, 23, 75, 78, 80 or 82, or complement thereof.

In a fourth aspect, the invention provides for vectors, having at least one copy of a first sequence of SEQ ID NOS: 3, 5, 7, 9, 11, 13, 15, 17, 19, 21 or 23, or complement thereof, and at least one copy of a second sequence of SEQ ID NOS: 75, 78, 80 or82.

In a fifth aspect, the invention provides for polynucleotides having a first polynucleotide of SEQ ID NOS: 75, 78, 80 or 82 that is operably linked to a second polynucleotide. This second polynucleotide may encode, for example, a therapeutic polypeptide or an antibody. Alternatively, the second polynucleotide may be an antisense polynucleotide.

In a sixth aspect, the invention is drawn to polypeptides encoded by SEQ ID NOS: 3, 5, 7, 9, 11, 13, 15, 17, 19, 21 and 23.

In a seventh aspect, the invention provides for polypeptides of SEQ ID NOS: 4, 6, 8, 10, 12, 14, 16, 18, 22 and 24.

In an eighth aspect, the invention provides for polypeptides having at least 80% sequence identity to SEQ ID NOS: 4, 6, 8, 10, 12, 14, 16, 18, 22 or 24.

In a ninth aspect, the invention provides for polypeptides containing a first polypeptide having a VP16 domain fused to a second polypeptide SEQ ID NO:4, 6, 8, 10, 12, 14, 16, 18, 22 or 24. The VP16 domain may have 79 or 129 amino acids of VP16, and the domain may be at the amino- or carboxy terminus of the fusion polypeptides. Alternatively, the VP16 domains may be internally fused to the second polypeptide. In a tenth aspect, the invention is drawn to polynucleotides encoding such fusion proteins and polypeptides, such as SEQ ID NOS: 66, 68, 70 or 72.

In an eleventh aspect, the invention provides polynucleotides having at least 80% sequence identity to SEQ ID NO:66, 68, 70 or 72.

In a twelfth aspect, the invention is drawn to polypeptides of SEQ ID NOS: 67, 69, 71 or 73.

In a thirteenth aspect, the invention is drawn to polypeptides having at least 80% sequence identity to SEQ ID NOS: 67, 69, 71 or 73.

In a fourteenth aspect, the invention provides inducible expression systems, having a first polynucleotide, such as SEQ ID NOS: 3, 5, 7, 9, 11, 13, 15, 17, 19, 21, 23, 66, 68, 70 or 72, or complement thereof; and containing a second polynucleotide of SEQ ID NOS: 75, 78, 80 or 82, or complement thereof. The system may be made up of two vectors, one vector containing the first polynucleotide; the other vector, the second polynucleotide; or a single vector may contain both polynucleotides.

In a fifteenth aspect, the invention is drawn to kits having at least one copy of a first polynucleotide, such as SEQ ID NOS: 3, 5, 7, 9, 11, 13, 15, 17, 19, 21, 23, 66, 68, 70 or 72, or complement thereof; and at least one copy of a second polynucleotide of SEQ ID NOS: 75, 78, 80 or 82, or complement thereof. The kit may also contain additional components, such as tamoxifen, 4-hydroxytamoxifen or moxestrol, or a combination of these. Furthermore, its may also include repressing agents to repress induction, such as an antiestrogen compounds, e.g., ICI 182, 780.

In a sixteenth aspect, the invention provides methods of inducing gene expression in a subject by administering to the subject at least one copy of a first polynucleotide of SEQ ID NOS: 3, 5, 7, 9, 11, 13, 15, 17, 19, 21, 23, 66, 68, 70 or 72 or complement thereof, and administering to the subject at least one copy of a second polynucleotide of SEQ ID NOS: 75, 78, 80 or 82, or complement thereof, that is operably linked to the gene. The inducing agent may be tamoxifen, 4-hydroxytamoxifen or moxestrol. Gene expression may be silenced by administering to the subject a repressing agent, such as an anti-estrogen compound, including ICI 182,780. The first and second polynucleotide can be provided as a single polynucleotide.

In an seventeenth aspect, the invention provides methods of inhibiting endogenous gene expression in a subject, by administering to the subject a first polynucleotide of SEQ ID NOS: 3, 5, 7, 9, 11, 13, 15, 17, 19, 21, 23, 66, 68, 70 or 72, or complement thereof, and administering to the subject a second polynucleotide of SEQ ID NOS: 75, 78, 80 or 82 or complement thereof, wherein said second polynucleotide is operably linked to a third polynucleotide, such that upon induction with an inducing agent, said third polynucleotide is transcribed in an anti-sense orientation to the sequence of the endogenous gene.

In an eighteenth aspect, the invention is drawn to non-human transgenic animals, containing a first polynucleotide of SEQ ID NOS: 3, 5, 7, 9, 11, 13, 15, 17, 19, 21, 23, 66, 68, 70 or 72, or complement thereof, and a second polynucleotide of SEQ ID NOS: 75, 78, 80 or 82, or complement thereof.

In a nineteenth aspect, the invention provides cells having a first polynucleotide of SEQ ID NOS: 3, 5, 7, 9, 11, 13, 15, 17, 19, 21, 23, 66, 68, 70 or 72, or complement thereof; and a second polynucleotide of SEQ ID NOS: 75, 78, 80 or 82, or complement thereof.

DESCRIPTION OF THE DRAWINGS

FIG. 1B shows electrophoretic mobility shift assays (EMSAs) of the binding of various ERs to the cERE probe. (i) shows the relative amount of each ER used in each assay and a typical gel, (ii) shows graphically the percent of the cERE probe that was shifted. FIG. 1C shows EMSAs for various ERs binding to the pS2 ERE probe. (i) shows the relative amount of each ER used in each assay and a typical gel, and (ii) shows graphically the percent of the pS2 ERE probe that was shifted. FIG. 1D shows EMSAs for various ERs binding to the pS2 PAL probe. (i) shows 2, 4 and 8 µg and (ii) 15 µg of various ERs in each assay and typical gels, (iii) shows graphically the percent of the pS2 PAL probe that was shifted.

FIG. 3D presents a graphical summary of the ratio of OHT/MOX transactivation for each reporter.

FIG. 4A shows that OHT is a weak agonist on the ATL4/cERE-LUC reporter; however, when four copies of pS2 PAL are operably-linked to the reporter gene (ATL4/PAL-LUC, FIG. 4B), OHT is a potent agonist. FIG. 4C shows that on ATL8/PAL-LUC, with wild-type ER, OHT is a stronger agonist than MOX, while on ATL8/cERE-LUC, OHT is a weaker one.

DETAILED DESCRIPTION

Figure 1:
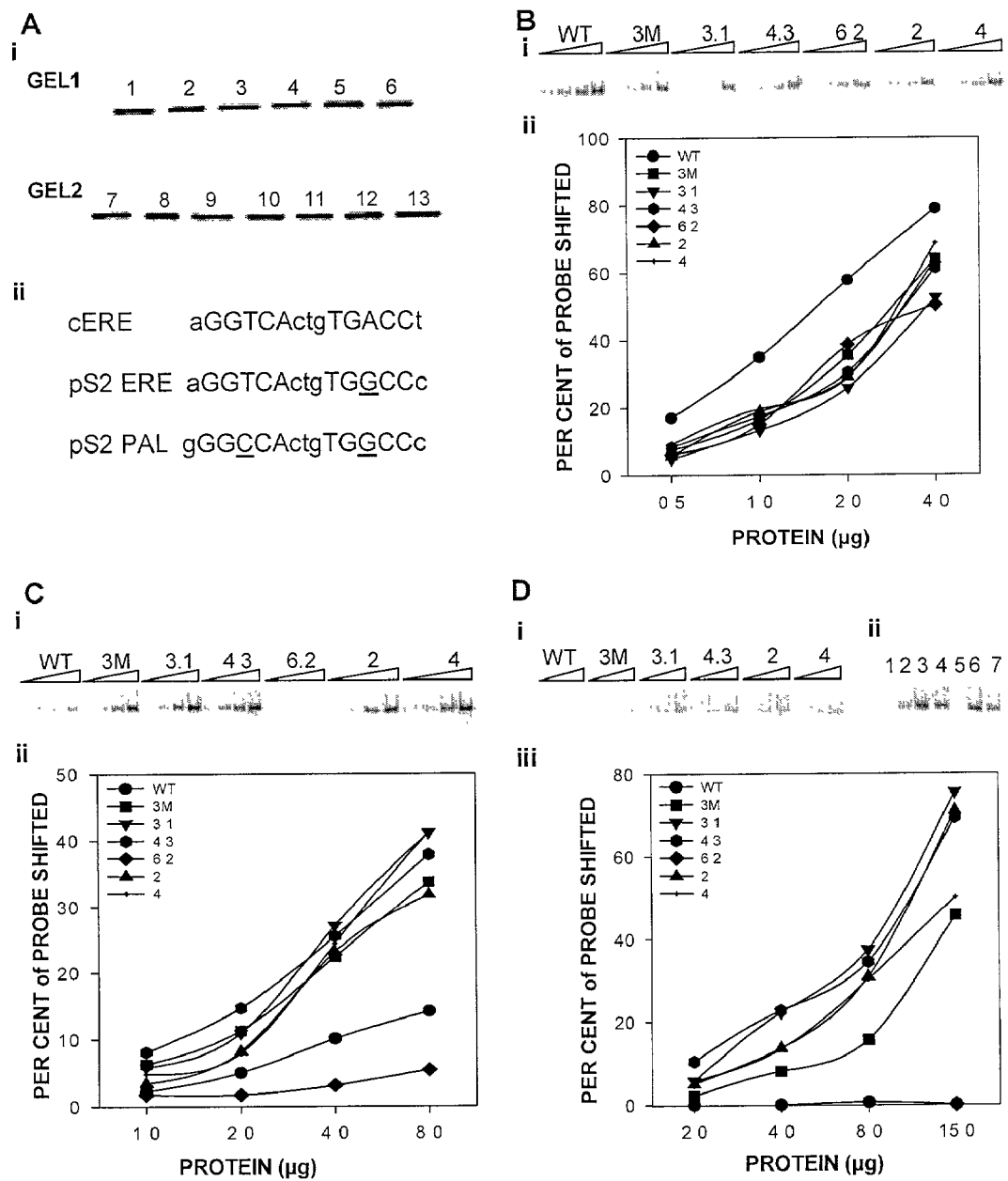
FIGS. 1A–1D, FIG. 1A shows Western blots of wild-type ERα and ER mutants from extracts of transiently transfected CHO-S cells and sequences for the cERE (SEQ ID NO: 83), pS2 ERE (SEQ ID NO: 74) and pS2 PAL (SEQ ID NO: 75).

To solve the problem of precise expression of exogenous genes, an inducible system that is activated by tamoxifen and its active metabolite, 4-hydroxytamoxifen (OHT) was developed. This system is based on a novel DNA sequence that is activated on binding of tamoxifen or OHT bound to estrogen receptors. The stringency and level of induction is greatly increased by mutations in the DNA binding domain of estrogen receptor that greatly increase binding of the protein to the DNA sequence. Induction is highly manifold, expression levels are moderate to high (depending on the variation), a small molecule ligand can rapidly turn the system off, and most importantly, endogenous estrogen receptors do not activate the plasmid encoding the recombinant protein. This system is especially attractive in gene therapy applications.

The inducible system of the invention (TAS, for tamoxifen activated system) comprises three versions with different characteristics. This toolbox allows a user to choose the TAS that is most appropriate for a specific application. One version ("A") is suitable for work requiring tight regulation and moderate polypeptide synthesis. Another version ("B1") is ideal for applications requiring the highest level of inducibility and moderate polypeptide synthesis; this version has the widest range of application. For those applications requiring the highest level of polypeptide synthesis but only moderate induction, another version ("B2") is appropriate.

The TAS includes:
1. Mutant estrogen receptors (ERs) and chimeras thereof,
2. Polynucleotide (DNA) sequences, which are mutant sequences related to estrogen response elements (EREs), providing at least one high-affinity binding site for the mutant estrogen receptors,
3. Agonists, such as tamoxifen and OHT, when bound by a mutant or chimeric ER activates transcription, and.
4. Antagonists, such as ICI 182,780, that turn off transcription by the OHT- or tamoxifen-activated mutant or chimeric ER
5. A variation of the invention includes expression plasmids using mutant EREs to which wild-type estrogen receptor may bind and moderately activate transcription.

The TAS's significantly differ from the previously described mutant estrogen systems (such as that used to control Cre recombinase activity (Zhang et al., 1996)). The ERs of the invention are mutated at the DNA binding domain (DBD), retaining estrogen ligation; previous ER mutants were mutated at the ligand binding domain (LBD) and were designed to bind tamoxifen, but not estrogens; the DBDs remained wild-type. Additionally, this novel system incorporates mutated EREs that enhance mutant and chimeric ER binding, but are very poorly bound by wild-type ERs. The combination of these novel EREs and ER DBD mutations provides a powerful new regulated promoter system for selective, precise and robust control of gene expression (for example, 40- to 50-fold transcription activation). This system is also unique in that polypeptide production can be rapidly shut off by the addition of antagonists, such as ICI 182,780.

Applications

The key feature of the novel TAS's is that the mutant ERE DNA sequences communicate information to bound ERs, transforming the poor transcription activators tamoxifen and OHT to potent ones. The mutant ERs activate transcription from the novel EREs in response to tamoxifen and OHT concentrations below those used in breast cancer therapy. Tamoxifen has been used for over 20 years in treating and preventing breast cancer in human subjects; consequently, the risk profile for tamoxifen is well known. For gene therapy applications, the TAS's, requiring lower doses than therapeutic ones, render this system superior to other inducible systems requiring induction by less well-characterized inducing agents. Because the system can be rapidly activated and deactivated, discrete pulses of therapeutic agents may be administered.

The TAS's of the invention are useful for a large number of applications, including:

1. Production of bioactive, toxic, recombinant polypeptides in mammalian cells wherein chronic synthesis of these polypeptides would eventually result in cell death or aberrant cell functions.

2. Human gene therapy. In the TAS of the invention, tamoxifen effectuates transcription activation at concentrations well below those used to treat breast cancer. Plasmids that contain mutant EREs and allow wild-type ERs bound to tamoxifen or OHT to moderately bind and activate transcription are also useful. Such plasmids allow treatment of breast cancer cells expressing wild-type estrogen receptors using tamoxifen or OHT, activating toxic polypeptide synthesis, eliminating the cancer cells.

3. Biomedical and fundamental research. Regulated expression systems have diverse applications in modern biomedical and basic research. The TAS's of the invention are exceptionally useful for such studies because they can be quickly turned on and off at will.

4. Transgenic animals. To produce therapeutic models for human disease in which production or suppression of the protein of interest occurs at a specific time and in specified tissues, regulated promoter systems are critical.

Wild-Type Estrogen Receptors and DNA Binding Sites

Two ERs, ERα and ERβ, mediate estrogen signaling. Liganded ERs activate transcription either by binding specific DNA sequences, the EREs, or being tethered by ER to the DNA through other bound transcription factors, such as AP1 or SP1. Human ERα belongs to the steroid/nuclear receptor superfamily, characterized by conserved structures and characteristic functional organization. These structures include variable N-terminal domains, conserved zinc-finger DNA binding domains (DBDs), and C-terminal ligand binding domains (LBDs). The DNA binding domain recognizes specific DNA sequences. Transcription activation is mediated by the activation function AF-1 in the N-terminal A/B domain and the ligand-dependent activation function AF-2 in the ligand binding domain.

Potent estrogens, such as 17β-estradiol and poorly metabolized synthetic estrogens such as moxestrol (MOX), bind to ERs, freeing them from a complexes of heat shock proteins that prevent ERs from binding EREs. Upon binding and freeing from the heat shock complex, ER AF-2 changes conformation to recruit members of the p160 family of coactivators, as well as other coactivators such as the DRIP/TRAP/ARC/SMCC complex. These ER-coactivator complexes bind to histone acetyl transferases CBP/P300 and pCAF.

When wild-type and mutant ERs of the invention bind antiestrogens (also known as selective estrogen receptor modulators (SERMs)), such as tamoxifen and its active metabolite, 4-hydroxytamoxifen, the ERs weakly activate transcription. A novel synthetic ERE that is bound weakly by wild-type estrogen receptor was developed, as were new estrogen receptor mutants that bind these EREs. Tamoxifen and 4-hydroxytamoxifen are potent transcription activators only when bound to mutant ERs and mutant EREs (Version A). To further increase polypeptide synthesis, chimeric proteins having powerful transcription activation domain(s) are fused to ER mutants. Using the same promoter to express the chimeric receptors (Version B2) that was used in Version A, these chimeric receptors produce approximately ten times more protein. To reduce basal expression, an autoregulated system in which expression of the chimeric receptors is driven by an ATL8/PAL promoter was developed (Version B1). This system (Version B2) exhibits very low basal expression and can be used in a variety of cells. For most applications, Version B1 is preferred. Other antiestrogens, such as Raloxifene, bind mutant and chimeric estrogen receptors but fail to activate transcription. Because the potent antiestrogen ICI 182,780 exchanges with OHT or tamoxifen bound to the ER, addition of ICI 182,780 rapidly shuts off transcription by the TAS.

Tamoxifen (Tam) is widely used to treat and prevent breast cancer. When tamoxifen or its active metabolite 4-hydroxytamoxifen (OHT) are bound to the ER ligand binding domain (LBD), a protruding bulky side chain displaces helix 12 of the ER and occupies the binding cleft that serves to bind p160 coactivators, preventing transcription activation. Recent in vivo studies suggest that OHT-ER may recruit co-repressors to ERE-containing genes and thereby actively repressing their transcription (Shang et al., 2000; Shiau et al., 1998).

I. Embodiments

The following embodiments are given as examples of various ways to practice the invention. Many different versions will be immediately apparent to one of skill in the various arts to which this invention pertains.

Preferred Versions of TAS

The TAS's of the invention comprises three preferred versions, summarized in Table 3.

TABLE 3

Some preferred embodiments of the invention

| Version | Induction | Polypeptide synthesis | Basal (uninduced) expression |
|---|---|---|---|
| A | moderate | moderate | very low |
| B1 | high | high | very low |
| B2 | moderate | very high | moderate |

TAS Molecules

The novel TAS molecules of the invention include the nucleic acids whose sequences comprise those provided in Tables 5–15, 20, 22, 24, 26 and 29 or fragments thereof.

Mutant or variant TAS polynucleotides, any of whose bases may be changed from the corresponding base of the sequences shown in Tables 5–15, 20, 22, 24, 26 and 29 while still encoding a polypeptide that maintains an activity or a physiological function of the TAS polynucleotides or fragments are also useful. Furthermore, nucleic acids, or fragments, whose sequences are complementary to those shown in Tables 5–15, 20, 22, 24, 26 and 29, are also advantageous. The invention additionally includes nucleic acids or nucleic acid fragments, or their complements, whose structures include chemical modifications. Such modifications include modified bases, and modified or derivatized sugar phosphate backbones. These modifications may be carried out at least in part to enhance the chemical stability of a nucleic acid. In the mutant or variant nucleic acids, and their complements, up to 20% or more of the bases may be so changed.

The invention also includes polypeptides (shown in Table 17) and nucleotides (Tables 5–15, 20, 22, 24, 26 and 29) having 80–100%, including 81, 82, 83, 84, 85, 86, 87, 88, 89, 90, 91, 92, 93, 94, 95, 96, 97, 98 and 99%, sequence identity to the sequences presented in Tables 5–15, 20, 22, 24, 26 and 29, as well as nucleotides encoding any of these polypeptides (excluding DNA binding sites, such as EREs), and compliments of any of these nucleotides.

The novel TAS polypeptides of the invention include polypeptide fragments whose sequences comprise those provided in Tables 17, 21, 23, 25 and 27. The invention also includes TAS mutant or variant polypeptides, any residues of which may be changed from the corresponding residues shown in Tables 17, 21, 23, 25 and 27 while still encoding a polypeptide that maintains a native activity or physiological function, or a functional fragment thereof. In the mutant or variant TAS polypeptides, up to 20% or more of the residues may be so changed.

Mutant ERs

The mutant ERs suitable for use in the TAS's of the invention include the 11 shown in Tables 5–15 (only showing the first $Zn^{2+}$ finger region of the DBD region, nucleotides 607–654 of the wild-type ERα from which these mutants were derived is shown in Table 4 (the first $Zn^{2+}$ finger region of the DBD region is boldfaced). Understood is that the complete polynucleotide sequence for any of the ER mutants (SEQ ID NOS: 3, 5, 7, 9, 11, 13, 15, 17, 19, 21 and 23) would entail the substitution of the mutant sequence for nucleotides 607–654 in the wild-type sequence (SEQ ID NO: 1).

TABLE 4

Polynucleotide sequence of ERα (SEQ ID NO:1; Accession No. NM_000125)

| | | | | |
|---|---|---|---|---|
| atgaccatga | ccctccacac | caaagcatct | gggatggccc | tactgcatca gatccaaggg 60 |
| aacgagctgg | agccctgaa | ccgtccgcag | ctcaagatcc | ccctggagcg gccctgggc 120 |
| gagtgtacc | tggacagcag | caagcccgcc | gtgtacaact | accccgaggg cgccgcctac 180 |
| gagttcaacg | ccgcggccgc | cgccaacgcg | caggtctacg | gtcagaccgg cctccctac 240 |
| ggcccgggt | ctgaggctgc | ggcgttcggc | tccaacgcc | tgggggtttt cccccactc 300 |
| aacagcgtgt | ctccgagccc | gctgatgcta | ctgcacccgc | cgccgcagct gtcgccttc 360 |
| ctgcagcccc | acggccagca | ggtgccctac | tacctggaga | cgagcccag cggctacacg 420 |
| gtgcgcgagg | ccggcccgcc | ggcattctac | aggccaaatt | cagataatcg acgccagggt 480 |
| ggcagagaaa | gattggccag | taccaatgac | aagggaagta | tggctatgga atctgccaag 540 |
| gagactcgct | actgtgcagt | gtgcaatgac | tatgcttcag | gctaccatta tggagtctgg 600 |
| tcctgtgagg | gctgcaaggc | cttcttcaag | agaagtattc | aaggacataa cgactatatg 660 |
| tgtccagcca | ccaaccagtg | caccattgat | aaaaacagga | ggaagagctg ccaggcctgc 720 |
| cggctccgca | aatgctacga | agtgggaatg | atgaaaggtg | ggatacgaaa agaccgaaga 780 |
| ggagggagaa | tgttgaaaca | caagcgccag | agagatgatg | gggagggcag gggtgaagtg 840 |
| gggtctgctg | gagacatgag | agctgccaac | ctttggccaa | gcccgctcat gatcaaacgc 900 |
| tctaagaaga | acagcctggc | cttgtccctg | acggccgacc | agatggtcag tgccttgttg 960 |
| gatgctgagc | ccccatact | ctattccgag | tatgatccta | ccagaccctt cagtgaagct 1020 |
| tcgatgatgg | gcttactgac | caacctggca | gacagggagc | tggttcacat gatcaactgg 1080 |
| gcgaagaggg | tgccaggctt | tgtggatttg | accctccatg | atcaggtcca ccttctagaa 1140 |
| tgtgcctggc | tagagatcct | gatgattggt | ctcgtctggc | gctccatgga gcacccagtg 1200 |
| aagctactgt | ttgctcctaa | cttgctcttg | gacaggaacc | agggaaaatg tgtagagggc 1260 |
| atggtggaga | tcttcgacat | gctgctggct | acatcatctc | ggttccgcat gatgaatctg 1320 |
| cagggagagg | agtttgtgtg | cctcaaatct | attattttgc | ttaattctgg agtgtacaca 1380 |
| tttctgtcca | gcaccctgaa | gtctctggaa | gagaaggacc | atatccaccg agtcctggac 1440 |

TABLE 4-continued

Polynucleotide sequence of ERα (SEQ ID NO:1; Accession No. NM_000125)

| | | | | |
|---|---|---|---|---|
| aagatcacag | acactttgat | ccacctgatg | gccaaggcag gcctgaccct | gcagcagcag 1500 |
| caccagcggc | tggcccagct | cctcctcatc | ctctcccaca | tcaggcacat gagtaacaaa 1560 |
| ggcatggagc | atctgtacag | catgaagtgc | aagaacgtgg | tgcccctcta tgacctgctg 1620 |
| ctggagatgc | tggacgccca | ccgcctacat | gcgcccacta | gccgtggagg ggcatccgtg 1680 |
| gaggagacgg | accaaagcca | cttggccact | gcgggctcta | cttcatcgca ttccttgcaa 1740 |
| aagtattaca | tcacggggga | ggcagagggt | ttccctgcca | cagtc 1785 |

TABLE 5

Polynucleotide sequence of ER3M tggggctgca aggccttctt caagagatct attgcaggag gtaacgac 48 (SEQ ID NO:3)

TABLE 6

Polynucleotide sequence of ER3.1 tggggctgca aggccttctt caagagatct attaaccgac ataactcc 48 (SEQ ID NO:5)

TABLE 7

Polynucleotide sequence of ER4.3 tggggctgca aggccttctt caagagatct attgtacgac ctaccgac 48 (SEQ ID NO:7)

TABLE 8

Polynucleotide sequence of ER6.2 gagggctgca aggccttctt caagagaagt attgcaagac gtctcgac 48 (SEQ ID NO:9)

TABLE 9

Polynucleotide sequence of ER2 tggggctgca aggccttctt caagagatct attgcaagac ataacgac 48 (SEQ ID NO:11)

TABLE 10

Polynucleotide sequence of ER4 tggggctgca aggccttctt caagagatct attgcaagag gtaacgac 48 (SEQ ID NO:13)

TABLE 11

Polynucleotide sequence of ER2.1 tggagctgca aggccttctt caagagatct attgcaggag gtaacgac 48 (SEQ ID NO:15)

TABLE 12

Polynucleotide sequence of ER7.2 gagggctgca aggccttctt caagagaagt attcaaagac atccccgc 48 (SEQ ID NO:17)

TABLE 13

Polynucleotide sequence of ER15.3 gagagctgca aggccttctt caagagaagt attggaggac ataactac 48 (SEQ ID NO:19)

TABLE 14

Polynucleotide sequence of ER50.1 tggagctgca agggcttctt caagagatct aagcaaggac ataacgac 48 (SEQ ID NO:21)

TABLE 15

Polynucleotide sequence of ER57.1 tggagctgca agggcttctt caagagatct attaaaggag ttcccacc 48 (SEQ ID NO:23)

Table 16 shows the ERα polypeptide amino acid sequence encoded by SEQ ID NO: 1; 17, 21, 23, 25 and 27 shows a comparison between residues 203–219 of the various ER mutants (SEQ ID NOS: 4, 6, 8, 10, 12, 14, 16, 18, 20, 22 and 24) encoded by SEQ ID NOS: 3, 5, 7, 9, 11, 13, 15, 17, 19, 21, 23) and wild-type ER (SEQ ID NO: 1, nucleotide; SEQ ID NO: 2, polypeptide). Understood is that the complete amino acid sequence for any of the mutants would entail the substitution of the mutant residues for residues 203–219 in the wild-type sequence (SEQ ID NO: 2).

TABLE 16

ERα polypeptide sequence

```
Met Thr Met Thr Leu His Thr Lys Ala Ser Gly Met Ala Leu Leu His   (SEQ ID NO:2; NM_000125)
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
                195                 200                 205
```

TABLE 16-continued

| ERα polypeptide sequence |
|---|

```
Phe Lys Arg Ser Ile Gln Gly His Asn Asp Tyr Met Cys Pro Ala Thr
    210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
            260                 265                 270
Asp Gly Glu Gly Arg Gly Glu Val Gly Ser Ala Gly Asp Met Arg Ala
        275                 280                 285
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Val
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595
```

TABLE 17

Comparison of residues 203–219 of wild-type and mutant ERs

| ER | Amino acid sequence | SEQ ID NO: |
|---|---|---|
| WT | Glu Gly Cys Lys Ala Phe Phe Lys Arg Ser Ile Gln Gly His Asn Asp Tyr | 2 |
| ER3M | Trp Gly Cys Lys Ala Phe Phe Lys Arg Ser Ile Ala Gly Gly Asn Asp Tyr | 4 |
| ER3.1 | Trp Gly Cys Lys Ala Phe Phe Lys Arg Ser Ile Asn Arg His Asn Ser Tyr | 6 |
| ER4.3 | Trp Gly Cys Lys Ala Phe Phe Lys Arg Ser Ile Val Arg Pro Thr Asp Tyr | 8 |
| ER6.2 | Glu Gly Cys Lys Ala Phe Phe Lys Arg Ser Ile Ala Arg Arg Leu Asp Tyr | 10 |
| ER2 | Trp Gly Cys Lys Ala Phe Phe Lys Arg Ser Ile Ala Arg His Asn Asp Tyr | 12 |
| ER4 | Trp Gly Cys Lys Ala Phe Phe Lys Arg Ser Ile Ala Arg Gly Asn Asp Tyr | 14 |
| ER2.1 | Trp Ser Cys Lys Ala Phe Phe Lys Arg Ser Ile Ala Gly Gly Asn Asp Tyr | 16 |
| ER7.2 | Glu Gly Cys Lys Ala Phe Phe Lys Arg Ser Ile Gln Arg His Pro Arg Tyr | 18 |
| ER15.3 | Glu Ser Cys Lys Ala Phe Phe Lys Arg Ser Ile Gly Gly His Asn Tyr Tyr | 20 |
| ER50.1 | Trp Ser Cys Lys Gly Phe Phe Lys Arg Ser Ile Lys Gln Gly His Asn Asp Tyr | 22 |
| ER57.1 | Trp Ser Cys Lys Gly Phe Phe Lys Arg Ser Ile Lys Gly Val Pro Thr Tyr | 24 |
| Residue | 203 204 205 206 207 208 209 210 211 212 213 214 215 216 217 218 219 | NA |

ER Chimeras

To increase polypeptide synthesis in the TAS's of the invention, the ER3M mutant was fused at the amino or carboxy terminus to the carboxy terminal portions (either 79 amino acids or 129 amino acids) of the transactivator VP16. Table 18 shows the VP16 polynucleotide sequence coding for the 129 carboxy terminal amino acids. Underlined is the portion coding for the 79 carboxy-terminal amino acids.

TABLE 18

VP16 polynucleotide sequence coding for carboxy-terminal 129 amino acids (SEQ ID NO:25; Acession No. U89929)

```
tccgcgtaca gccgcgcgcg tacgaaaaac aattacgggt ctaccatcga gggcctgctc   60
gatctcccgg acgacgacgc ccccgaagag gcggggctgg cggctccgcg cctgtcctttt  120 ctccccgcgg gacacacgcg cagactgtcg acggccccccc cgaccgatgt cagcctgggg  180
gacgagctcc acttagacgg cgaggacgtg gcgatggcgc atgccgacgc gctagacgat  240
ttcgatctgg acatgttggg ggacgggat tccccgggtc cgggatttac ccccacgac    300 tccgccccct acggcgctct ggatatgccc gacttccagt ttgagcagat gtttaccgat   360
gcccttggaa ttgacgagta cggtgggtag                                    390
```

Shown in Table 19 is the VP16 polypeptide sequence (SEQ ID NO: 26) encoded by SEQ ID NO: 25. The underlined portion is the 79 amino acid polypeptide used to make fusion proteins (see Examples). SEQ ID NO: 26 represents a preferred embodiment of an ER mutant suitable for high levels of polypeptide synthesis in the TAS's that can be fused to similar VP16 sequences. Preferably, the VP16 fusion comprises the 79 amino acid core VP16 sequence or the extended 129 amino acid VP16 sequence. Preferably, the VP16 sequence is inserted in frame. Preferably, the VP16 sequence is inserted internally of the mutant ER; more preferably, at the carboxy terminus, and most preferably at the amino terminus. Thus, in addition to ER3M-VP16, the mutant fusion polypeptides ER3.1-VP16, ER4.3-VP16, ER6.2-VP16, ER2-VP16, ER4-VP16, ER2.1-VP16, ER7.2-VP16, ER15.3-VP16, ER50.1-VP16, and ER57.1-VP16 (SEQ ID NOS: 4, 6, 8, 10, 12, 14, 16, 18, 20, 22 and 24 fused to SEQ ID NO: 26) may also be made and used. Examples of such fusions are shown in Tables 20–21 (ER3M-VP16-N-129 (129 aa VP16 sequence fused at amino terminus) polynucleotide (SEQ ID NO: 66) and polypeptide (SEQ ID NO: 67), respectively), Tables 22–23 (ER3M-VP16-N-79 (79 aa VP16 sequence fused at ER3M amino terminus polynucleotide (SEQ ID NO: 68) and polypeptide (SEQ ID NO: 69), respectively), Tables 24–25 (ER3M-VP16-C-129; 129 aa VP16 sequence fused at carboxy terminus polynucleotide (SEQ ID NO: 70) and polypeptide (SEQ ID NO: 71), respectively), and Tables 26–27 (ER3M-VP16-C-79; 79 aa VP16 sequence fused at carboxy terminus, polynucleotide (SEQ ID NO: 72) and polypeptide (SEQ ID NO: 73), respectively). In Tables 20–27, the VP16 sequences are underlined.

TABLE 19

VP16 polypeptide sequence of 129 carboxy terminal amino acids (SEQ ID NO:26; (Triezenberg et al., 1988))

```
Ser Ala Tyr Ser Arg Ala Arg Thr Lys Asn Asn Tyr Gly Ser Thr Ile
1               5                   10                  15

Glu Gly Leu Leu Asp Leu Pro Asp Asp Ala Pro Glu Glu Ala Gly
            20                  25                  30

Leu Ala Ala Pro Arg Leu Ser Phe Leu Pro Ala Gly His Thr Arg Arg
        35                  40                  45

Leu Ser Thr Ala Pro Pro Thr Asp Val Ser Leu Gly Asp Glu Leu His
    50                  55                  60

Leu Asp Gly Glu Asp Val Ala Met Ala His Ala Asp Ala Leu Asp Asp
65                  70                  75                  80

Phe Asp Leu Asp Met Leu Gly Asp Gly Asp Ser Pro Gly Pro Gly Phe
                85                  90                  95

Thr Pro His Asp Ser Ala Pro Tyr Gly Ala Leu Asp Met Ala Asp Phe
            100                 105                 110

Glu Phe Glu Gln Met Phe Thr Asp Ala Leu Gly Ile Asp Glu Tyr Gly
        115                 120                 125

Gly
```

TABLE 20

ER3M-VP16-N-129 polynucleotide sequence

(SEQ ID NO.66)

```
atgtccgcgt acagccgcgc gcgtacgaaa aacaattacg ggtctaccat cgagggcctg   60
ctcgatctcc cggacgacga cgcccccgaa gaggcggggc tggcggctcc cgcctgtcc   120
tttctccccg cgggacacac gcgcagactg tcgacggccc cccgaccga tgtcagcctg   180
ggggacgagc tccacttaga cggcgaggac gtggcgatgg cgcatgccga cgcgctagac   240
gatttcgatc tggacatgtt gggggacggg gattccccgg gtccgggatt taccccccac   300
gactccgccc cctacggcgc tctggatatg gccgacttcg agtttgagca gatgtttacc   360
gatgcccttg gaattgacga gtacggtggg tctagcatga ccatgaccct ccacaccaaa   420
gcatctggga tggccctact gcatcagatc aagggaacg agctgagcc cctgaaccgt   480
ccgcagctca agatccccct ggagcggccc ctgggcgagg tgtacctgga cagcagcaag   540
cccgccgtgt acaactaccc cgagggcgcc gcctacgagt tcaacgccgc ggccgccgcc   600
aacgcgcagg tctacggtca gaccggcctc ccctacggcc ccgggtctga ggctgcggcg   660
ttcggctcca acggcctggg gggtttcccc ccactcaaca gcgtgtctcc gagcccgctg   720
atgctactgc acccgccgcc gcagctgtcg cctttcctgc agccccacgg ccagcaggtg   780
ccctactacc tggagaacga gcccagcggc tacacggtgc gcgaggccgg cccgccggca   840
ttctacaggc caaattcaga taatcgacgc cagggtggca gagaaagatt ggccagtacc   900
aatgacaagg gaagtatggc tatggaatct gccaaggaga ctcgctactg tgcagtgtgc   960
aatgactatg cttcaggcta ccattatgga gtctggtcct gttgggggctg caaggccttc  1020
ttcaagagat ctattgcagg aggtaacgac tatatgtgtc cagccaccaa ccagtgcacc  1080
attgataaaa acaggaggaa gagctgccag gcctgccgc tccgcaaatg ctacgaagtg  1140
ggaatgatga aagtgggat acgaaaagac cgaagaggag ggagaatgtt gaaacacaag  1200
cgccagagag atgatgggga gggcagggt gaagtgggt ctgctggaga catgagagct  1260
```

TABLE 20-continued

ER3M-VP16-N-129 polynucleotide sequence

```
gccaaccttt ggccaagccc gctcatgatc aaacgctcta agaagaacag cctggccttg   1320
tccctgacgg ccgaccagat ggtcagtgcc ttgttggatg ctgagccccc catactctat   1380
tccgagtatg atcctaccag acccttcagt gaagcttcga tgatgggctt actgaccaac   1440
ctggcagaca gggagctggt tcacatgatc aactgggcga gagggtgcc aggctttgtg    1500
gatttgaccc tccatgatca ggtccacctt ctagaatgtg cctggctaga gatcctgatg   1560
attggtctcg tctggcgctc catggagcac ccagtgaagc tactgttttgc tcctaacttg  1620
ctcttggaca ggaaccaggg aaaatgtgta gagggcatgg tggagatctt cgacatgctg   1680
ctggctacat catctcggtt ccgcatgatg aatctgcagg gagaggagtt tgtgtgcctc   1740
aaatctatta ttttgcttaa ttctggagtg tacacatttc tgtccagcac cctgaagtct   1800
ctggaagaga aggaccatat ccaccgagtc ctggacaaga tcacagacac tttgatccac   1860
ctgatggcca aggcaggcct gacccctgcag cagcagcacc agcggctggc ccagctcccc   1920
ctcatcctct cccacatcag gcacatgagt aacaaaggca tggagcatct gtacagcatg   1980
aagtgcaaga acgtggtgcc cctctatgac ctgctgctgg agatgctgga cgcccaccgc   2040
ctacatgcgc ccactagccg tggaggggca tccgtggagg agacggacca aagccacttg   2100
gccactgcgg gctctacttc atcgcattcc ttgcaaaagt attacatcac gggggaggca   2160
gagggtttcc ctgccacagt c                                             2181
```

TABLE 21

ER3M-VP16-N-129 polypeptide sequence

```
Met Ser Ala Tyr Ser Arg Ala Arg Thr Lys Asn Asn Tyr Gly Ser Thr   (SEQ ID NO:67)
1               5                   10                  15

Ile Glu Gly Leu Leu Asp Leu Pro Asp Asp Ala Pro Glu Ala
            20                  25                  30

Gly Leu Ala Ala Pro Arg Leu Ser Phe Leu Pro Ala Gly His Thr Arg
        35                  40                  45

Arg Leu Ser Thr Ala Pro Pro Thr Asp Val Ser Leu Gly Asp Glu Leu
    50                  55                  60

His Leu Asp Gly Glu Asp Val Ala Met Ala His Ala Asp Ala Leu Asp
65                  70                  75                  80

Asp Phe Asp Leu Asp Met Leu Gly Asp Gly Asp Ser Pro Gly Pro Gly
                85                  90                  95

Phe Thr Pro His Asp Ser Ala Pro Tyr Gly Ala Leu Asp Met Ala Asp
                100                 105                 110

Phe Glu Phe Glu Gln Met Phe Thr Asp Ala Leu Gly Ile Asp Glu Tyr
            115                 120                 125

Gly Gly Ser Ser Met Thr Met Thr Leu His Thr Lys Ala Ser Gly Met
                    135                 140

Ala Leu Leu His Gln Ile Gln Gly Asn Glu Leu Glu Pro Leu Asn Arg
145                 150                 155                 160

Pro Gln Leu Lys Ile Pro Leu Glu Arg Pro Leu Gly Glu Val Tyr Leu
                165                 170                 175

Asp Ser Ser Lys Pro Ala Val Tyr Asn Tyr Pro Glu Gly Ala Ala Tyr
                180                 185                 190

Glu Phe Asn Ala Ala Ala Ala Ala Asn Ala Gln Val Tyr Gly Gln Thr
            195                 200                 205
```

TABLE 21-continued

ER3M-VP16-N-129 polypeptide sequence

Gly Leu Pro Tyr Gly Pro Gly Ser Glu Ala Ala Phe Gly Ser Asn
    210             215             220

Gly Leu Gly Gly Phe Pro Pro Leu Asn Ser Val Ser Pro Ser Pro Leu
225             230             235             240

Met Leu Leu His Pro Pro Gln Leu Ser Pro Phe Leu Gln Pro His
            245             250             255

Gly Gln Gln Val Pro Tyr Tyr Leu Glu Asn Glu Pro Ser Gly Tyr Thr
            260             265             270

Val Arg Glu Ala Gly Pro Pro Ala Phe Tyr Arg Pro Asn Ser Asp Asn
        275             280             285

Arg Arg Gln Gly Gly Arg Glu Arg Leu Ala Ser Thr Asn Asp Lys Gly
    290             295             300

Ser Met Ala Met Glu Ser Ala Lys Glu Thr Arg Tyr Cys Ala Val Cys
305             310             315             320

Asn Asp Tyr Ala Ser Gly Tyr His Tyr Gly Val Trp Ser Cys Trp Gly
                325             330             335

Cys Lys Ala Phe Phe Lys Arg Ser Ile Ala Gly Gly Asn Asp Tyr Met
            340             345             350

Cys Pro Ala Thr Asn Gln Cys Thr Ile Asp Lys Asn Arg Arg Lys Ser
            355             360             365

Cys Gln Ala Cys Arg Leu Arg Lys Cys Tyr Glu Val Gly Met Met Lys
    370             375             380

Gly Gly Ile Arg Lys Asp Arg Arg Gly Gly Arg Met Leu Lys His Lys
385             390             395             400

Arg Gln Arg Asp Asp Gly Glu Gly Arg Gly Glu Val Gly Ser Ala Gly
                405             410             415

Asp Met Arg Ala Ala Asn Leu Trp Pro Ser Pro Leu Met Ile Lys Arg
            420             425             430

Ser Lys Lys Asn Ser Leu Ala Leu Ser Leu Thr Ala Asp Gln Met Val
            435             440             445

Ser Ala Leu Leu Asp Ala Glu Pro Pro Ile Leu Tyr Ser Glu Tyr Asp
    450             455             460

Pro Thr Arg Pro Phe Ser Glu Ala Ser Met Met Gly Leu Leu Thr Asn
465             470             475             480

Leu Ala Asp Arg Glu Leu Val His Met Ile Asn Trp Ala Lys Arg Val
                485             490             495

Pro Gly Phe Val Asp Leu Thr Leu His Asp Gln Val His Leu Leu Glu
            500             505             510

Cys Ala Trp Leu Glu Ile Leu Met Ile Gly Leu Val Trp Arg Ser Met
            515             520             525

Glu His Pro Val Lys Leu Leu Phe Ala Pro Asn Leu Leu Asp Arg
    530             535             540

Asn Gln Gly Lys Cys Val Glu Gly Met Val Glu Ile Phe Asp Met Leu
545             550             555             560

Leu Ala Thr Ser Ser Arg Phe Arg Met Met Asn Leu Gln Gly Glu Glu
                565             570             575

Phe Val Cys Leu Lys Ser Ile Ile Leu Leu Asn Ser Gly Val Tyr Thr
            580             585             590

Phe Leu Ser Ser Thr Leu Lys Ser Leu Glu Glu Lys Asp His Ile His
            595             600             605

Arg Val Leu Asp Lys Ile Thr Asp Thr Leu Ile His Leu Met Ala Lys

TABLE 21-continued

ER3M-VP16-N-129 polypeptide sequence

```
            610                 615                 620
Ala Gly Leu Thr Leu Gln Gln Gln His Gln Arg Leu Ala Gln Leu Leu
625                 630                 635                 640

Leu Ile Leu Ser His Ile Arg His Met Ser Asn Lys Gly Met Glu His
                645                 650                 655

Leu Tyr Ser Met Lys Cys Lys Asn Val Val Pro Leu Tyr Asp Leu Leu
            660                 665                 670

Leu Glu Met Leu Asp Ala His Arg Leu His Ala Pro Thr Ser Arg Gly
        675                 680                 685

Gly Ala Ser Val Glu Glu Thr Asp Gln Ser His Leu Ala Thr Ala Gly
    690                 695                 700

Ser Thr Ser Ser His Ser Leu Gln Lys Tyr Tyr Ile Thr Gly Glu Ala
705                 710                 715                 720

Glu Gly Phe Pro Ala Thr Val
                725
```

TABLE 22

ER3M-VP16-N-79 polynucleotide sequence

| | (SEQ ID NO:68) |
|---|---|
| atgacggccc ccccgaccga tgtcagcctg ggggacgagc tccacttaga cggcgaggac | 60 |
| gtggcgatgg cgcatgccga cgcgctagac gatttcgatc tggacatgtt ggggacgggg | 120 |
| gattccccgg gtccgggatt tacccccac gactccgccc cctacggcgc tctggatatg | 180 |
| gccgacttcg agtttgagca gatgtttacc gatgcccttg gaattgacga gtacggtggg | 240 |
| tctagcatga ccatgaccct ccacaccaaa gcatctggga tggccctact gcatcagatc | 300 |
| caagggaacg agctggagcc cctgaaccgt ccgcagctca agatccccct ggagcggccc | 360 |
| ctgggcgagg tgtacctgga cagcagcaag cccgccgtgt acaactaccc cgagggcgcc | 420 |
| gcctacgagt tcaacgccgc ggccgccgcc aacgcgcagg tctacggtca gaccggcctc | 480 |
| ccctacggcc ccgggtctga ggctgcggcg ttcggctcca acggcctggg gggtttcccc | 540 |
| ccactcaaca gcgtgtctcc gagcccgctg atgctactgc accgccgcc gcagctgtcg | 600 |
| cctttcctgc agccccacgg ccagcaggtg ccctactacc tggagaacga gcccagcggc | 660 |
| tacacggtgc gcgaggccgg cccgccggca ttctacaggc caaattcaga taatcgacgc | 720 |
| cagggtggca gagaaagatt ggccagtacc aatgacaagg gaagtatggc tatggaatct | 780 |
| gccaaggaga ctcgctactg tgcagtgtgc aatgactatg cttcaggcta ccattatgga | 840 |
| gtctggtcct gttggggctg caaggccttc ttcaagagat ctattgcagg aggtaacgac | 900 |
| tatatgtgtc cagccaccaa ccagtgcacc attgataaaa acaggaggaa gagctgccag | 960 |
| gcctgccggc tccgcaaatg ctacgaagtg ggaatgatga aggtgggat acgaaaagac | 1020 |
| cgaagaggag ggagaatgtt gaaacacaag cgccagagag atgatgggga gggcaggggt | 1080 |
| gaagtggggt ctgctggaga catgagagct gccaaccttt ggccaagccc gctcatgatc | 1140 |
| aaacgctcta agaagaacag cctggccttg tccctgacgg ccgaccagat ggtcagtgcc | 1200 |
| ttgttggatg ctgagccccc catactctat tccgagtatg atcctaccag acccttcagt | 1260 |
| gaagcttcga tgatgggctt actgaccaac ctggcagaca gggagctggt tcacatgatc | 1320 |
| aactgggcga agagggtgcc aggctttgtg gatttgaccc tccatgatca ggtccacctt | 1380 |

TABLE 22-continued

ER3M-VP16-N-79 polynucleotide sequence

```
ctagaatgtg cctggctaga gatcctgatg attggtctcg tctggcgctc catggagcac  1440
ccagtgaagc tactgtttgc tcctaacttg ctcttggaca ggaaccaggg aaaatgtgta  1500
gagggcatgg tggagagctt cgacatgctg ctggctacat catctcggtt ccgcatgatg  1560
aatctgcagg gagaggagtt tgtgtgcctc aaatctatta ttttgcttaa ttctggagtg  1620
tacacatttc tgtccagcac cctgaagtct ctggaagaga aggaccatat ccaccgagtc  1680
ctggacaaga tcacagacac tttgatccac ctgatggcca aggcaggcct gaccctgcag  1740
cagcagcacc agcggctggc ccagctcctc ctcatcctct cccacatcag gcacatgagt  1800
aacaaaggca tggagcatct gtacagcatg aagtgcaaga acgtggtgcc cctctatgac  1860
ctgctgctgg agatgctgga cgcccaccgc ctacatgcgc ccactagccg tggaggggca  1920
tccgtggagg agacggacca aagccacttg gccactgcgg gctctacttc atcgcattcc  1980
ttgcaaaagt attacatcac gggggaggca gagggtttcc ctgccacagt c            2031
```

TABLE 23

ER3M-VP16-N-79 polypeptide sequence

```
Met Thr Ala Pro Pro Thr Asp Val Ser Leu Gly Asp Glu Leu His Leu      (SEQ ID NO:69)
 1               5                  10                  15

Asp Gly Glu Asp Val Ala Met Ala His Ala Asp Ala Leu Asp Asp Phe
                20                  25                  30

Asp Leu Asp Met Leu Gly Asp Gly Asp Ser Pro Gly Pro Gly Phe Thr
            35                  40                  45

Pro His Asp Ser Ala Pro Tyr Gly Ala Leu Asp Met Ala Asp Phe Glu
        50                  55                  60

Phe Glu Gln Met Phe Thr Asp Ala Leu Gly Ile Asp Glu Tyr Gly Gly
65                  70                  75                  80

Ser Ser Met Thr Met Thr Leu His Thr Lys Ala Ser Sly Met Ala Leu
                85                  90                  95

Leu His Gln Ile Gln Gly Asn Glu Leu Glu Pro Leu Asn Arg Pro Gln
                100                 105                 110

Leu Lys Ile Pro Leu Glu Arg Pro Leu Gly Glu Val Tyr Leu Asp Ser
            115                 120                 125

Ser Lys Pro Ala Val Tyr Asn Tyr Pro Glu Gly Ala Ala Tyr Glu Phe
        130                 135                 140

Asn Ala Ala Ala Ala Asn Ala Gln Val Tyr Gly Gln Thr Gly Leu
145                 150                 155                 160

Pro Tyr Gly Pro Gly Ser Glu Ala Ala Ala Phe Gly Ser Asn Gly Leu
                165                 170                 175

Gly Gly Phe Pro Pro Leu Asn Ser Val Ser Pro Ser Pro Leu Met Leu
                180                 185                 190

Leu His Pro Pro Pro Gln Leu Ser Pro Phe Leu Gln Pro His Gly Gln
            195                 200                 205

Gln Val Pro Tyr Tyr Leu Glu Asn Glu Pro Ser Gly Tyr Thr Val Arg
        210                 215                 220

Glu Ala Gly Pro Pro Ala Phe Tyr Arg Pro Asn Ser Asp Asn Arg Arg
225                 230                 235                 240

Gln Gly Gly Arg Glu Arg Leu Ala Ser Thr Asn Asp Lys Gly Ser Met
                245                 250                 255
```

TABLE 23-continued

ER3M-VP16-N-79 polypeptide sequence

Ala Met Glu Ser Ala Lys Glu Thr Arg Tyr Cys Ala Val Cys Asn Asp
        260                 265                 270

Tyr Ala Ser Gly Tyr His Tyr Gly Val Trp Ser Cys Trp Gly Cys Lys
        275                 280                 285

Ala Phe Phe Lys Arg Ser Ile Ala Gly Gly Asn Asp Tyr Met Cys Pro
        290                 295                 300

Ala Thr Asn Gln Cys Thr Ile Asp Lys Asn Arg Arg Lys Ser Cys Gln
305                 310                 315                 320

Ala Cys Arg Leu Arg Lys Cys Tyr Glu Val Gly Met Met Lys Gly Gly
                325                 330                 335

Ile Arg Lys Asp Arg Arg Gly Gly Arg Met Leu Lys His Lys Arg Gln
                340                 345                 350

Arg Asp Asp Gly Glu Gly Arg Gly Glu Val Gly Ser Ala Gly Asp Met
                355                 360                 365

Arg Ala Ala Asn Leu Trp Pro Ser Pro Leu Met Ile Lys Arg Ser Lys
        370                 375                 380

Lys Asn Ser Leu Ala Leu Ser Leu Thr Ala Asp Gln Met Val Ser Ala
385                 390                 395                 400

Leu Leu Asp Ala Glu Pro Pro Ile Leu Tyr Ser Glu Tyr Asp Pro Thr
                405                 410                 415

Arg Pro Phe Ser Glu Ala Ser Met Met Gly Leu Leu Thr Asn Leu Ala
                420                 425                 430

Asp Arg Glu Leu Val His Met Ile Asn Trp Ala Lys Arg Val Pro Gly
                435                 440                 445

Phe Val Asp Leu Thr Leu His Asp Gln Val His Leu Leu Glu Cys Ala
        450                 455                 460

Trp Leu Glu Ile Leu Met Ile Gly Leu Val Trp Arg Ser Met Glu His
465                 470                 475                 480

Pro Val Lys Leu Leu Phe Ala Pro Asn Leu Leu Asp Arg Asn Gln
                485                 490                 495

Gly Lys Cys Val Glu Gly Met Val Glu Ile Phe Asp Met Leu Leu Ala
                500                 505                 510

Thr Ser Ser Arg Phe Arg Met Met Asn Leu Gln Gly Glu Glu Phe Val
        515                 520                 525

Cys Leu Lys Ser Ile Ile Leu Leu Asn Ser Gly Val Tyr Thr Phe Leu
        530                 535                 540

Ser Ser Thr Leu Lys Ser Leu Glu Glu Lys Asp His Ile His Arg Val
545                 550                 555                 560

Leu Asp Lys Ile Thr Asp Thr Leu Ile His Leu Met Ala Lys Ala Gly
                565                 570                 575

Leu Thr Leu Gln Gln Gln His Gln Arg Leu Ala Gln Leu Leu Leu Ile
                580                 585                 590

Leu Ser His Ile Arg His Met Ser Asn Lys Gly Met Glu His Leu Tyr
        595                 600                 605

Ser Met Lys Cys Lys Asn Val Val Pro Leu Tyr Asp Leu Leu Leu Glu
        610                 615                 620

Met Leu Asp Ala His Arg Leu His Ala Pro Thr Ser Arg Gly Gly Ala
625                 630                 635                 640

Ser Val Glu Glu Thr Asp Gln Ser His Leu Ala Thr Ala Gly Ser Thr
                645                 650                 655

TABLE 23-continued

ER3M-VP16-N-79 polypeptide sequence

```
Ser Ser His Ser Leu Gln Lys Tyr Tyr Ile Thr Gly Glu Ala Glu Gly
            660                 665                 670

Phe Pro Ala Thr Val
    675
```

TABLE 24

ER3M-VP16-C-129 polynucleotide sequence (SEQ ID NO:70)

| | |
|---|---|
| atgaccatga ccctccacac caaagcatct gggatggccc tactgcatca gatccaaggg | ==60 |
| aacgagctgg agcccctgaa ccgtccgcag ctcaagatcc ccctggagcg gccccctggc | =120 |
| gaggtgtacc tggacagcag caagcccgcc gtgtacaact accccgaggg cgccgcctac | =180 |
| gagttcaacg ccgcggccgc cgccaacgcg caggtctacg gtcagaccgg cctcccctac | =240 |
| ggccccgggt ctgaggctgc ggcgttcggc tccaacggcc tggggggttt ccccccactc | =300 |
| aacagcgtgt ctccgagccc gctgatgcta ctgcacccgc cgccgcagct gtcgcctttc | =360 |
| ctgcagcccc acggccagca ggtgccctac tacctggaga cgagcccag cggctacacg | =420 |
| gtgcgcgagg ccggcccgcc ggcattctac aggccaaatt cagataatcg acgccagggt | =480 |
| ggcagagaaa gattggccag taccaatgac aagggaagta tggctatgga atctgccaag | =540 |
| gagactcgct actgtgcagt gtgcaatgac tatgcttcag gctaccatta tggagtctgg | =600 |
| tcctgttggg gctgcaaggc cttcttcaag agatctattg caggaggtaa cgactatatg | =660 |
| tgtccagcca ccaaccagtg caccattgat aaaaacagga ggaagagctg ccaggcctgc | =720 |
| cggctccgca aatgctacga agtgggaatg atgaaaggtg ggatacgaaa agaccgaaga | =780 |
| ggagggagaa tgttgaaaca caagcgccag agagatgatg gggagggcag gggtgaagtg | =840 |
| gggtctgctg gagacatgag agctgccaac ctttggccaa gcccgctcat gatcaaacgc | =900 |
| tctaagaaga acagcctggc cttgtccctg acggccgacc agatggtcag tgccttgttg | =960 |
| gatgctgagc cccccatact ctattccgag tatgatccta ccagacccctt cagtgaagct | 1020 |
| tcgatgatgg gcttactgac caacctggca gacagggagc tggttcacat gatcaactgg | 1080 |
| gcgaagaggg tgccaggctt tgtggatttg accctccatg atcaggtcca ccttctagaa | 1140 |
| tgtgcctggc tagagatcct gatgattggt ctcgtctggc gctccatgga gcacccagtg | 1200 |
| aagctactgt ttgctcctaa cttgctcttg gacaggaacc agggaaaatg tgtagagggc | 1260 |
| atggtggaga tcttcgacat gctgctggct acatcatctc ggttccgcat gatgaatctg | 1320 |
| cagggagagg agtttgtgtg cctcaaatct attattttgc ttaattctgg agtgtacaca | 1380 |
| tttctgtcca gcaccctgaa gtctctggaa gagaaggacc atatccaccg agtcctggac | 1440 |
| aagatcacag acactttgat ccacctgatg gccaaggcag gcctgaccct gcagcagcag | 1500 |
| caccagcggc tggcccagct cctcctcatc ctctcccaca tcaggcacat gagtaacaaa | 1560 |
| ggcatggagc atctgtacag catgaagtgc aagaacgtgg tgcccctcta tgacctgctg | 1620 |
| ctggagatgc tggacgccca ccgcctacat gcgcccacta gccgtggagg ggcatccgtg | 1680 |
| gaggagacgg accaaagcca cttggccact gcgggctcta cttcatcgca ttccttgcaa | 1740 |
| aagtattaca tcacggggga ggcagagggt ttccctgcca cagtcggtac <u>ctccgcgtac</u> | 1800 |
| <u>agccgcgcgc gtacgaaaaa caattacggg tctaccatcg agggcctgct cgatctcccg</u> | 1860 |
| <u>gacgacgacg ccccgaaga ggcggggctg gcggctccgc gcctgtcctt tctcccgcg</u> | 1920 |

TABLE 24-continued

ER3M-VP16-C-129 polynucleotide sequence

```
ggacacacgc gcagactgtc gacggccccc ccgaccgatg tcagcctggg ggacgagctc  1980
cacttagacg gcgaggacgt ggcgatggcg catgccgacg cgctagacga tttcgatctg  2040
gacatgttgg gggacgggga ttccccgggt ccgggattta ccccccacga ctccgccccc  2100
tacggcgctc tggatatggc cgacttcgag tttgagcaga tgtttaccga tgcccttgga  2160
attgacgagt acggtggg                                                 2178
```

TABLE 25

ER3M-VP16-C-129 polypeptide sequence (SEQ ID NO:71)

```
Met Thr Met Thr Leu His Thr Lys Ala Ser Gly Met Ala Leu Leu His
1===============5==================10=================15

Gln Ile Gln Gly Asn Glu Leu Glu Pro Leu Asn Arg Pro Gln Leu Lys
============20==================25=================30

Ile Pro Leu Glu Arg Pro Leu Gly Glu Val Tyr Leu Asp Ser Ser Lys
========35==================40=================45

Pro Ala Val Tyr Asn Tyr Pro Glu Gly Ala Ala Tyr Glu Phe Asn Ala
====50==================55=================60

Ala Ala Ala Ala Asn Ala Gln Val Tyr Gly Gln Thr Gly Leu Pro Tyr
65==================70==================75=================80

Gly Pro Gly Ser Glu Ala Ala Ala Phe Gly Ser Asn Gly Leu Gly Gly
==================85==================90=================95

Phe Pro Pro Leu Asn Ser Val Ser Pro Ser Pro Leu Met Leu Leu His
============100=================105================110

Pro Pro Pro Gln Leu Ser Pro Phe Leu Gln Pro His Gly Gln Gln Val
========115=================120================125

Pro Tyr Tyr Leu Glu Asn Glu Pro Ser Gly Tyr Thr Val Arg Glu Ala
====130=================135================140

Gly Pro Pro Ala Phe Tyr Arg Pro Asn Ser Asp Asn Arg Arg Gln Gly
145=================150================155================160

Gly Arg Glu Arg Leu Ala Ser Thr Asn Asp Lys Gly Ser Met Ala Met
=================165================170================175

Glu Ser Ala Lys Glu Thr Arg Tyr Cys Ala Val Cys Asn Asp Tyr Ala
============180=================185================190

Ser Gly Tyr His Tyr Gly Val Trp Ser Cys Trp Gly Cys Lys Ala Phe
=========195================200================205

Phe Lys Arg Ser Ile Ala Gly Gly Asn Asp Tyr Met Cys Pro Ala Thr
====210=================215================220

Asn Gln Cys Thr Ile Asp Lys Asn Arg Arg Lys Ser Cys Gln Ala Cys
225=================230================235================240

Arg Leu Arg Lys Cys Tyr Glu Val Gly Met Met Lys Gly Gly Ile Arg
=================245================250================255

Lys Asp Arg Arg Gly Gly Arg Met Leu Lys His Lys Arg Gln Arg Asp
============260=================265================270

Asp Gly Glu Gly Arg Gly Glu Val Gly Ser Ala Gly Asp Met Arg Ala
========275=================280================285

Ala Asn Leu Trp Pro Ser Pro Leu Met Ile Lys Arg Ser Lys Lys Asn
====290=================295================300

Ser Leu Ala Leu Ser Leu Thr Ala Asp Gln Met Val Ser Ala Leu Leu
305=================310================315================320

Asp Ala Glu Pro Pro Ile Leu Tyr Ser Glu Tyr Asp Pro Thr Arg Pro
=================325================330================335
```

TABLE 25-continued

ER3M-VP16-C-129 polypeptide sequence

```
Phe Ser Glu Ala Ser Met Met Gly Leu Leu Thr Asn Leu Ala Asp Arg
=============340=================345=================350

Glu Leu Val His Met Ile Asn Trp Ala Lys Arg Val Pro Gly Phe Val
=========355=================360=================365

Asp Leu Thr Leu His Asp Gln Val His Leu Leu Glu Cys Ala Trp Leu
=====370=================375=================380

Glu Ile Leu Met Ile Gly Leu Val Trp Arg Ser Met Glu His Pro Val
385=================390=================395=================400

Lys Leu Leu Phe Ala Pro Asn Leu Leu Leu Asp Arg Asn Gln Gly Lys
=================405=================410=================415

Cys Val Glu Gly Met Val Glu Ile Phe Asp Met Leu Leu Ala Thr Ser
=============420=================425=================430

Ser Arg Phe Arg Met Met Asn Leu Gln Gly Glu Glu Phe Val Cys Leu
=========435=================440=================445

Lys Ser Ile Ile Leu Leu Asn Ser Gly Val Tyr Thr Phe Leu Ser Ser
=====450=================455=================460

Thr Leu Lys Ser Leu Glu Glu Lys Asp His Ile His Arg Val Leu Asp
465=================470=================475=================480

Lys Ile Thr Asp Thr Leu Ile His Leu Met Ala Lys Ala Gly Leu Thr
=================485=================490=================495

Leu Gln Gln Gln His Gln Arg Leu Ala Gln Leu Leu Leu Ile Leu Ser
=============500=================505=================510

His Ile Arg His Met Ser Asn Lys Gly Met Glu His Leu Tyr Ser Met
=========515=================520=================525

Lys Cys Lys Asn Val Val Pro Leu Tyr Asp Leu Leu Leu Glu Met Leu
=====530=================535=================540

Asp Ala His Arg Leu His Ala Pro Thr Ser Arg Gly Gly Ala Ser Val
545=================550=================555=================560

Glu Glu Thr Asp Gln Ser His Leu Ala Thr Ala Gly Ser Thr Ser Ser
=================565=================570=================575

His Ser Leu Gln Lys Tyr Tyr Ile Thr Gly Glu Ala Glu Gly Phe Pro
=============580=================585=================590

Ala Thr Val Gly Thr Ser=Ala=Tyr=Ser=Arg=Ala=Arg=Thr=Lys=Asn=Asn
=========595=================600=================605

Tyr=Gly=Ser=Thr=Ile=Glu=Gly=Leu=Leu=Asp=Leu=Pro=Asp=Asp=Asp=Ala
=====610=================615=================620

Pro=Glu=Glu=Ala=Gly=Leu=Ala=Ala=Pro=Arg=Leu=Ser=Phe=Leu=Pro=Ala
625=================630=================635=================640

Gly=His=Thr=Arg=Arg=Leu=Ser=Thr=Ala=Pro=Pro=Thr=Asp=Val=Ser=Leu
=================645=================650=================655

Gly=Asp=Glu=Leu=His=Leu=Asp=Gly=Glu=Asp=Val=Ala=Met=Ala=His=Ala
=============660=================665=================670

Asp=Ala=Leu=Asp=Asp=Phe=Asp=Leu=Asp=Met=Leu=Gly=Asp=Gly=Asp=Ser
=========675=================680=================685

Pro=Gly=Pro=Gly=Phe=Thr=Pro=His=Asp=Ser=Ala=Pro=Tyr=Gly=Ala=Leu
=====690=================695=================700

Asp=Met=Ala=Asp=Phe=Glu=Phe=Glu=Gln=Met=Phe=Thr=Asp=Ala=Leu=Gly
705=================710=================715=================720

Ile=Asp=Glu=Tyr=Gly=Gly
=============725
```

TABLE 26

ER3M-VP16-C-79 polynucleotide sequence (SEQ ID NO:72)

```
atgaccatga ccctccacac caaagcatct gggatggccc tactgcatca gatccaaggg    =60
aacgagctgg agcccctgaa ccgtccgcag ctcaagatcc ccctggagcg gccccctggc   =120
gaggtgtacc tggacagcag caagcccgcc gtgtacaact accccgaggg cgccgcctac   =180
gagttcaacg ccgcggccgc cgccaacgcg caggtctacg gtcagaccgg cctcccctac   =300
aacagcgtgt ctccgagccc gctgatgcta ctgcacccgc cgccgcagct gtcgcctttc   =360
ctgcagcccc acggccagca ggtgccctac tacctggaga cgagcccagc ggctacacg   =420
gtgcgcgagg ccgcccgcc ggcattctac aggccaaatt cagataatcg acgccagggt   =480
ggcagagaaa gattggccag taccaatgac aagggaagta tggctatgga atctgccaag   =540
gagactcgct actgtgcagt gtgcaatgac tatgcttcag ctaccatta tggagtctgg   =600
tcctgttggg gctgcaaggc cttcttcaag agatctattg caggaggtaa cgactatatg   =660
tgtccagcca ccaaccagtg caccattgat aaaaacagga ggaagagctg ccaggcctgc   =720
cggctccgca atgctacga agtgggaatg atgaaggtg ggatacgaaa agaccgaaga   =780
ggagggagaa tgttgaaaca caagcgccag agagatgatg gggagggcag gggtgaagtg   =840
gggtctgctg agacatgag agctgccaac ctttggccaa gcccgctcat gatcaaacgc   =900
tctaagaaga acagcctggc cttgtccctg acggccgacc agatggtcag tgccttgttg   =960
gatgctgagc ccccatact ctattccgag tatgatccta ccagacccctt cagtgaagct  1020
tcgatgatgg gcttactgac caacctggca gacaggagc tggttcacat gatcaactgg  1080
gcgaagaggg tgccaggctt tgtggatttg accctccatg atcaggtcca ccttctagaa  1140
tgtgcctggc tagagatcct gatgattggt ctcgtctggc gctccatgga gcacccagtg  1200
aagctactgt ttgctcctaa cttgctcttg gacaggaacc agggaaaatg tgtagagggc  1260
atggtggaga tcttcgacat gctgctggct acatcatctc ggttccgcat gatgaatctg  1320
cagggagagg agtttgtgtg cctcaaatct attattttgc ttaattctgg agtgtacaca  1380
tttctgtcca gcaccctgaa gtctctggaa gagaaggacc atatccaccg agtcctggac  1440
aagatcacag acactttgat ccacctgatg gccaaggcag gctgaccct gcagcagcag  1500
caccagcggc tggcccagct cctcctcatc ctctccccaca tcaggcacat gagtaacaaa  1560
ggcatggagc atctgtacag catgaagtgc aagaacgtgg tgcccctcta tgacctgctg  1620
ctggagatgc tggacgccca ccgcctacat gcgcccacta gccgtggagg ggcatccgtg  1680
gaggagacgg accaaagcca cttggccact gcgggctcta cttcatcgca ttccttgcaa  1740
aagtattaca tcacgggga ggcagagggt ttccctgcca cagtcggtac cacggccccc  1800
ccgaccgatg=tcagcctggg=ggacgagctc=cacttagacg=gcgaggacgt=ggcgatggcg  1860
catgccgacg=cgctagacga=tttcgatctg=gacatgttgg=gggacgggga=ttccccgggt  1920
ccgggattta=cccccacga=ctccgccccc=tacggcgctc=tggatatggc=cgacttcgag  1980
tttgagcaga=tgtttaccga=tgcccttgga=attgacgagt=acggtggg                2028
```

TABLE 27

ER3M-VP16-C-79 polypeptide sequence

```
Met Thr Met Thr Leu His Thr Lys Ala Ser Gly Met Ala Leu Leu His    (SEQ ID NO:73)
1===============5===================10==================15

Gln Ile Gln Gly Asn Glu Leu Glu Pro Leu Asn Arg Pro Gln Leu Lys
==============20===================25==================30
```

TABLE 27-continued

ER3M-VP16-C-79 polypeptide sequence

```
Ile Pro Leu Glu Arg Pro Leu Gly Glu Val Tyr Leu Asp Ser Ser Lys
         35                 40                 45

Pro Ala Val Tyr Asn Tyr Pro Glu Gly Ala Ala Tyr Glu Phe Asn Ala
     50                 55                 60

Ala Ala Ala Ala Asn Ala Gln Val Tyr Gly Gln Thr Gly Leu Pro Tyr
 65                 70                 75                 80

Gly Pro Gly Ser Glu Ala Ala Ala Phe Gly Ser Asn Gly Leu Gly Gly
                 85                 90                 95

Phe Pro Pro Leu Asn Ser Val Ser Pro Ser Pro Leu Met Leu Leu His
             100                105                110

Pro Pro Pro Gln Leu Ser Pro Phe Leu Gln Pro His Gly Gln Gln Val
         115                120                125

Pro Tyr Tyr Leu Glu Asn Glu Pro Ser Gly Tyr Thr Val Arg Glu Ala
     130                135                140

Gly Pro Pro Ala Phe Tyr Arg Pro Asn Ser Asp Asn Arg Arg Gln Gly
145                150                155                160

Gly Arg Glu Arg Leu Ala Ser Thr Asn Asp Lys Gly Ser Met Ala Met
                 165                170                175

Glu Ser Ala Lys Glu Thr Arg Tyr Cys Ala Val Cys Asn Asp Tyr Ala
             180                185                190

Ser Gly Tyr His Tyr Gly Val Trp Ser Cys Trp Gly Cys Lys Ala Phe
         195                200                205

Phe Lys Arg Ser Ile Ala Gly Gly Asn Asp Tyr Met Cys Pro Ala Thr
     210                215                220

Asn Gln Cys Thr Ile Asp Lys Asn Arg Arg Lys Ser Cys Gln Ala Cys
225                230                235                240

Arg Leu Arg Lys Cys Tyr Glu Val Gly Met Met Lys Gly Gly Ile Arg
                 245                250                255

Lys Asp Arg Arg Gly Gly Arg Met Leu Lys His Lys Arg Gln Arg Asp
             260                265                270

Asp Gly Glu Gly Arg Gly Glu Val Gly Ser Ala Gly Asp Met Arg Ala
         275                280                285

Ala Asn Leu Trp Pro Ser Pro Leu Met Ile Lys Arg Ser Lys Lys Asn
     290                295                300

Ser Leu Ala Leu Ser Leu Thr Ala Asp Gln Met Val Ser Ala Leu Leu
305                310                315                320

Asp Ala Glu Pro Pro Ile Leu Tyr Ser Glu Tyr Asp Pro Thr Arg Pro
                 325                330                335

Phe Ser Glu Ala Ser Met Met Gly Leu Leu Thr Asn Leu Ala Asp Arg
             340                345                350

Glu Leu Val His Met Ile Asn Trp Ala Lys Arg Val Pro Gly Phe Val
         355                360                365

Asp Leu Thr Leu His Asp Gln Val His Leu Leu Glu Cys Ala Trp Leu
     370                375                380

Glu Ile Leu Met Ile Gly Leu Val Trp Arg Ser Met Glu His Pro Val
385                390                395                400

Lys Leu Leu Phe Ala Pro Asn Leu Leu Leu Asp Arg Asn Gln Gly Lys
                 405                410                415

Cys Val Glu Gly Met Val Glu Ile Phe Asp Met Leu Leu Ala Thr Ser
             420                425                430

Ser Arg Phe Arg Met Met Asn Leu Gln Gly Glu Glu Phe Val Cys Leu
```

TABLE 27-continued

ER3M-VP16-C-79 polypeptide sequence

```
========435=================440=================445
Lys Ser Ile Ile Leu Leu Asn Ser Gly Val Tyr Thr Phe Leu Ser Ser
====450=================455=================460

Thr Leu Lys Ser Leu Glu Glu Lys Asp His Ile His Arg Val Leu Asp
465=================470=================475=================480

Lys Ile Thr Asp Thr Leu Ile His Leu Met Ala Lys Ala Gly Leu Thr
=================485=================490=================495

Leu Gln Gln Gln His Gln Arg Leu Ala Gln Leu Leu Leu Ile Leu Ser
============500=================505=================510

His Ile Arg His Met Ser Asn Lys Gly Met Glu His Leu Tyr Ser Met
========515=================520=================525

Lys Cys Lys Asn Val Val Pro Leu Tyr Asp Leu Leu Leu Glu Met Leu
====530=================535=================540

Asp Ala His Arg Leu His Ala Pro Thr Ser Arg Gly Gly Ala Ser Val
545=================550=================555=================560

Glu Glu Thr Asp Gln Ser His Leu Ala Thr Ala Gly Ser Thr Ser Ser
=================565=================570=================575

His Ser Leu Gln Lys Tyr Tyr Ile Thr Gly Glu Ala Glu Gly Phe Pro
============580=================585=================590

Ala Thr Val Gly Thr Thr=Ala=Pro=Pro=Thr=Asp=Val=Ser=Leu=Gly=Asp
========595=================600=================605

Glu=Leu=His=Leu=Asp=Gly=Glu=Asp=Val=Ala=Met=Ala=His=Ala=Asp=Ala
====610=================615=================620

Leu=Asp=Asp=Phe=Asp=Leu=Asp=Met=Leu=Gly=Asp=Gly=Asp=Ser=Pro=Gly
625=================630=================635=================640

Pro=Gly=Phe=Thr=Pro=His=Asp=Ser=Ala=Pro=Tyr=Gly=Ala=Leu=Asp=Met
=================645=================650=================635

Ala=Asp=Phe=Glu=Phe=Glu=Gln=Met=Phe=Thr=Asp=Ala=Leu=Gly=Ile=Asp
============660=================665=================670

Glu=Tyr=Gly=Gly
========675====
```

Mutant EREs and ER-binding Palindromes

To activate transcription from the mutant ERs but not wild-type, promoters containing ERE sequences and ER-binding palindromes (PALs) were constructed. Tables 28 and 29 show polynucleotide sequences containing ERE and PAL sequences used to make these constructs; consensus ERE (cERE) sequences are underlined; PAL sequences are italicized; pS2 ERE sequences are italicized and underlined.

TABLE 28

| Consensus ERE (cERE; SEQ ID NO:83) | |
|---|---|
| aggtcactgt gacct | 15 |

TABLE 29

ERE and ER-Binding PAL polynucleotide sequences

| ERE | Polynucleotide Sequence | | SEQ ID NO: |
|---|---|---|---|
| pS2 ERE | *aggtcactgt ggccc* | 15 | 74 |
| PAL ERE | *gggccactgt ggccc* | 15 | 75 |
| ATL2/cERE | aagctt<u>aggt cactgtgacc t</u>atcaagata tcgagata<u>gg tcactgtgac ct</u>atcgactc taga | 60 64 | 76 |
| ATL2/pS2 ERE | aagctt*aggt cactgtggcc c*atcaagata tcgagata*gg tcactgtggc cc*atcgactc taga | 60 64 | 77 |

TABLE 29-continued

ERE and ER-Binding PAL polynucleotide sequences

| ERE | Polynucleotide Sequence | | | | | SEQ ID NO: |
|---|---|---|---|---|---|---|
| ATL2/PAL | aagctt*gggc* *cactgtggcc* catcaagata tcgagat*ggg* *ccactgtgc* ccatcgactc taga | | | | 60<br>64 | 78 |
| ATL4/cERE | aagctt<u>aggt</u> <u>cactgtgacc</u> <u>t</u>atcaagata tcgagat<u>agg</u> <u>tcactgtgac</u> <u>ct</u>atcgacag gaattcac<u>ag</u> <u>gtcactgtga</u> <u>cc</u>tatcaaga tatcgagat<u>a</u> <u>ggtcactgtg</u> <u>acct</u>atcgac tctaga | | | | 60<br>120<br>126 | 79 |
| ATL4/PAL | aagctt*gggc* *cactgtggcc* catcaagata tcgagat*ggg* *ccactgtggc* ccatcgacag gaattcac*gg* *gccactgtgg* *ccc*atcaaga tatcgagatg *ggccactgtg* *gcc*atcgac tctaga | | | | 60<br>120<br>126 | 80 |
| ATL8/cERE | gctagc<u>aggt</u> <u>cactgtgacc</u> <u>tt</u>gacaacta gtaagtc<u>agg</u> <u>tcactgtgac</u> <u>ct</u>gacgtact atctcgag<u>ag</u> <u>gtcactgtga</u> <u>cc</u>ttagagct gcaggtatc<u>a</u> <u>ggtcactgtg</u> <u>acct</u>tagttc attaaagctt <u>aggtcactgt</u> <u>gacct</u>atcaa gatatcgaga <u>taggtcactg</u> <u>tgacct</u>atcg acaggaattc ac<u>aggtcact</u> <u>gtgacct</u>atc aagatatcga gat<u>aggtcac</u> <u>tgtgacct</u>at cgactctaga | | | | 60<br>120<br>180<br>240<br>250 | 81 |

ATL8/PAL gctagc*gggc* *cactgtggcc* ctgacaacta gtaagtc*ggg* *ccactgtggc* ccgacgtact 60 82 atctcgag*gg* *gccactgtgg* *ccc*tagagct gcaggtatcg *ggccactgtg* *gccc*tagttc 120 attaaagctt *gggccactgt* *gccc*atcaa gatatcgaga t*gggccactg* *tggccc*atcg 180 acaggaattc ac*gggccact* *gtggccc*atc aagatatcga gat*gggccac* *tgtggccc*at 240 cgactctaga 250

The sequences around the ERE have a very small effect but they provide spacing that allows binding of more than one ER dimer. The space between two EREs is preferably at least 20 nucleotides; the sequence can be randomly-derived or selected by one of skill in the art.

III. Practicing the Invention

Definitions

Unless defined otherwise, all technical and scientific terms have the same meaning as is commonly understood by one of skill in the art to which this invention belongs. The definitions below are presented for clarity.

"Isolated," when referred to a molecule, refers to a molecule that has been identified and separated and/or recovered from a component of its natural environment. Contaminant components of its natural environment are materials that interfere with diagnostic or therapeutic use.

From here to the Examples, genes, polynucleotides are indicated in italics, polypeptides and the like are non-italicized.

Nucleic Acid-related Definitions

Probes

Probes are nucleic acid sequences of variable length, preferably between at least about 10 nucleotides (nt), 100 nt, or many (e.g., 6,000 nt) depending on the specific use. Probes are used to detect identical, similar, or complementary nucleic acid sequences. Longer length probes can be obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies. Probes are substantially purified oligonucleotides that will hybridize under stringent conditions to at least optimally 12, 25, 50, 100, 150, 200, 250, 300, 350 or 400 consecutive sense strand nucleotide sequences of a sequence shown in Tables 5–15, 20, 22, 24, 26 and 29; or an anti-sense strand nucleotide sequence of a sequence shown in Tables 5–15, 20, 22, 24, 26 and 29; or of naturally occurring mutants of the sequences shown in Tables 5–15, 20, 22, 24, 26 and 29.

The full- or partial length native TAF polynucleotides sequences may be used to "pull out" similar (homologous) sequences (Ausubel et al., 1987), such as: (1) full-length or fragments of TAF polypeptide-encoding cDNAs from a cDNA library from any species (e.g. human, murine, feline, canine, bacterial, viral, retroviral, or yeast), (2) from cells or tissues, (3) variants within a species, and (4) homologs, orthologues and variants from other species. To find related sequences that may encode related genes, the probe may be designed to encode unique sequences or degenerate sequences. Sequences may also be TAF polypeptide-encoding genomic sequences including promoters, enhancer elements and introns; in the cases of EREs and PALs, non-polypeptide encoding polynucleotide sequences are preferred.

For example, ER coding region in another species may be isolated using such probes. A probe of about 40 bases is designed, based on human ERα (SEQ ID NO: 1), and made. To detect hybridizations, probes are labeled using, for example, radionuclides such as $^{32}P$ or $^{35}S$, or enzymatic labels such as alkaline phosphatase coupled to the probe via avidin-biotin systems. Labeled probes are used to detect nucleic acids having a complementary sequence to that of ERα in libraries of cDNA, genomic DNA or mRNA of a desired species.

Probes are also useful in arrays that allow for the simultaneous examination of multiple sequences.

Control Sequences

Control sequences are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

Operably-linked

Nucleic acid is operably-linked when placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous. However, enhancers do not have to be contiguous. Linking can be accomplished by conventional recombinant DNA methods.

Isolated Nucleic Acids

An isolated nucleic acid molecule is purified from the setting in which it is naturally found and is separated from at least one contaminant nucleic acid molecule. Isolated ER molecules, for example, are distinguished from the specific ER molecules in cells. However, an isolated ER molecule includes ER molecules contained in cells that ordinarily express ER where, for example, the nucleic acid molecule is in a chromosomal location different from that of natural cells.

Oligonucleotides

An oligonucleotide comprises a series of linked nucleotide residues having a sufficient number of nucleotide bases to be useful, such as in PCR reactions or as probes. A short oligonucleotide sequence may be based on or designed from a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. An oligonucleotide comprising a nucleic acid molecule less than 100 nt in length would further comprise at least 6 contiguous nucleotides of a sequence shown in Tables 5–15, 20, 22, 24, 26 and 29, or complements thereof. Oligonucleotides may be chemically synthesized.

Complementary Nucleic Acid Sequences, Binding

In another embodiment, an isolated nucleic acid molecule of the invention comprises a nucleic acid molecule that is a complement of a nucleotide sequence shown in Tables 5–15, 20, 22, 24, 26 and 29, or a portion of these sequences (e.g., fragments that can be used as a probes, primers or fragments that are active in themselves (such as in EREs) or encoding a biologically-active portion of a polypeptide (such as ERs))., A nucleic acid molecule complementary to a nucleotide sequence shown in Tables 5–15, 20, 22, 24, 26 and 29 is sufficiently complementary to a nucleotide sequence shown in Tables 5–15, 20, 22, 24, 26 and 29 that it can hydrogen bond with little or no mismatches to a nucleotide sequence shown in Tables 5–15, 20, 22, 24, 26 and 29, thereby forming a stable duplex.

"Complementary" refers to Watson-Crick or Hoogsteen base pairing between nucleotides of a nucleic acid molecule. "Binding" means the physical or chemical interaction between two nucleotides, polypeptides or compounds, or associated polypeptides, or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Nucleic acid fragments comprise at least 6 contiguous nucleic acids or at least 4 contiguous amino acids, a sufficient length to allow for specific hybridization in the case of nucleic acids or for specific recognition of an epitope in the case of amino acids, respectively, and are at most some portion less than a full-length sequence. Fragments may be derived from any contiguous portion of a nucleic acid or amino acid sequence.

Derivatives and Analogs

Derivatives are nucleic acid or amino acid sequences formed from native compounds either directly by modification or partial substitution. Analogs are nucleic acid or amino acid sequences that have a structure similar, but not identical, to the native compound but differ from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid. Derivatives or analogs of the nucleic acids or polypeptides of the invention include, but are not limited to, molecules comprising regions that are substantially homologous to nucleic acids or polypeptides by at least about 70%, 80%, or 95% identity (with a preferred identity of 80–95%) over a nucleic acid or amino acid sequence of identical size or when compared to an aligned sequence in which the alignment is done by a well-known algorithm in the art, or whose encoding nucleic acid is capable of hybridizing to the complement of a sequence encoding the aforementioned polypeptides under stringent, moderately stringent, or low stringent conditions (Ausubel et al., 1987).

Homology

A "homologous nucleic acid sequence", "homologous amino acid sequence," or variations thereof refer to sequences characterized by a homology at the nucleotide level or amino acid level. Homologous nucleotide sequences encode those sequences coding for isoforms of a polypeptide, such as an ER. Isoforms can be expressed in different tissues of the same organism as a result of, for example, alternative splicing. Alternatively, different genes can encode isoforms. Homologous nucleotide sequences also include mutations of sequences shown in Tables 5–15, 20, 22, 24, 26 and 29. A homologous nucleotide sequence does not, however, include the exact nucleotide sequence encoding the original starting sequence. Homologous nucleic acid sequences may encode conservative amino acid substitutions, as well as a polypeptide possessing a biological activity.

Open Reading Frames

The open reading frame (ORF) of a gene encodes a polypeptide(s) of interest. An ORF is a nucleotide sequence that has a start codon (ATG) and terminates with one of the three stop codons (TAA, TAG, or TGA). To achieve a unique sequence, preferable ORFs encode at least 50 amino acids.

Polypeptide-related Definitions

Proteins, Polypeptides and Peptides

The terms protein, peptide and polypeptide are well known in the art. A protein has an amino acid sequence that is longer than a peptide. A peptide contains 2 to about 50 amino acid residues. The term polypeptide includes proteins and peptides Mature A "mature" form of a polypeptide is the product of a naturally occurring polypeptide or precursor form. The naturally occurring polypeptide, precursor (pre-, pro-polypeptides) includes the full-length gene product, encoded by the corresponding genomic sequence or ORF. The "mature" form arises as a result of one or more processing steps as they may take place within a cell in which the gene product arises. Examples of processing steps include the cleavage of the N-terminal methionine residue encoded by the initiation codon of an ORF, or the signal peptide cleavage or leader sequence. Thus a mature form arising from a precursor polypeptide or polypeptide that has residues 1 to n, where residue 1 is the N-terminal methionine, would have residues 2 through n after removal of the N-terminal methionine. Alternatively, a mature form arising from a precursor polypeptide having residues 1 to n in which an N-terminal signal sequence from residue 1 to residue m is cleaved, would have the residues from residue m+1 to residue n remaining. A "mature" form of a polypeptide may arise from other post-translational modifications, such as glycosylation, myristoylation or phosphorylation. In general, a mature polypeptide may result from the operation of only one of these processes or a combination of any of them.

Purified Polypeptide

When the molecule is a purified polypeptide, the polypeptide is purified (1) to obtain at least 15 residues of N-terminal or internal amino acid sequence using a sequenator, or (2) to homogeneity by SDS-PAGE under non-reducing or reducing conditions using Coomassie blue or silver stain. Isolated polypeptides include those expressed heterologously in genetically-engineered cells or expressed in vitro, since at least one component of the polypeptide's natural environment is absent. Ordinarily isolated polypeptides are prepared by at least one purification step.

Active Polypeptide

An active polypeptide or fragment retains a biological and/or an immunological activity of native or naturally-occurring polypeptide. Immunological activity refers to the ability to induce the production of an antibody against an antigenic epitope possessed by a native polypeptide; biological activity refers to a function caused by a native polypeptide that excludes immunological activity. An ER (mutant or wild-type) biological function includes, for example, binding estrogen or anti-estrogens.

Polypeptide and Nucleic Acid Variants and Hybridization

Variant Polynucleotides, Genes and Recombinant Genes

The invention further encompasses nucleic acid molecules that differ from the nucleotide sequences shown in SEQ ID NOS: 4–15, 18 or 20 due to degeneracy of the genetic code and thus encode same polypeptides encoded by SEQ ID NOS: 4–15, 18 or 20.

In addition to the polypeptide sequences shown in 17, 21, 23, 25 and 27, DNA sequence polymorphisms that change the polypeptide amino acid sequences may exist within a population. For example, allelic variations among individuals exhibit genetic polymorphisms in polypeptides. The terms "gene" and "recombinant gene" refer to nucleic acid molecules comprising an open reading frame (ORF) encoding a polypeptide. Such natural allelic variations can typically result in 1–5% variance in the polypeptide. Any and all such nucleotide variations and resulting amino acid polymorphisms in the polypeptide, which are the result of natural allelic variation and leave intact polypeptide functional activity, are within the scope of the invention.

Moreover, polypeptides from other species that have a nucleotide sequence that differs from a sequence shown in Tables 5–15, 20, 22, 24, 26 and 29 are contemplated. Nucleic acid molecules corresponding to natural allelic variants and homologs of polypeptide cDNAs can be isolated based on their homology to a sequence shown in Tables 5–15, 20, 22, 24, 26 and 29 using cDNA-derived probes to hybridize to homologous polypeptide sequences under stringent conditions.

"Polypeptide variant polynucleotide" or "polypeptide variant nucleic acid sequence" means a nucleic acid molecule which encodes an active polypeptide that (1) has at least about 80% nucleic acid sequence identity with a nucleotide acid sequence encoding a full-length native polypeptide, (2) a full-length native polypeptide lacking the signal peptide, (3) an extracellular domain of a polypeptide, with or without the signal peptide, or (4) any other fragment of a full-length polypeptide. A polypeptide variant polynucleotide will have at least about 80% nucleic acid sequence identity, more preferably at least about 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence encoding a full-length native polypeptide. A polypeptide variant polynucleotide may encode full-length native polypeptide lacking the signal peptide, an extracellular domain of a polypeptide, with or without the signal sequence, or any other fragment of a full-length polypeptide. Variants do not encompass the native nucleotide sequence.

"Percent (%) nucleic acid sequence identity" with respect to polypeptide-encoding nucleic acid sequences is defined as the percentage of nucleotides in the polypeptide sequence of interest that are identical with the nucleotides in a candidate sequence, after aligning the sequences and introducing gaps, if necessary, to achieve the maximum percent sequence identity. Alignment can be achieved in various ways well-known in the art; for instance, using publicly available software such as BLAST, BLAST-2, ALIGN or Megalign (DNASTAR) software. Those skilled in the art can determine appropriate parameters for measuring alignment, including any necessary algorithms to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\% \text{ nucleic acid sequence identity} = W/Z \cdot 100$$

where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

Conservative Mutations

In addition to naturally occurring allelic variants, changes can be introduced by mutation into the sequences shown in Tables 5–15, 20, 22, 24, 26 and 29 that incur alterations in the amino acid sequences of polypeptide but do not alter polypeptide function. For example, nucleotide substitutions leading to amino acid substitutions at "non-essential" amino acid residues can be made in those sequences found in Tables 17, 21, 23, 25 and 27. A "non-essential" amino acid residue is a residue that can be altered from the wild-type sequences of the polypeptide without altering their biological activity, whereas an "essential" amino acid residue is required for biological activity.

Useful conservative substitutions are shown in Table A, "Preferred substitutions." Conservative substitutions whereby an amino acid of one class is replaced with another amino acid of the same type fall within the scope of the subject invention so long as the substitution does not materially alter the biological activity of the compound. If such substitutions result in a change in biological activity, then more substantial changes, indicated in Table B as exemplary are introduced and the products screened for polypeptide biological activity.

TABLE A

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect (1) the structure of the polypeptide backbone, such as a β-sheet or α-helical conformation, (2) the charge or (3) hydrophobicity, or (4) the bulk of the side chain of the target site can modify polypeptide function or immunological identity. Residues are divided into groups based on common side-chain properties as denoted in Table B. Non-conservative substitutions entail exchanging a member of one of these classes for another class. Substitutions may be introduced into conservative substitution sites or more preferably into non-conserved sites.

TABLE B

| Amino acid classes | |
|---|---|
| Class | Amino acids |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce polypeptide variants (Ausubel et al., 1987).

Anti-sense Nucleic Acids

Using antisense and sense polypeptide oligonucleotides can prevent polypeptide expression. These oligonucleotides bind to target nucleic acid sequences, forming duplexes that block transcription or translation of the target sequence by enhancing degradation of the duplexes, terminating prematurely transcription or translation, or by other means.

Antisense or sense oligonucleotides are singe-stranded nucleic acids, either RNA or DNA, which can bind target polypeptide mRNA (sense) or polypeptide DNA (antisense) sequences. Anti-sense nucleic acids can be designed according to Watson and Crick or Hoogsteen base pairing rules. The anti-sense nucleic acid molecule can be complementary to the entire coding region of polypeptide mRNA, but more preferably, to only a portion of the coding or noncoding region of polypeptide mRNA. For example, the anti-sense oligonucleotide can be complementary to the region surrounding the translation start site of polypeptide mRNA. Antisense or sense oligonucleotides may comprise a fragment of the polypeptide coding region of at least about 14 nucleotides, preferably from about 14 to 30 nucleotides. In general, antisense RNA or DNA molecules can comprise at least 5, 10, 15, 20, 25, 30, 35, 40, 45, 50, 55, 60, 65, 70, 75, 80, 85, 90, 95, 100 bases in length or more. Methods to derive antisense or sense oligonucleotides are well described (Stein and Cohen, 1988; van der Krol et al., 1988a).

Examples of modified nucleotides that can be used to generate the anti-sense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, -methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the anti-sense nucleic acid can be produced using an expression vector into which a nucleic acid has been sub-cloned in an anti-sense orientation such that the transcribed RNA will be complementary to a target nucleic acid of interest.

To introduce antisense or sense oligonucleotides into target cells (cells containing a target nucleic acid sequence), any gene transfer method may be used. Examples of gene transfer methods include (1) biological, such as gene transfer vectors like Epstein-Barr virus or conjugating the exogenous DNA to a ligand-binding molecule, (2) physical, such as electroporation and injection, and (3) chemical, such as $CaPO_4$ precipitation and oligonucleotide-lipid complexes. Table D summarizes many such useful techniques.

An anti-sense nucleic acid molecule may be α-anomeric. An α-anomeric nucleic acid molecule forms specific double-stranded hybrids with complementary RNA in which, contrary to the usual a-units, the strands run parallel to each other (Gautier et al., 1987). The anti-sense nucleic acid molecule can also comprise a 2'-o-methylribonucleotide (Inoue et al., 1987a) or a chimeric RNA-DNA analog (Inoue et al., 1987b).

An anti-sense nucleic acid may be a catalytic RNA molecule with ribonuclease activity, a ribozyme. For example, hammerhead ribozymes (Haseloff and Gerlach, 1988) can be used to catalytically cleave polypeptide mRNA transcripts and thus inhibit translation. A ribozyme specific for a polypeptide-encoding nucleic acid can be designed based on the nucleotide sequence of a polypeptide cDNA (i.e., the sequences of SEQ ID NOS shown in Tables 4–15, 18). For example, a derivative of Tetrahymena L-19 IVS RNA can be constructed in which the nucleotide sequence of the active site is complementary to the nucleotide sequence to be cleaved in a polypeptide-encoding mRNA (Cech et al., U.S. Pat. No. 5,116,742, 1992; Cech et al., U.S. Pat. No. 4,987,071, 1991). Polypeptide mRNA can also be used to select a catalytic RNA having a specific ribonuclease activity from a pool of RNA molecules (Bartel and Szostak, 1993).

Alternatively, polypeptide expression can be inhibited by targeting nucleotide sequences complementary to the regulatory region of a polypeptide (e.g., polypeptide promoter and/or enhancers) to form triple helical structures that prevent transcription of the polypeptide in target cells (Helene, 1991; Helene et al., 1992; Maher, 1992).

Modifications of antisense and sense oligonucleotides can augment their effectiveness. Modified sugar-phosphodiester bonds or other sugar linkages (WO 91/06629, 1991) increase in vivo stability by conferring resistance to endogenous nucleases without disrupting binding specificity to target sequences. Other modifications can increase the affinities of the oligonucleotides for their targets, such as covalently linked organic moieties (WO 90/10448, 1990) or poly-(L)-lysine. Other attachments modify binding specificities of the oligonucleotides for their targets, including metal complexes or intercalating (e.g. ellipticine) and alkylating agents.

For example, the deoxyribose phosphate backbone can be modified to generate peptide nucleic acids (Hyrup and Nielsen, 1996). "Peptide nucleic acids" (PNAs) refer to nucleic acid mimics in that the deoxyribose phosphate backbone is replaced by a pseudopeptide backbone, and only the four natural nucleobases are retained. The neutral backbone of PNAs allows for specific hybridization to DNA and RNA under conditions of low ionic strength. PNA oligomers can be synthesized using solid phase peptide synthesis protocols (Hyrup and Nielsen, 1996; Perry-O'Keefe et al., 1996).

The oligonucleotide may include other appended groups such as peptides (e.g., for targeting host cell receptors in vivo), or agents facilitating transport across the cell membrane (Lemaitre et al., 1987; Letsinger et al., 1989) or the blood-brain barrier (Pardridge and Schimmel, WO89/10134, 1989). In addition, oligonucleotides can be modified with hybridization-triggered cleavage agents (van der Krol et al., 1988b) or intercalating agents (Zon, 1988). The oligonucleotide may be conjugated to another molecule, e.g., a peptide, a hybridization triggered cross-linking agent, a transport agent, a hybridization-triggered cleavage agent, and the like.

Polypeptides

The invention pertains to isolated polypeptides and biologically-active portions derivatives, fragments, analogs or homologs thereof. Polypeptides may be isolated from cells and tissues, produced by recombinant DNA techniques or chemical synthesis.

Polypeptides

A polypeptide includes an amino acid sequence of a polypeptide whose sequences are provided in Tables 17, 21, 23, 25 and 27. The invention also includes a mutant or variant polypeptide any of whose residues may be changed from the corresponding residues shown in Tables 17, 21, 23, 25 and 27 while still encoding an active polypeptide, or a functional fragment.

Polypeptide Variants

In general, a polypeptide variant that preserves polypeptide-like function and includes any variant in which residues at a particular position in the sequence have been substituted by other amino acids, and further includes the possibility of inserting an additional residue or residues between two residues of the parent polypeptide as well as the possibility of deleting one or more residues from the parent sequence. Preferably, the substitution is a conservative substitution (Table A).

"Polypeptide variant" means an active polypeptide having at least: (1) about 80% amino acid sequence identity with a full-length native polypeptide sequence, (2) a polypeptide sequence lacking a signal peptide, (3) an extracellular domain of a polypeptide, with or without a signal peptide, or (4) any other fragment of a full-length polypeptide sequence. For example, polypeptide variants include those wherein one or more amino acid residues are added or deleted at the N- or C-terminus of the full-length native amino acid sequence. A polypeptide variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% a sequence identity and most preferably at least about 99% amino acid sequence identity with a full-length native sequence polypeptide sequence. Ordinarily, polypeptide variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in a polypeptide sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNASTAR) can be used to align polypeptide sequences. Those skilled in the art will determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y \cdot 100$ where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Isolated/Purified Polypeptides

An "isolated" or "purified" polypeptide, polypeptide or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preferably, the polypeptide is purified to a sufficient degree to obtain at least 15 residues of N-terminal or internal amino acid sequence. To be substantially isolated, preparations having less than 30% by dry weight of contaminants, more preferably less than 20%, 10% and most preferably less than 5% contaminants. An isolated, recombinantly-produced polypeptide or biologically active portion is preferably substantially free of culture medium, i.e., culture medium represents less than 20%, more preferably less than about 10%, and most preferably less than about 5% of the volume of the polypeptide preparation. Examples of contaminants include cell debris, culture media, and substances used and produced during in vitro synthesis of polypeptide.

Biologically Active

Biologically active portions of polypeptide include peptides comprising amino acid sequences sufficiently homologous to, or derived from, the amino acid sequences of a polypeptide sequences shown in Tables 17, 21, 23, 25 and 27 that include fewer amino acids than the full-length polypeptide and exhibit at least one activity of a polypeptide. Biologically active portions comprise a domain or motif with at least one activity of native polypeptide. For example, activities include binding estrogens, binding anti-estrogens for ER, or activating transcription. A biologically active portion of a polypeptide can be a polypeptide that is 10, 25, 50, 100 or more amino acid residues in length. Other biologically active portions, in which other regions of the polypeptide are deleted, can be prepared by recombinant techniques and evaluated for one or more of the functional activities of a native polypeptide.

Biologically active portions of a polypeptide may have an amino acid sequence of a sequence shown in Tables 17, 21, 23, 25 and 27, or substantially homologous to those sequences, and retain the functional activity of the corresponding polypeptide of those shown in Tables 17, 21, 23, 25 and 27, yet differ in amino acid sequence due to natural allelic variation or mutagenesis. Other biologically active polypeptides may comprise an amino acid sequence at least 45% homologous to an amino acid sequence shown in Tables 16,17 19, and retain the functional activity of native polypeptide. Homology can be determined as described in polypeptide variants, above.

Polypeptide Recombinant Expression Vectors and Host Cells

Vectors are tools used to shuttle DNA between host cells or as a means to express a nucleotide sequence. They may comprise simple plasmids, bacteria or viruses. Some vectors function only in prokaryotes or eukaryotes while others function in both. Inserting the DNA of interest, such as a polypeptide nucleotide sequence or a fragment, is accomplished by ligation techniques (especially in plasmids), transposon insertion and/or mating protocols well known to the skilled artisan. Such DNA is inserted such that its integration does not disrupt any necessary components of the vector. In the case of vectors that are used to express an inserted DNA polypeptide, the introduced DNA is operably linked to the vector elements that govern its transcription and/or translation.

Vectors can be divided into two general classes. Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors such as the TAS's of the invention. Operably-linking a polypeptide or anti-sense construct to an inducible promoter can control the expression of a polypeptide or fragments, or anti-sense constructs.

Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses and adeno-associated viruses); other expression vectors can also be used.

Recombinant expression vectors that comprise a polypeptide (or fragment(s)) regulate a polypeptide transcription by exploiting one or more host cell-responsive (or that can be manipulated in vitro) regulatory sequences that is operably-linked to polypeptide.

Vectors can be introduced in a variety of organisms and cells, including both prokaryotes and eukaryotes. Alternatively, the vectors can be transcribed and translated in vitro, for example using T7 promoter regulatory sequences and T7 polymerase.

Vector choice is dictated by the organism or cells being used and the desired fate of the vector. Vectors may replicate once or more in target cells or may be "suicide" vectors. In general, plasmid vectors comprise signal sequences, origins of replication, marker genes, enhancer elements, promoters, and transcription termination sequences. Plasmid vectors often use a selectable marker to facilitate identifying those cells that have incorporated the vector. Many selectable markers are well known in the art for the use with prokaryotes, usually antibiotic-resistance genes or the use of autotrophy and auxotrophy mutants. Table E summarizes many of the available and commonly used markers.

"Host cell" and "recombinant host cell" are used interchangeably. Such terms refer not only to a particular subject cell but also to the progeny or potential progeny of such a cell. Because certain modifications may occur in succeeding generations due to either mutation or environmental influences, such progeny may not, in fact, be identical to the parent cell, but are still included within the scope of the term.

Methods of eukaryotic cell transfection and prokaryotic cell transformation are well known in the art. The choice of host cell dictates the preferred technique for introducing the nucleic acid of interest. Table D summarizes many known techniques in the art. Introduction of nucleic acids into an organism may also be done with ex vivo techniques that use an in vitro method of transfection, as well as established genetic techniques, if any, for that particular organism.

TABLE D

Common transfection/transformation techniques

| Cells | Methods | References |
|---|---|---|
| Prokaryotes (bacteria) | Calcium chloride | (Cohen et al., 1972; Hanahan, 1983; Mandel and Higa, 1970) |
| | Electroporation | (Shigekawa and Dower, 1988) |
| Eukaryotes Mammalian cells | Calcium phosphate transfection | N-(2-Hydroxyethyl)piperazine-N'-(2-ethanesulfonic acid (HEPES) buffered saline solution (Chen and Okayama, 1988; Graham and van der Eb, 1973; Wigler et al., 1978) |
| | | BES (N,N-bis(2-hydroxyethyl)-2-aminoethanesulfonic acid) buffered solution (Ishiura et al., 1982) |
| | Diethylaminoethyl (DEAE)-Dextran transfection | (Fujita et al., 1986; Lopata et al., 1984; Selden et al., 1986) |
| | Electroporation | (Neumann et al., 1982; Potter, 1988; Potter et al., 1984; Wong and Neumann, 1982) |
| | Cationic lipid reagent transfection | (Elroy-Stein and Moss, 1990; Felgner et al., 1987; Rose et al., 1991; Whitt et al., 1990) |
| | Retroviral | Production exemplified by (Cepko et al., 1984; Miller and Buttimore, 1986; Pear et al., 1993) |
| | | Infection in vitro and in vivo: (Austin and Cepko, 1990; Bodine et al., 1991; Fekete and Cepko, 1993; Lemischka et al., 1986; Turner et al., 1990; Williams et al., 1984) |
| | Polybrene | (Chaney et al., 1986; Kawai and Nishizawa, 1984) |
| | Microinjection | (Capecchi, 1980) |
| | Protoplast fusion | (Rassoulzadegan et al., 1982; Sandri-Goldin et al., 1981; Schaffner, 1980) |
| Insect cells (in vitro) | Baculovirus systems | (Luckow, 1991; Miller, 1988; O'Reilly et al., 1992) |
| Yeast | Electroporation | (Becker and Guarente, 1991) |
| | Lithium acetate | (Gietz et al., 1998; Ito et al., 1983) |
| | Spheroplast fusion | (Beggs, 1978; Hinnen et al., 1978) |
| Plant cells (general reference: (Hansen and Wright, 1999)) | Agrobacterium transformation | (Bechtold and Pelletier, 1998; Escudero and Hohn, 1997; Hansen and Chilton, 1999; Touraev and al., 1997) |
| | Biolistics (microprojectiles) | (Finer et al., 1999; Hansen and Chilton, 1999; Shillito, 1999) |
| | Electroporation (protoplasts) | (Fromm et al., 1985; Ou-Lee et al., 1986; Rhodes et al., 1988; Saunders et al., 1989) |
| | | May be combined with liposomes (Trick and al., 1997) |
| | Polyethylene glycol (PEG) treatment | (Shillito, 1999) |
| | Liposomes | May be combined with electroporation (Trick and al., 1997) |
| | in planta microinjection | (Leduc and al., 1996; Zhou and al., 1983) |
| | Seed imbibition | (Trick and al., 1997) |
| | Laser beam | (Hoffman, 1996) |
| | Silicon carbide whiskers | (Thompson and al., 1995) |

TABLE E

Useful selectable markers for eukaryote cell transfection

| Selectable Marker | Selection | Action | Reference |
|---|---|---|---|
| Adenosine deaminase (ADA) | Media includes 9-β-D-xylofuranosyl adenine (Xyl-A) | Conversion of Xyl-A to Xyl-ATP, which incorporates into nucleic acids, killing cells. ADA detoxifies | (Kaufman et al., 1986 |

TABLE E-continued

Useful selectable markers for eukaryote cell transfection

| Selectable Marker | Selection | Action | Reference |
|---|---|---|---|
| Dihydrofolate reductase (DHFR) | Methotrexate (MTX) and dialyzed serum (purine-free media) | MTX competitive inhibitor of DHFR. In absence of exogenous purines, cells require DHFR, a necessary enzyme in purine biosynthesis. | (Simonsen and Levinson, 1983) |
| Aminoglycoside phosphotransferase ("APH", "neo", "G418") | G418 | G418, an aminoglycoside detoxified by APH, interferes with ribosomal function and consequently, translation. | (Southern and Berg, 1982) |
| Hygromycin-B-phosphotransferase (HPH) | hygromycin-B | Hygromycin-B, an aminocyclitol detoxified by HPH, disrupts polypeptide translocation and promotes mistranslation. | (Palmer et al., 1987) |
| Thymidine kinase (TK) | Forward selection (TK+): Media (HAT) incorporates aminopterin. Reverse selection (TK−): Media incorporates 5-bromodeoxyuridine (BrdU). | Forward: Aminopterin forces cells to synthesze dTTP from thymidine, a pathway requiring TK. Reverse: TK phosphorylates BrdU, which incorporates into nucleic acids, killing cells. | (Littlefield, 1964) |

A host cell, prokaryotic or eukaryotic, can be used to produce a polypeptide in culture. To accomplish in vitro expression of a polypeptide, a host cell containing a recombinant expression vector encoding a polypeptide is expressed, when cultured in a suitable medium. The polypeptide may then be isolated from the media or culture.

Transgenic Animals

Transgenic animals are useful for studying the function and/or activity of a polypeptide and for identifying and/or evaluating modulators of a polypeptide activity. They are also useful for providing disease models. "Transgenic animals" are non-human animals, preferably mammals, more preferably rodents such as rats or mice, in which one or more of the cells include a transgene. Other transgenic animals include primates, sheep, dogs, cows, goats, chickens, amphibians, etc. A "transgene" is exogenous DNA that is integrated into the genome of a cell from which a transgenic animal develops and that remains in the genome of the mature animal. Transgenes preferably direct the expression of an encoded gene product in one or more cell types or tissues, preventing expression of a naturally encoded gene product in one or more cell types or tissues (a "knockout" transgenic animal), over-expressing an encoded gene, or serving as a marker or indicator of an integration, chromosomal location, or region of recombination (e.g. Cre/loxP mice). A "homologous recombinant animal" is a non-human animal, such as a rodent, in which an endogenous polypeptide has been altered by an exogenous DNA molecule that recombines homologously with an endogenous polypeptide in a (e.g. embryonic) cell prior to development the animal. Host cells with an exogenous polypeptide can be used to produce non-human transgenic animals, such as fertilized oocytes or embryonic stem cells into which a polypeptide coding sequence has been introduced. Such host cells can then be used to create non-human transgenic animals or homologous recombinant animals.

Approaches to Transgenic Animal Production

A transgenic animal can be created by introducing a polypeptide into the male pronuclei of a fertilized oocyte (e.g., by microinjection, retroviral infection, etc.) and allowing the oocyte to develop in a pseudopregnant female foster animal (pffa). The polypeptide sequences (encoded by a sequence shown in Tables 5–15, 20, 22, 24, 26 and 29) can be introduced as a transgene into the genome of a non-human animal. Alternatively, a homolog of a polypeptide can be used as a transgene. Intronic sequences and polyadenylation signals can also be included in the transgene to increase its expression. Tissue-specific regulatory sequences can be operably-linked to the polypeptide transgene to direct expression of polypeptide to particular cells. Methods for generating transgenic animals via embryo manipulation and microinjection, particularly animals such as mice, have become conventional in the art (Evans et al., U.S. Pat. No. 4,870,009, 1989; Hogan, 0879693843, 1994; Leder and Stewart, U.S. Pat. No. 4,736,866, 1988; Wagner and Hoppe, U.S. Pat. No. 4,873,191, 1989). Other non-mice transgenic animals may be made by similar methods. A transgenic founder animal, which can be used to breed additional transgenic animals, can be identified based upon the presence of the transgene in its genome and/or expression of the transgene mRNA in tissues or cells of the animals. Transgenic animals can be bred to other transgenic animals carrying other transgenes.

Vectors for Transgenic Animal Production

To create a homologous recombinant animal, a plasmid vector containing at least a portion of a polypeptide into which a deletion, addition or substitution has been introduced to thereby alter, e.g., functionally disrupt, the polypeptide. Alternatively, regulatory sequences can be introduced by using a plasmid vector containing at least a portion of a regulatory sequence. The polypeptide can be a mouse gene or a homolog. In one approach, a knockout vector functionally disrupts an endogenous polypeptide gene upon homologous recombination, and thus a non-functional polypeptide, if any, is expressed.

Alternatively, the plasmid vector can be designed such that, upon homologous recombination, an endogenous polynucleotide is mutated or otherwise altered but still encodes functional polypeptide (e.g., the upstream regulatory region can be altered to thereby alter the expression of an endogenous polypeptide). In this type of homologous recombination vector, the altered portion of a polypeptide are flanked at the N- and C-termini by additional nucleic acids of an endogenous polynucleotide sequence to allow for homologous recombination to occur between the exogenous polypeptide-encoding polynucleotide carried by the vector and an endogenous polynucleotide sequence in an embryonic stem cell. Typically, several kilobases of flanking DNA (both at the N- and C-termini) are included in the vector (Thomas and Capecchi, 1987). The vector is then introduced into an embryonic stem cell line, and cells in which the introduced polypeptide has homologously-recombined with an endogenous polypeptide are selected (Li et al., 1992).

Introduction of Polypeptide Transgene Cells During Development

Selected cells are then injected into a blastocyst of an animal to form aggregation chimeras (Bradley, 1987). A chimeric embryo can then be implanted into a suitable pffa and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are well-described (Berns et al., WO 93/04169, 1993; Bradley, 1991; Kucherlapati et al., WO 91/01140, 1991; Le Mouellic and Brullet, WO 90/11354, 1990).

Alternatively, transgenic animals that contain selected systems that allow for regulated expression of the transgene can be produced. For example, the cre/loxP recombinase system of bacteriophage P1 (Lakso et al., 1992) or the FLP recombinase system of *Saccharomyces cerevisiae* (O'Gorman et al., 1991) may be used. In cre/loxP recombinase systems, animals containing transgenes encoding both the Cre recombinase and a selected polypeptide are required. Such animals can be produced as "double" transgenic animals, by mating an animal containing a transgene encoding a selected polypeptide to another containing a transgene encoding a recombinase. The TAS's of the invention are preferred for regulated expression in many transgenic animals and may be used in transgenic animals in which another expression system controls a separate polynucleotide sequence.

Transgenic animal clones can also be produced (Wilmut et al., 1997). In brief, a cell from a transgenic animal can be isolated and induced to exit the growth cycle and enter Go phase. The quiescent cell can then be fused to an enucleated oocyte from an animal of the same species from which the quiescent cell is isolated. The reconstructed oocyte is then cultured to develop to a morula or blastocyte and then transferred to a pffa. The offspring borne of this female foster animal will be a clone of the "parent" transgenic animal.

Pharmaceutical Compositions

The polypeptide nucleic acid molecules, polypeptides, and their derivatives, fragments, analogs and homologs, can be incorporated into pharmaceutical compositions. A "pharmaceutically acceptable carrier" includes any and all solvents, dispersion media, coatings, antibacterial and antifungal agents, isotonic and absorption delaying agents, and the like that are compatible with pharmaceutical administration (Gennaro, 2000). Preferred examples of such carriers or diluents include, but are not limited to, water, saline, Ringer's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

General Considerations

A pharmaceutical composition is formulated to be compatible with the intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose-vials made of glass or plastic.

Injectable Formulations

To access target tissues, injection can provide a direct and facile route, especially for tissue below the skin. Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition. Compositions that delay absorption include agents such as aluminum monostearate and gelatin.

Sterile injectable solutions can be prepared by incorporating the active compound (e.g., a polypeptide or nucleic acid) in an appropriate solvent with one or a combination of ingredients. Generally, dispersions are prepared by incorporating the active compound into a sterile vehicle that contains a basic dispersion medium and any other required ingredients. Sterile powders for the preparation of sterile injectable solutions methods of preparation include vacuum drying and freeze-drying that yield a powder containing the active ingredient and any desired ingredient from a sterile solutions.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRJMO-GEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

Carriers

Active compounds may be prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid (ALZA Corporation; Mountain View, Calif. and NOVA Pharmaceuticals, Inc.; Lake Elsinore, Calif.; or prepared by one of skill in the art). Liposomal suspensions can also be used as pharmaceutically acceptable carriers. These can be prepared according to well-accepted methods (Eppstein et al., U.S. Pat. No. 4,522,811, 1985).

Unit Dosage

Oral formulations or parenteral compositions in unit dosage form can be created to facilitate administration and dosage uniformity. Unit dosage form refers to physically discrete units suited as single dosages for a subject to be treated, containing a therapeutically effective quantity of active compound in association with the required pharmaceutical carrier. The specification for unit dosage forms are dictated by, and directly dependent on, the unique characteristics of the active compound and the particular desired therapeutic effect, and the inherent limitations of compounding the active compound.

Gene Therapy Compositions

The nucleic acid molecules of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., 1994). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Dosage

The pharmaceutical compositions and methods of the present invention may further comprise other therapeutically active compounds that are usually applied in the treatment of adipose-related pathologies. Especially relevant to the invention is tamoxifen and OHT administration.

In the treatment or prevention of conditions which require modulation of a polypeptide, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to a patient to be treated. The compounds may be administered on a regimen of 1 to 4 times per day, preferably once or twice per day. For tamoxifen used in chemoprevention of breast cancer, a preferred dosage would be 5 mg/day. When tamoxifen is used as post-operative therapy for breast cancer patients, a preferred does is 10–20 mg/day for several years. The range of doeses is 2–15 mg/day for chemoprevention and 5–50 mg/day for post-operative patients. An appropriate dose of 4-hydroxytamoxifen would be 25–250 µg/day for chemoprevention and 100–1000 µg for patients after breast surgery.

It will be understood, however, that the specific dose level and frequency of dosage for any particular patient may be varied and depends upon a variety of factors, including the activity of the specific compound employed, the metabolic stability and length of action of that compound, the age, body weight, general health, sex, diet, mode and time of administration, rate of excretion, drug combination, the severity of the particular condition, and the host undergoing therapy.

Kits for Pharmaceutical Compositions

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit long-term storage without losing the active components' functions.

Kits may also include reagents in separate containers that facilitate the execution of a specific test, such as diagnostic tests or tissue typing. For example, DNA templates and suitable primers may be supplied for internal controls.

(a) Containers or Vessels

The reagents included in kits can be supplied in containers of any sort such that the life of the different components are preserved and are not adsorbed or altered by the materials of the container. For example, sealed glass ampules may contain lyophilized luciferase or buffer that have been packaged under a neutral, non-reacting gas, such as nitrogen. Ampules may consist of any suitable material, such as glass, organic polymers, such as polycarbonate, polystyrene, ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

The following examples are intended to illustrate the present invention without limitation.

EXAMPLES

Example 1

Materials and Methods

Plasmid Constructs

Oligonucleotides used in the Examples can be found in Table 30 (EREs and PAL sequences are indicated by underlining).

To create p(ERE)$_4$-TATA-LUC (LUC, luciferase), an ERE-containing promoter fragment was excised from the 4.75 kb vector, p(ERE)$_4$-TATA-CAT (CAT, chloramphenicol transferase; (Mattick et al., 1997)) by digesting with HindIII and NcoI and subcloned into the pGL3-Basic vector (Promega; Madison, Wis.) also digested with HindIII and NcoI.

To create the ATL2 and 4 plasmid series, the p(ERE)$_4$-TATA-LUC plasmid was digested with HindIII and partially with XbaI. The DNA was separated on agarose gel and a 4.75 Kb fragment was isolated and used as a vector. To create ATL2/cERE-LUC, (ATL refers to the cERE from the *Xenopus vitellogenin* A gene and its TATA box, driving luciferase expression in this construct) the cERE-F and cERE-R (SEQ ID NOS:27–28) oligonucleotides were synthesized, annealed and subcloned into p(ERE)$_4$-TATA-LUC. Similarly, ATL2/pS2ERE-LUC was constructed using oligonucleotides pS2-F and pS2-R (SEQ ID NOS:29–30). ATL2/PAL-LUC was constructed using pS2PAL-F and pS2PAL-R (SEQ ID NOS:31–32).

To construct pATL4/cERE-LUC, two pairs of oligonucleotides were prepared, cERE1st-F, cERE1st-R, and cERE2nd-F, cERE2nd-R (SEQ ID NOS:33–36). The primers were phosphorylated and annealed separately (first pair, and then second pair), and then subcloned together into the p(ERE)$_4$-TATA-LUC 4.75 kb vector. The same strategy was used to create ATL4/PAL-LUC using two pairs of oligonucleotides, PAL1st-F, PAL1st-R, and PAL2nd-F, PAL2nd-R (SEQ ID NOS:37–40). To generate pATL8/PAL-LUC, two pairs of oligonucleotides, ATL8-F1, ATL8-R1, and ATL8-F2, ATL8-R2 (SEQ ID NOS:41–44) were phosphorylated and annealed separately (first pair and then second pair), then cloned into the 4.8 kb ATL4/PAL-LUC vector digested with NheI and HindIII. A similar strategy was used to create the ATL8/cERE-LUC using two pairs of oligonucleotides, ATL8/cERE-F1, ATL8/cERER1 and ATLS/cERE-F2, ATL8/cERE-R2 (SEQ ID NOS:45–48) using the 4.8 kb ATL4/cERE-LUC vector digested with NheI and HindIII.

TABLE 30

Oligonucleotides used to engineer constructs

| Designation | Sequence | | SEQ ID NO |
|---|---|---|---|
| cERE-F | agctt<u>aggtc=actgtgacct</u>=atcaagatat cgagat<u>aggt=cactgtgacc</u>=tatcgact | 58 | 27 |
| cBRE-R | ctagagtcga t<u>aggtcacag=tgacct</u>atct cgatatcttg at<u>aggtcaca=gtgacct</u>a | 58 | 28 |
| pS2-F | agctt<u>aggtc=actgtggccc</u>=atcaagatat cgagat<u>aggt=cactgtggcc</u>=catcgact | 58 | 29 |
| pS2-R | ctagagtcga t<u>gggccacag=tgacct</u>atct cgatatcttg at<u>gggccaca=gtgacct</u>a | 58 | 30 |
| pS2PAL-F | agctt<u>gggcc=actgtggccc</u>=atcaagatat cgagat<u>gggc=cactgtggcc</u>=catcgact | 58 | 31 |
| pS2PAL-R | ctagagtcga t<u>gggccacag=tggccc</u>atct cgatatcttg at<u>gggccaca=gtggccc</u>a | 58 | 32 |
| cERE1st-F | agctt<u>aggtc=actgtgacct</u>=atcaagatat cgagat<u>aggt=cactgtgacc</u>=tatcgacagg | 60 | 33 |
| cERE1st-R | aattcctgtc gat<u>aggtcac=agtgacct</u>at ctcgatatct tgat<u>aggtca=cagtgaccta</u> | 60 | 34 |

TABLE 30-continued

Oligonucleotides used to engineer constructs

| Designation | Sequence | | SEQ ID NO |
|---|---|---|---|
| cERE2nd-F | aattcac<u>agg=tcactgtgac=c</u>tatcaagat atcgagat<u>ag=gtcactgtga=cctat</u>cgact | 60 | 35 |
| cERE2nd-R | ctagagtcga t<u>aggtcacag=tgacct</u>atct cgatatcttg at<u>aggtcaca=gtgacct</u>gtg | 60 | 36 |
| PAL1st-F | agctt<u>gggcc=actgtgccc</u>=atcaagatat cgagat<u>gggc=cactgtggcc=c</u>atcgacagg | 60 | 37 |
| PAL1st-R | aattcctgtc gat<u>gggccac=agtggccc</u>at ctcgatatct tgat<u>gggcca=cagtggccc</u>a | 60 | 38 |
| PAL2nd-F | aattcac<u>ggg=ccactgtggc=cc</u>atcaagat atcgagat<u>gg=gccactgtgg=ccc</u>atcgact | 60 | 39 |
| PAL2nd-R | ctagagtcga t<u>gggccacag=tggccc</u>atct cgatatcttg at<u>gggccaca=gtggccc</u>gtg | 60 | 40 |
| ATL8-F1 | ctagc<u>gggcc=actgtggccc</u>=tgacaactag taagtc<u>gggc=cactgtggcc=c</u>gacgtacta tc | 60 62 | 41 |
| ATL8-R1 | tcgagatagt acgtc<u>gggcc=acagtggccc</u>=gacttactag ttgtc<u>gggc=cacagtggcc cg</u> | 60 62 | 42 |
| ATL8-F2 | tcgag<u>gggcc=actgtggccc</u>=tagagctgca ggtatc<u>gggc=cactgtggcc=c</u>tagttcatt aa | 60 62 | 43 |
| ATL8-R2 | agctttaatg aacta<u>gggcc=acagtggccc</u>=gatacctgca gctctag<u>ggc=cacagtggcc cc</u> | 60 62 | 44 |
| ATL8/cERE-F1 | ctagc<u>aggtc=actgtgacct</u>=tgacaactag taagtc<u>aggt=cactgtgacc=t</u>gacgtacta tc | 60 62 | 45 |
| ATL8/cERE-R1 | tcgagatagt acgtc<u>aggtc=acagtgacct</u>=gacttactag ttgtc<u>aggt=cacagtgacc tg</u> | 60 62 | 46 |
| ATL8/cERE-F2 | tcgag<u>aggtc=actgtgacct</u>=tagagctgca ggtatc<u>aggt=cactgtgacc=t</u>tagttcatt aa | 60 62 | 47 |
| ATL8/cERE-R2 | agctttaatg aacta<u>aggtc=acagtgacct</u>=gatacctgca gctctaa<u>ggt=cacagtgacc tc</u> | 60 62 | 48 |
| N-vp16-128aa-P1 | cggggtaccg gccacggacc atgtccgcgt acagccgcgc gcgtac | 46 | 49 |
| N-vp16-XbaI-P2 | ctagtctaga cccaccgtac tcgtcaattc c | 31 | 50 |
| N-vp16-78aa-P1 | cggggtaccg gccacggacc atgacggccc ccccgaccga tgtc | 31 | 51 |
| N-hER-NheI-P1 | tctagctagc atgaccatga ccctccacac c | 31 | 52 |
| N-hER-NotI-P2 | ataagaatgc ggccgcggcg ttgaactc | 28 | 53 |
| c-vp16-128aa-P1 | atcgggtacc tccgcgtaca gccgcgcgcg tac | 33 | 54 |
| c-vp16-P2 | cttatcatgt ctggatcctc g | 21 | 55 |
| c-vp16-78aa-P1 | atcgggtacc acggcccccc cgaccgatgt c | 31 | 56 |
| c-hER-XbaI-P1 | caggtccacc ttcttagaatg tg | 22 | 57 |
| c-hER-KpnI-P2 | cggggtaccg actgtggcag ggaaaccctc | 30 | 58 |
| N-79-F1 | cacggaccat ggcggccccc ccgac | 25 | 59 |
| N-79-R1 | ataagaatgc ggccgcggcg ttgaactc | 28 | 60 |

ER3M Chimeras with VP16

To fuse the VP16 transactivation domain to the N-terminal of ER3M, primers N-vp16-128aa-p1 and N-vp16-XbaI-P2 (SEQ ID NOS:49–50), and N-vp16-78aa-P1 N-vp16XbaI-P2 (SEQ ID NOS:51 and 50) were used to amplify by PCR VP16 transactivation domains containing either 129 amino acids or 79 amino acids. The two DNA products were digested with KpnI and XbaI and then purified from agarose gel. The primers N-hER-NheI-P1 and N-hER-NotI-P2 (SEQ ID NOS:52–53) were used to amplify the N-terminal fragment of ER. To create N-129 (including the stop codon), this ER N-terminal DNA fragment was digested with NheI and NotI and then cloned together with the DNA fragments containing 129 amino acids of VP16 into the 6.2 kb vector generated from CMV-hERα by digestion with KpnI and NotI. Using the same strategy the DNA fragment containing 79 amino acids of VP16, N-79 was constructed.

To fuse the VP16 transactivation domain to the C-terminus of ER3M, primers c-vp16-128aa-P1, c-vp16-P2 and c-vp16-78aa-P1, c-vp16-P2 (SEQ ID NOS:54–56) were used to amplify either the 129 or 79 amino acid transactivation domain. These fragments were digested with KpnI and BamHI and then purified from agarose gels. Primers c-hER-XbaI-P1 and c-hER-KpnI-P2 (SEQ ID NOS:57–58) were used to amplify the C-terminal fragment of ER. To create C-129, this ER fragment was digested with XbaI and KpnI and then cloned together with the DNA fragment containing 129 amino acids of VP16 into 5.9 kb vector generated by digestion of CMV-hER with XbaI and BamHI. The same strategy was adopted to create C-79 using the DNA fragment containing 79 amino acids of VP16. Therefore, the expression of these chimeras is driven by the same CMV promoter as that of ER-3M. To express N-79 under control of the ATL8/PAL promoter, two PCR primers, N-79-F1 and N-79-F2 (SEQ ID NOS:59–60) were used to amplify the N-terminal coding region of N-79 (approximately 500 bp). The amplified PCR product was digested with NcoI and NotI. The pCMV-hER-3M plasmid was digested to completion with NotI and partially by XbaI to generate a 1.6 Kb hER-3M fragment. This fragment and the NcoI/NotI PCR fragment were then inserted together into the 4.3 kb vector, pGL3-ATL8/PAL-LUC, which was created by digesting ATL8/PAL-LUC completely with NcoI and partially with XbaI so that the luciferase gene was replaced by N-79.

The hERα expression plasmids (CMV-hERα and CMV-hERα/Δ41-64) have been described previously (Mattick et al., 1997; McInerney and katzenellenbogen, 1996). To create mutations in the ER DNA binding domain, AF2 domain and phosphorylation sites (S118 and S167), QuikChange mutagenesis (Stratagene, Calif.) was employed to introduce mutations into the full-length hERα using CMV-hERα as a template. The identity of the mutations was confirmed by sequencing. To avoid having to sequence the full length ERs for potential second site mutations that might occur during mutagenesis, fragments containing the DNA region to be mutated were excised by digestion with restriction enzymes and subcloned into either CMV-hERα or CMV-hERα-3M vector digested with the same restriction enzymes.

ER-containing Extract Preparation

CHO—S cells (Life-Technologies; Grand Island, N.Y.) were transfected using Lipofectamine 2000 (Life-Technologies). Transfection was performed according to the manufacturer's instructions, except cells were grown in 6-well plates coated with 1 ml of 0.1 mg/mL polylysine for 24 hours at 37° C. prior to transfection. One μg of CMV-hERα and 3 μg of pTZ18U carrier DNA were used for each well; DNA:Lipofectamine 2000 was 1:3. 17β-estradiol was added to a final concentration of 10 nM 1 hour before harvest. Whole cell extracts were prepared as described (Zhang et al., 1996) with a modified extraction buffer (50 m-M Tris-HCl, pH 7.5, 1.5 mM EDTA, 10 mM Na$_2$MoO$_4$, 0.5 M NaCl, 10% glycerol, 0.5 mM β-mercaptoethanol, 50 μg/ml leupeptin, 1 μg/ml pepstatin and 5 μg/ml aprotinin).

Gel Mobility Shift Assays

Gel mobility shift assays were performed essentially as described [Zhang, 1999 #38]. Each 20 μl reaction contained 50 mM KCl, 15 mM Tris-HCl (pH 7.9), 4 mM dithiothreitol, 0.2 mM EDTA, 3 μg of poly(dIdC) and 10% glycerol; bovine serum albumin (BSA) was added to each sample for a total of 10 μg of protein. Free probe and protein-DNA complexes were quantitated using a phosphor imager and ImageQuant 5.0 (Molecular Dynamics, Inc., Sunnyvale, Calif.). The sequence of one DNA strand of each of the three probes (SEQ ID NOS:61–63) used for the gel mobility shift assays are presented in Table 31. The ERE or PAL sequences are underlined.

TABLE 31

Probes for GEMSAs

| Probe | Sequence | SEQ ID NO |
|---|---|---|
| cERE | agcttctcta ttaggtcact | 61 |
| | gtgaccttca tctgaagct 39 | |
| native pS2 ERE | agcttctcta ttgggccact | 62 |
| (complement of SEQ ID NO:61) | gtgaccttca tctgaagct 39 | |
| pS2 PAL | agcttctcta ttgggccact | 63 |
| | gtggccctca tctgaagct 39 | |
| native pS2 PAL | agcttcagat gagggccaca | 64 |
| (complement of SEQ ID NO:63) | gtggcccaat agagaagct 39 | |

Cell Maintenance, Transfection, and Reporter Gene Assays

HepG2 human hepatoma cells were maintained in a humidified 5% CO$_2$ incubator at 37° C. in Dulbecco's Modified Eagle's Medium (DMEM; Sigma; St. Louis, Mo.) supplemented with 10 % charcoal-dextran-stripped fetal bovine serum (CD-FBS; Atlanta Biologicals, Inc; Atlanta, Ga.), 50,000 U/l of penicillin, and 50 mg/liter streptomycin (Life Technologies, Inc.). MCF-7 cells were routinely maintained in DMEM/Nutrient Mixture F-12 (DMEM/F12) supplemented with 10% heat-inactivated FBS, 50,000 U/l of penicillin, and 50 mg/l streptomycin. CHO-S cells were maintained in DMEM/F12 supplemented with 10% heat-inactivated FBS (CD-FBS when ERs were being expressed) or 10% CD-new born calf serum (CD-NBCS, when reporter activity by different ligands were measured), 29.2 mg/l L-glutamine (Sigma), and 50,000 U/l of penicillin and 50 mg/l streptomycin.

Transient transfections in HepG2 cells was accomplished using calcium phosphate co-precipitation (Ausubel et al., 1987). Briefly, cells were plated in 12-well microplates at a density of 1×10$^5$ cells/well. The next day, the medium was replaced, and 2–6 hours later, precipitated calcium phosphate:DNA co-crystals were added. After 12–16 hours, the cells were shocked for 3 minutes with 20% glycerol in Tris-buffered saline, pH 7.4. Fresh medium and (if any) hormones were added. For MCF-7 and 231 cells, transient transfection was carried out using the Tfx™-20 reagent (Promega; Madison, Wis.) according to the manufacturer's direction with minor changes. Briefly, 1×10$^5$ cells were plated in each well of 12-well microplates one day before transfection. A 1:3 ratio of DNA to lipid was used. The DMEM/F12 medium without serum was used as carrier for the DNA-lipid mixture. After 1 hour incubation with the DNA-lipid-DMEM/F12 at 37° C., the cells were transferred to fresh DMEM/F12 supplemented with 10% CD-FBS, 50,000 U/I of penicillin, 50 mg/l streptomycin and hormones. Transfection on CHO—S cells was described as above for the preparation of ERs extraction except the medium contained 10% CD-NBCS. The cells subjected to either transfection method were harvested 48 hours post-transfection. Reporter assays were performed by lysing the cells in situ with 250 μl of passive lysis buffer (Promega). Activity was determined using the dual luciferase assay protocol according to the manufacturer's directions (Promega) on a Monolight 2010 luminometer (Analytical Luminescence, San Diego, Calif.)

Example 2

Expression of hERα Mutants in CHO-S Cells

The tested mutations were derived from an analysis of common mutations in a large pool of genetically selected steroid receptor DBD mutants previously developed and tested (Chusacultanachai et al., 1999). For each mutant, the amino acid sequence of the mutated region of the DBD is shown in 17, 21, 23, 25 and 27. The expression levels of wild-type ERα and ER mutants from extracts of transiently transfected CHO—S cells were determined by Western blotting (Ausubel et al., 1987). Wild-type and mutant ERs were expressed at similar levels. Extracts were normalized for ER quantities (FIG. 1A(i)). Crude extracts rather than purified ERs were used so that any cell proteins that might modulate binding of ER to different EREs were present.

Example 3

Binding of ER Dimers to Imperfect EREs Involves Tight Binding to a Consensus Half Site and Weak Binding to Specific Imperfect Half Sites Electrophoretic mobility shift assays (EMSAs) were used to evaluate the ability of wild-type ER and ER mutants to bind the cERE and pS2 ERE (FIG. 1A(ii);using cERE (SEQ NO:61) and pS2 ERE probe (SEQ NO:62). Because ER mutants 2.1, 7.2, 15.3, 50.1 and 57.1 showed little or no binding to these DNA probes, they were not further analyzed.

To compare binding of wild type hERα and the ER mutants to the EREs, protein titrations were performed. Increasing amounts of extracts containing equivalent levels of wild-type ER or ER mutants were incubated with the cERE. The ER:ERE complexes were then analyzed by EMSA. Wild-type ER exhibited better binding to the cERE than any of the ER mutants (FIG. 1B). The mutants required 1.5–2.4-fold more extract to bind 50% of the cERE probe than wild-type ER. Although wild-type-ER exhibited a higher affinity for the cERE half site in the cERE than any of the mutants, it bound less well to the imperfect ERE of pS2 than all but one of the mutants (FIG. 1C). Most of the ER mutants showed similar binding to the pS2 ERE which, as expected, was somewhat weaker than their binding to the cERE. Wild-type hER and mutant 6.2 exhibited a dramatic decrease in binding to the pS2 ERE probe. Even at the highest level of extract (8 μg), wild-type ER shifted only ~15% of the pS2 probe. Wild-type ER was approximately 3–4-fold less effective in binding to the pS2 ERE than the five ER mutants that exhibit strong binding.

Since wild-type ER was more effective in binding to the cERE than the ER mutants, and less effective in binding to the pS2 ERE than five of the six ER mutants, it seemed likely that wild-type ERα interacts strongly with the consensus half site in the pS2 ERE but only weakly with the imperfect half site. To test this idea, synthetic probe (SEQ NO:63) comprising a perfect palindrome with both half sites representing the imperfect ERE half site in the pS2 gene was prepared (FIG. 1A(ii), pS2 PAL). While all five of the ER mutants that exhibited significant binding to the native pS2 ERE retained the ability to bind to pS2 PAL, binding of wild-type ER to pS2 PAL was negligible and less than 100-fold weaker than cERE binding. The five ER mutants showed greater than 30-fold higher affinity for pS2 PAL than wild-type ER (FIG. 1D).

Wild-type ER activates transcription from the native pS2 gene in vivo (Nunez et al., 1989) and some binding to the pS2 ERE in vitro, but fails to significantly bind pS2 PAL. It therefore seemed possible that binding of wild-type ER to the pS2 ERE is based on strong binding of one monomer of the ER dimer to the cERE half site (aGGTCA; SEQ ID NO: 65) and weak non-specific interaction of the other ER monomer with the sequence at the other half site. To test this possibility, binding of wild-type and the ER mutants to a putative ERE in the Bcl2 gene was examined. Like pS2, Bcl2 contains a cERE half site, but also contains a second, different half site that deviates from the consensus sequence by one nucleotide. Even the barely detectable binding seen for the interaction of wild-type ER with pS2 ERE was absent with the Bcl2 sequence, and none of the ER mutants showed detectable binding to this sequence. These data indicate that binding of ER to the imperfect pS2 ERE is based on strong interaction of one monomer of the ER dimer with the consensus half site and weak, but sequence specific, interaction of the other monomer with the imperfect half site.

FIG. 1 (Legend) A. Panel (i), Western blots of normalized whole cell extracts of wild type hERα and mutants from transfected CHO-S cells. Lane 1–13: mutants 4, 2, 57.1, 50.1, 15.3, wild type ER, 7.2, 6.2, 4.3, 3.1, 2.1, wild type, and 3M, respectively. Panel (ii), The three ERE sequences used in these studies. The nucleotides that differ from those in the consensus ERE (cERE) are underlined. Nucleotides in lower case lettering are less well conserved or not conserved in EREs. Gel mobility shift assays, panels B, C, and D: For each assay the top section shows the gel shifted band and the lower section contains a graphical representation of the per cent of the labeled probe in the shifted band. The data were calculated by PhosphorImager analysis. (B) The labeled cERE probe was incubated with 0.5, 1.0, 2.0 and 4.0 μg of whole cell extracts of wild type hERα, or extracts containing the mutant ERs normalized to contain the same amount of ER as the wild-type ER extract at each point. (C) Gel shift assays using the labeled pS2 ERE probes and increasing amounts (1.0, 2.0, 4.0 and 8.0 μg) of the whole cell extracts containing wild-type ER and each of the ER mutants. (D) Gel shift assays using the labeled pS2 palindrome ERE probe. The ER extract contained 2.0, 4.0 and 8.0 μg of whole cell extract (panel (i)), and 15 μg (panel (ii)). Lanes 1–7 (panel (ii)) represent wild type hERα, and mutants 3M, 3.1, 4.3, 6.2, 2 and 4, respectively. D (iii) contains a graph of the percentage of the labeled pS2 PAL probe shifted calculated by PhosphorImager analysis of the data in D(i) and D(ii).

Example 4

When the ER Ligand is a Potent Estrogen, In Vivo Trans-activation Correlates with In Vitro ERE Binding To analyze the role of affinity for the DNA sequence in ER-mediated trans-activation and to determine if in vitro binding data from EMSAs (Example 3) would relate to intracellular transactivation, the activity of wild-type hERβ and ER mutants was analyzed in transient transfections in HepG2 cells using reporter genes containing each of the three EREs. Because binding to the pS2 PAL sequence is too low to obtain reliable data using reporter genes containing one copy of an ERE sequence, reporter genes containing two copies of each ERE were constructed. Preliminary experiments indicated that 2.5 ng of ERs expression plasmid (per well) resulted in maximal transactivation, and 0.75 ng of plasmid resulted in robust, but sub-maximal, transactivation. In HepG2 cells in the absence of transfected expression plasmid encoding wild-type or an ER mutant, no moxestrol (MOX)-dependent transcription from any of the EREs was observed (FIGS. 2A–C), indicated that there is no endogenous ER in the cells. In transfections using the reporter containing the cERE (ATL2/cERE-LUC), wild-type hERα elicited MOX-dependent increases in luciferase activity of 32- and 41-fold with 0.75 and 2.5 ng of expression plasmids, respectively (FIG. 2A). Consistent with their weaker binding to the cERE than wild-type ER (FIG. 1B), all of the ER mutants were less effective in activating transcription from the cERE than the wild-type (FIG. 2A). Wild-type ER exhibited weaker binding to native pS2 ERE than five of the six mutants. Three of these five ER mutants (3M, 4.3, 4) activated transcription from the ERE more effectively than wild-type ER, and the other two mutants (3.1, 6.2, 2) were less effective (FIG. 2B). Wild-type and mutant 6.2 ERs exhibited negligible binding to the pS2 PAL ERE in EMSAs (FIG. 1D) and showed little or no ability to activate transcription of the pS2 PAL reporter in transient transfections (FIG. 2C). At the lower DNA levels used in transfection (0.75 ng), mutant 3M, which showed modestly lower binding to the pS2 PAL than the other four mutants, was also less effective in activating transcription (FIG. 2C). The five ER mutants that bound pS2 PAL activated transcription from the pS2 PAL reporter 3.5- to 9-fold. These data show that in vitro transactivation was roughly proportional to the in vitro ability of the various ERs to bind an ERE. Furthermore, when an ER exhibited negligible in vitro ERE binding, it also failed to transactivate transcription in vitro.

Figure 2:
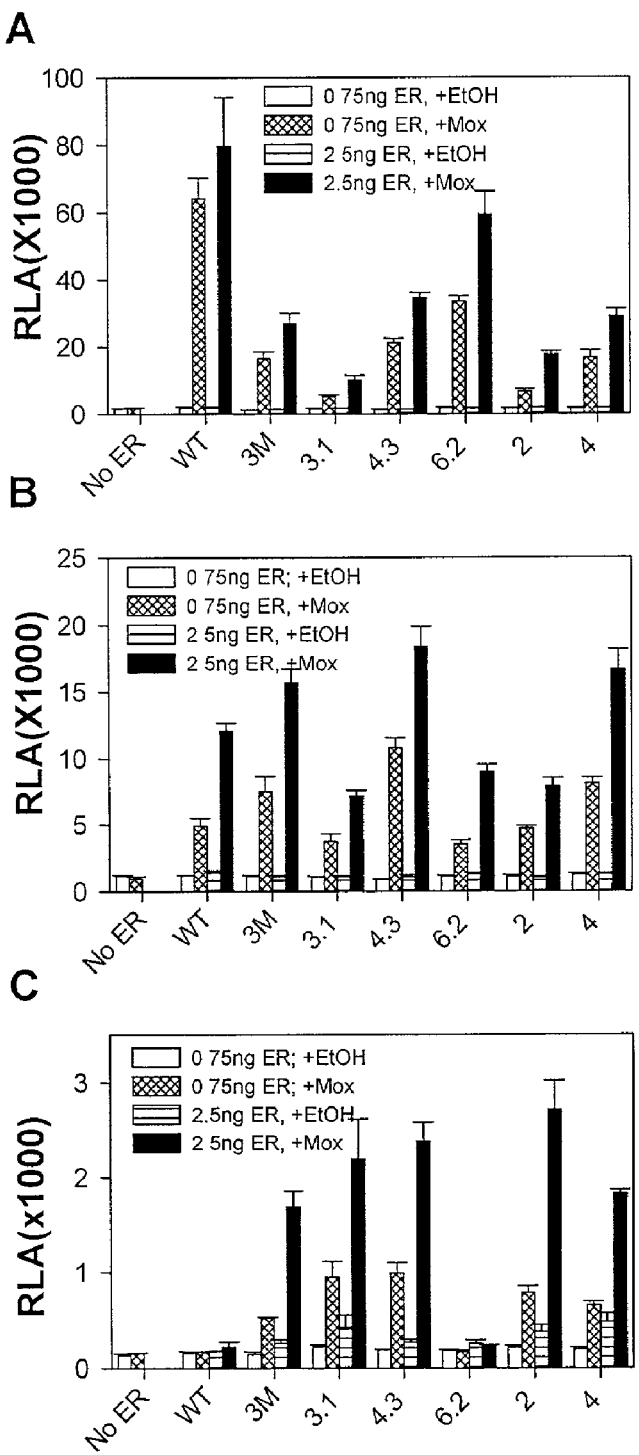
FIGS. 2A–2C are graphs that illustrate the correlation between the affinity of various ERs for EREs in vitro (FIG. 1) and their in vivo transactivation on EREs operably-linked to a reporter gene (ATL2/cERE-LUC (FIG. 2A); ATL2/pS2 ERE-LUC (FIG. 2B) and ATL2/PAL-LUC (FIG. 2C) when bound with potent estrogen ligand, MOX.

Transient transfections of HepG2 cells were carried out and luciferase activity determined. Two hundred ng of each reporter and 5 ng of *Renilla* luciferase expression plasmid, as an internal standard, were co-transfected with either 0.75 ng or 2.5 ng of the expression plasmid encoding wild type hERα or an ER mutant. No ER contained a reporter, but not the expression plasmid for ER or a mutant ER. In FIG. 2, empty bars and bars with horizontal lines represent transactivation in the presence of 0.75 or 2.5 ng, respectively, of expression plasmid and ethanol vehicle, but no hormone. The cross-hatched and black bars represent transactivation in the presence of 10 nM moxestrol (+MOX) using 0.75 or 2.5 ng of transfected expression plasmid, respectively. Panels A–C represent transfections using the cERE-based reporter (ATL2/cERE-LUC), the pS2 ERE-based reporter (ATL2/pS2 ERE-LUC) and the pS2 PAL-based reporter (ATL2/PAL-LUC), respectively. The data represent the mean±S.E. of three independent transfections.

Example 5

Figure 3:
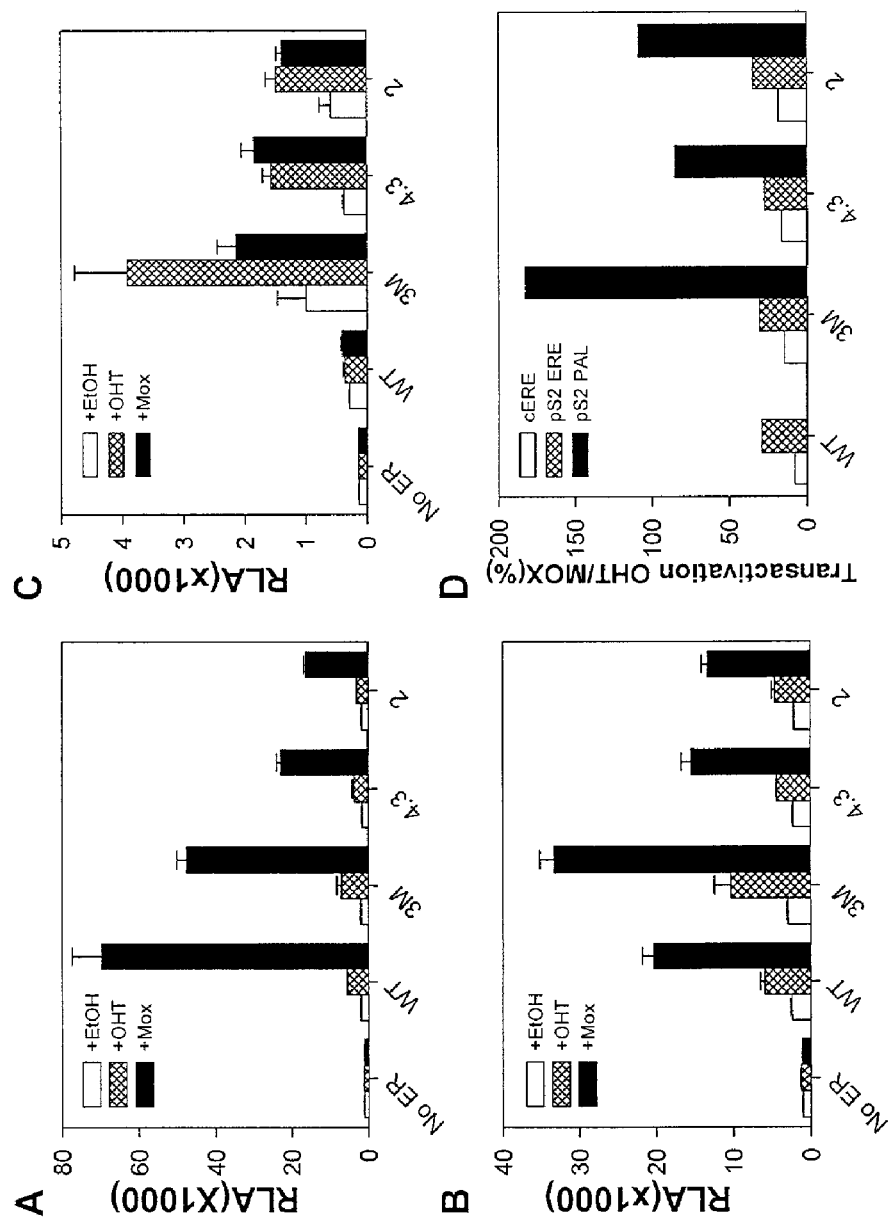
FIGS. 3A–3D are graphs that show transactivation of a reporter gene (luciferase) operably-linked to the cERE (FIG. 3A, ATL2/cERE-LUC), pS2 ERE (FIG. 3B, ATL2/pS2 ERE-LUC) and pS2 PAL (FIG. 3C, ATL2/PAL-LUC) in the absence or presence of OHT or MOX.

4-hydroxytamoxifen (OHT) is a Potent Transactivator when ER Mutants are Bound to the pS2 PAL ERE Strong binding of wild-type ER to cERE by co-expression of HMG-1 enhances the agonist activity of OHT relative to 17β-estradiol and moxestrol (Zhang et al., 1999). This observation suggested that ER mutants with a reduced ability to bind cERE might show a reduced level of OHT agonism and therefore a decreased ratio of OHT:MOX transactivation. The ability of the ER mutants, which all bind less well to cERE than wild-type ER, to activate transcription in the presence of OHT or moxestrol was examined. Consistent with earlier studies that tamoxifen exhibits weak agonist activity in HepG2 cells (Barkhem et al., 1997), OHT-wild type hERα exhibited weak agonist activity when bound to the cERE (FIG. 3). The ratio of OHT agonism to moxestrol agonism was slightly higher for most of the mutants than that seen with wild-type hERα (FIG. 3A). These data indicate that reduced cERE affinity does not significantly reduce the ability of OHT to act as a weak agonist.

These data also suggested that there is a correlation between the affinity of an ER for the ERE and its ability to activate transcription in the presence of either a potent estrogen (MOX) or a weak ER agonist (OHT). To evaluate the possibility that the sequence of the ERE influences the transactivation potential of a weak estrogen, transient transactivations using pS2 ERE and the pS2 PAL elements were performed. When the native pS2 ERE (ATL2/pS2 ERE-LUC) was used, both wild type ER and the ER mutants exhibited moderate transactivation in response to OHT, about 30% of that seen with MOX (FIG. 3B). In contrast, OHT acted as a full agonist with transactivation potential equal to, or greater than, that exhibited by MOX when pS2 PAL (ATL2/PAL-LUC) supplied the ERE. Transactivation by OHT exceeded that seen with MOX when ER3M was used and was equal to that seen with MOX with ER 4.3 and 2 (FIG. 3C). Transactivation levels seen with OHT and MOX using wild-type ER were undetectable. These data are summarized in FIG. 3D, which compares the ratio of transactivation by OHT to that seen with MOX for each of the ERs and EREs. The imperfect pS2 ERE moderately increased transactivation by OHT relative to that seen with the cERE; creating a new synthetic ERE containing this imperfect half site in a palindrome sequence dramatically increased the transactivation potential of OHT.

In FIG. 3, 200 ng of each reporter and 5 ng of *Renilla* luciferase expression plasmid as an internal standard were co-transfected into HepG2 cells with either no ER or with 2.5 ng of plasmid expressing wild type hERα, or one of the ER mutants. Controls lacking transfected ER showed that transactivation by OHT and by MOX requires an estrogen receptor. In panels A, B, and C, transactivation was determined in the absence of ligand (empty bars), or after addition of 10 nM OHT (cross-hatched bars) or 10 nM MOX (filled bars). Panels A–C present data from transfections using a reporter containing the cERE, native pS2 ERE and pS2 PAL reporter genes, respectively. The data represent the mean±S.E. of three independent transfections. Panel D contains a graphical representation of the ratio of OHT/MOX transactivation for each of the reporter genes containing different EREs and ERs. Wild type ER did not show a quantifiable level of transactivation with two copies of pS2 PAL.

Example 6

Mutations in the ER DBD are Not Essential; the DNA Sequence of pS2 PAL is Sufficient to Convert OHT-Wild-Type hERα into a Potent Agonist Although OHT was at least as effective as MOX in transactivation from ATL2/PAL-LUC, consistent with the relatively weak binding of the mutants to the pS2 PAL ERE, the overall level of transactivation induced with OHT or with MOX was modest (FIG. 3C). Studies have demonstrated synergistic enhancement of transcription in reporter genes containing multiple EREs (Martinez and Wahli, 1989; Mattick et al., 1997; Ponglikitmongkol et al., 1990). To determine if OHT elicits a more robust activation from pS2 PAL with multiple EREs, reporter genes containing four copies of the cERE (ATL4/cERE-LUC) and pS2 PAL (ATL4/PAL-LUC) were constructed and evaluated for their transactivation using wild type hERα and ERs 3M and 4.3. As seen with two copies of cERE constructs, (FIG. 3A), OHT was a weak agonist in transfected HepG2 cells, exhibiting 20–25% the activity seen with MOX on the ATL4/cERE-LUC reporter (FIG. 4A). However, when four copies of pS2 PAL were present, OHT was a potent agonist exhibiting the same level of transactivation as MOX (FIG. 4B). Both the overall transactivation level and fold induction achieved with OHT or with MOX were dramatically increased when the reporter gene contained four copies of pS2 PAL. With ER mutants 3M and 4.3, OHT elicited greater than 80-fold induction in cells transfected with ATL4/PAL-LUC.

To determine whether the pS2 PAL DNA sequence alone is sufficient to elicit potent OHT agonism in the absence of ER DBD mutations, reporter genes containing eight copies of pS2 PAL or cERE were constructed and analyzed for transactivation by the wild-type ER. Despite its very weak binding to a single copy of pS2 PAL, wild-type ER showed limited, but readily quantifiable, activity in transactivation from ATL8/PAL-LUC. Upon addition of OHT, wild-type ER elicited a 52-fold induction of luciferase activity from ATL8/PAL. Transactivation of ATL8/PAL-LUC by wild-type ER was higher with OHT than with MOX (FIG. 4C). With the ATL8/cERE-LUC, OHT is still a weaker agonist than moxestrol. These data demonstrate that the pS2 PAL DNA sequence alone is sufficient to convert OHT bound to wild-type ER into a potent agonist in HepG2 cells. The ER DBD mutations enhance the binding of ER to pS2 PAL and, consequently, strongly increase the overall level of transactivation from pS2 PAL. However, the DNA sequence of pS2 PAL, not the mutations in the DBD, is responsible for the potent agonist activity of OHT.

Figure 4:
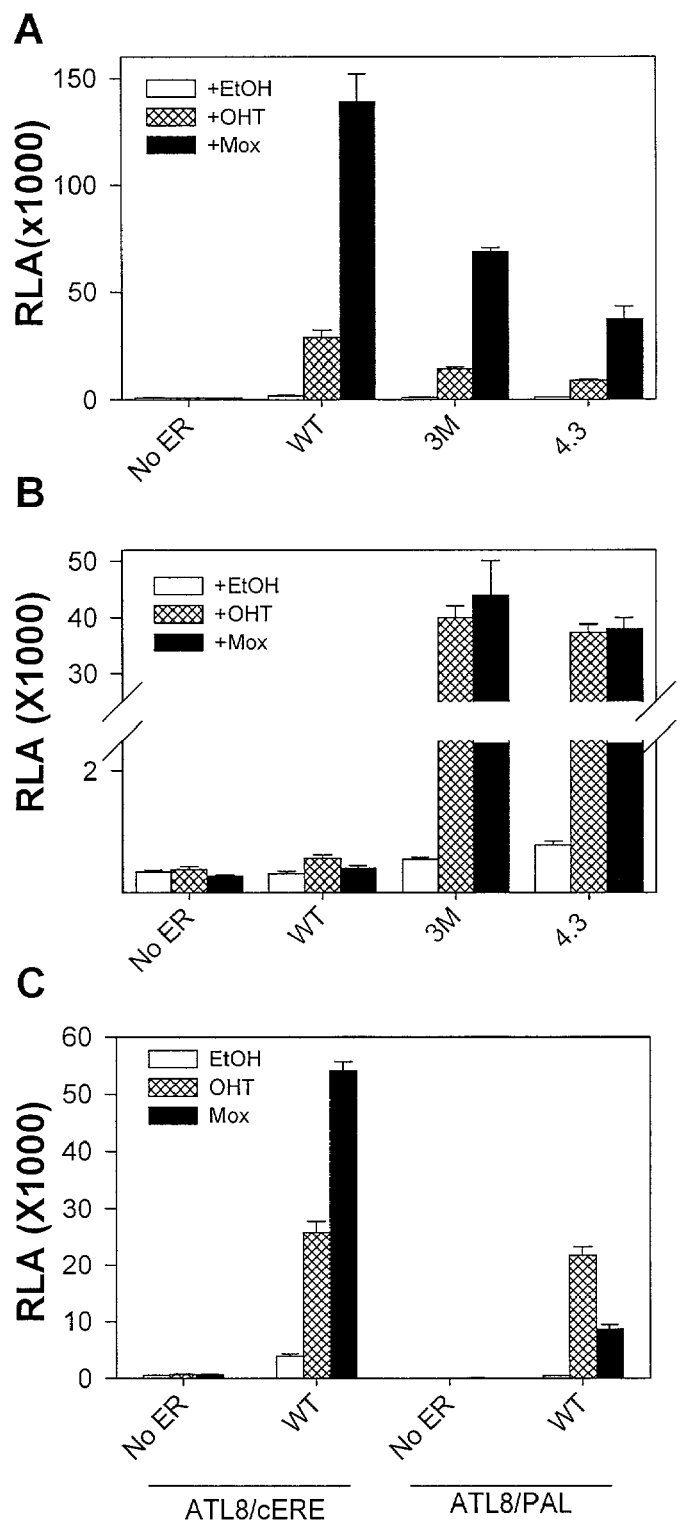
FIGS. 4A–4C are graphs that show that mutations in the ER DBD are not essential, but the pS2 PAL sequence is important in converting OHT into a potent agonist using wild-type ER.

In FIG. 4, 100 ng of ATL4/cERE -LUC (panel A), ATL4/PAL-LUC (panel B) reporter genes and 5 ng of *Renilla* luciferase expression plasmid as an internal standard were co-transfected with either no ER or 2.5 ng of the expression plasmid for wild type hERα, 3M or 4.3 mutant. In panel C, 100 ng of the indicated reporter genes with either no ER expression plasmid or with 5 ng of expression plasmid for wild type ER were co-transfected. Empty bars represent the data for samples in the absence of ligand, cross-hatched bars and filled bars for data obtained after addition of 10 nM OHT or MOX to the culture medium. The data represent the mean±S.E. of three independent transfections.

Example 7

Figure 5:
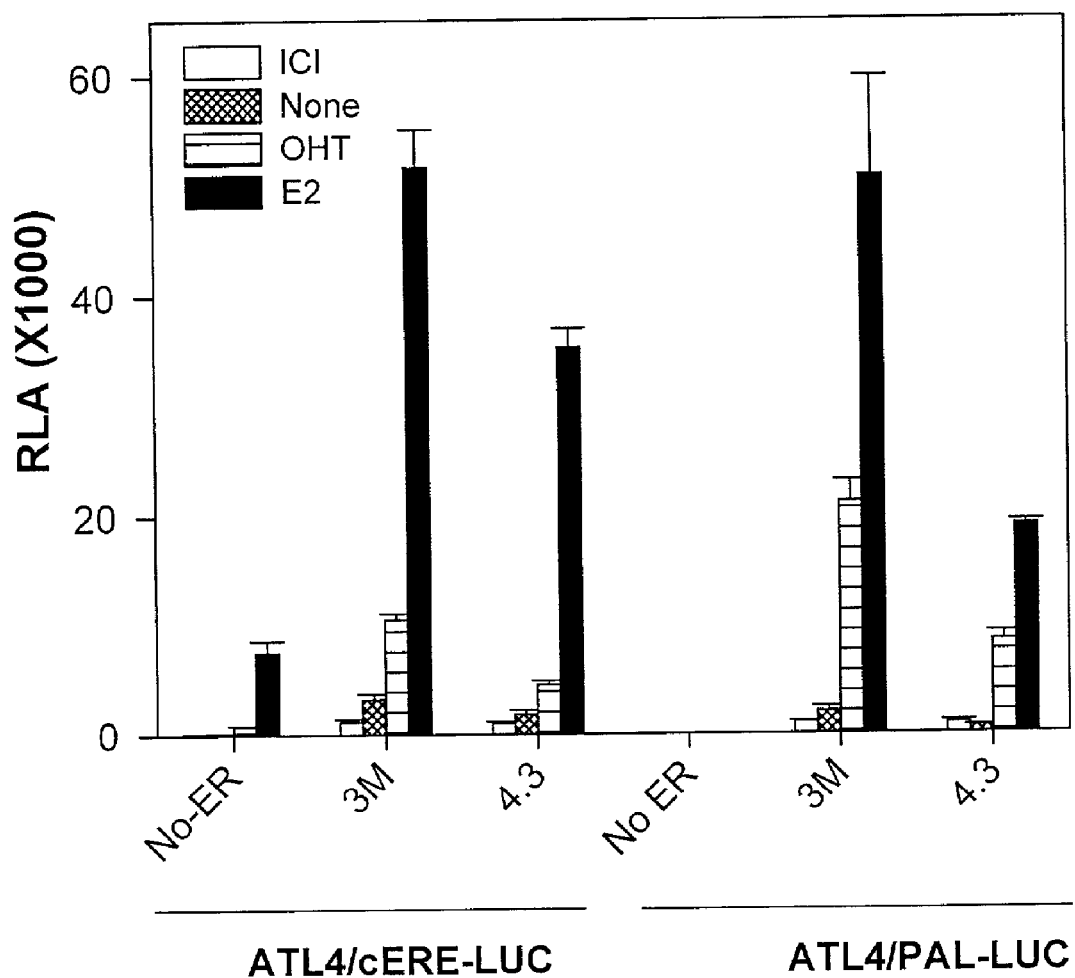
FIG. 5 shows a graph that demonstrates that pS2 PAL enhances OHT-mediated transactivation in cell types other than HepG2, such as MCF-7.

The pS2 PAL Sequence Enhances Transactivation by 4-Hydroxytamoxifen in Other Cell Lines Several studies have demonstrated that OHT exhibits some agonist activity in HepG2 cells (Barkhem et al., 1997). To test whether OHT-ER bound to pS2 PAL was effective in transactivation in cell lines other than HepG2 cells, transient transfections were performed in MCF-7 cells with constructs containing reporters operably-linked to the cERE and to pS2 PAL, and transactivation was measured using MOX and OHT. When MCF-7 cells were transfected with ATL4/cERE-LUC, OHT-mediated transactivation exhibited 20% and 13% of that observed with estradiol ($E_2$) when ER mutants 3M and 4.3 were used (FIG. 5). Using ATL4/PAL-LUC as a reporter gene with ER mutants 3M and 4.3, transactivation by OHT was 42% and 45% of that seen with $E_2$ (FIG. 5).

The compound ICI 182,780 (Tocris; Ballwin, Mo.) acts as an antagonist and is thought to block the nuclear translocation of ERα (Htan et al., 1999). However, ICI 182,780 functions as an agonist when the ER is tethered to promoters through API sites (Webb et al., 1995). ICI functioned as an antagonist on reporters containing either the cERE or pS2 PAL (FIG. 5). These data indicate that although binding of wild-type hERα and the ER mutants to pS2 PAL is weak, the ERs activate transcription by direct binding to the pS2 PAL ERE.

FIG. 5 shows the results of reporter genes when co-transfected with either no ER expression plasmid (No ER) or 5 ng of expression plasmids coding for either of the ER mutants, 3M and 4.3; 5 ng of *Renilla* luciferase expression plasmid was used as an internal standard. Reporter gene activity in the presence of ethanol vehicle (cross-hatched bars) or 10 μM of $E_2$ (filled bars), OHT (striped bars), or ICI 182,780 (open bars) was determined. The data represent the mean±S.E. of three independent transfections.

Example 8

Both the AF1 and AF2 Functions of hERα are Required for Full Transactivation by 4-Hydroxytamoxifen AF1 plays a key role in transactivation by OHT (McInerney and Katzenellenbogen, 1996). To dissociate effects due to OHT transactivation from general transactivation mediated by the AF1 region, a deletion mutant, ERΔ41–64, was used. This segment of the A/B domain is important for OHT transactivation, but not for $E_2$ transactivation (McInerney and Katzenellenbogen, 1996). In addition to using ERΔ41–64 as an AF1 mutant, the well-characterized hERα mutants D351Y (Levenson et al., 1997; Levenson and Jordan, 1998; Webb et al., 2000), M543AL544A (ML) and L540AL541A (LL) (Danielian et al., 1992; Shiau et al., 1998) were used as AF2 mutants. All these mutants were put into ER3M so that they could be compared with ER3M on ATL4 reporters. To determine whether transactivation of pS2 PAL by OHT-ER requires both the AF1 and AF2 functions, ER3M, the AF1 deletion and the AF2 disruption mutants were analyzed by transfection with the ATL4/cERE-LUC and ATL4/PAL-LUC reporters in HepG2 cells. Deletion of amino acids 41–64 caused a larger reduction in OHT-mediated transactivation from both reporters than in MOX-mediated transcription, indicating that OHT-mediated transactivation on both cERE and PAL is largely through the AF-1 function. The mutations in the AF-2 region also affected the OHT-mediated transactivation on ATL4/PAL-LUC, suggesting the involvement of the AF2 function on the PAL. These data indicate that the segment of the A/B domain previously identified as important for the weak agonist activity seen when OHT-ER is bound to the cERE is also important for the strong agonist activity seen when OHT-ER is bound to pS2 PAL. While these data demonstrated that a segment of the AF1 region was critical for transactivation, they did not address whether AF1 is sufficient for transactivation by OHT-ER.

Figure 6:
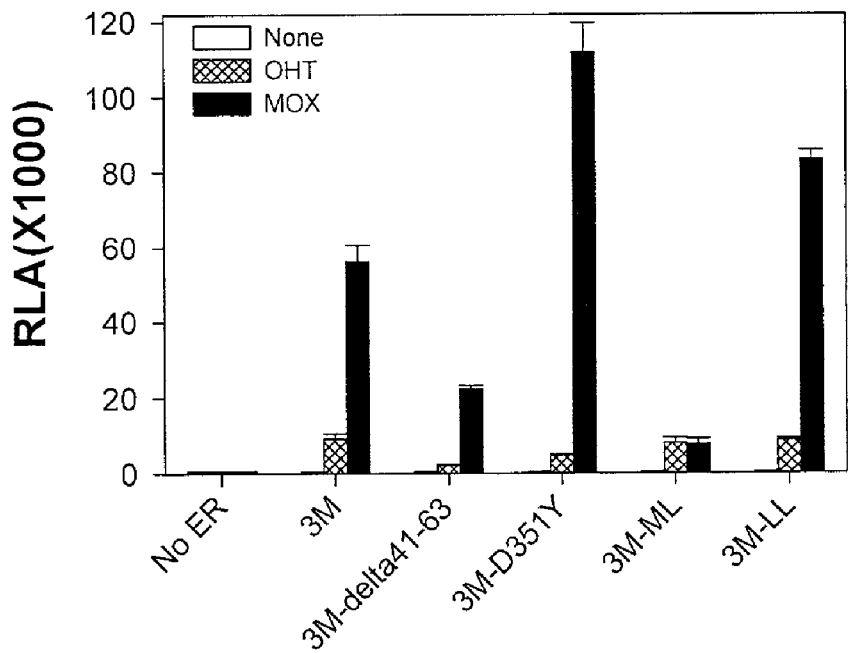
FIGS. 6A–6B show graphs that show that both AF1 and AF2 functions of HERα are 20 critical for full OHT-transactivation. AF2 mutants were engineered into ER3M, and their ability to transactivate from the cERE (FIG. 6A, ATL4/cERE-LUC) and pS2 PAL (FIG. 6B, ATL4/PAL-LUC) operably-linked to luciferase was determined.
Figure 6:
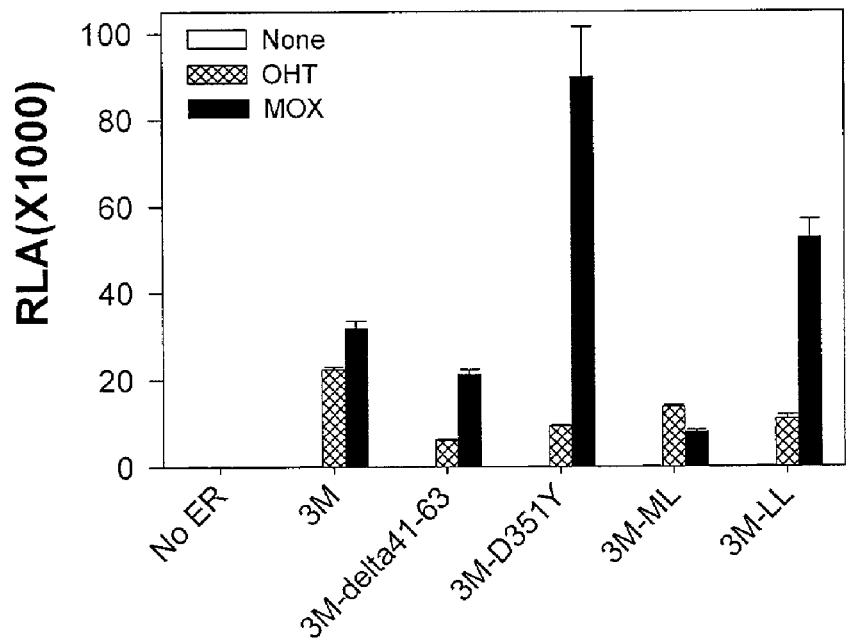

In FIG. 6, 100 ng of ATL4/cERE-LUC (panel A) and ATL4/PAL-LUC (panel B) and 5 ng of *Renilla* luciferase expression plasmid as an internal standard were co-transfected into HepG2 cells with either no ER or with 2.5 ng of ER3M or the AF1 or AF2 mutants. Transactivation in the presence of ethanol vehicle (open bars), 10 nM OHT (cross-hatched bars or 10 nM MOX (Filled bars) was determined. The data represent the mean±S.E. of three independent transfections.

Example 9

Phosphorylation of ER Amino Acid S118 is Involved in OHT Transactivation

Phosphorylation of ER amino acid S118 (Ali et al., 1993; Kato et al., 1995) is thought to enhance estradial-mediated transactivation. Recently, Si167 and other serine residues were shown to be phosphorylated by the Akt signal transduction pathway (Martinet al., 2000). S118 and S167 were mutated to either alanine (S118A, S167A) to prevent the phosphorylation of these sites, or glutamic acid (S167E, S167E) to mimic the phosphorylation of these sites. These mutations were put into ER3M so that they could be compared with ER3M on the ATL4/PAL-LUC reporter. The data in FIG. 7 show that S118A reduces transactivation, and that S118E can restore reduced transactivation, while S167 plays no role.

Figure 7:
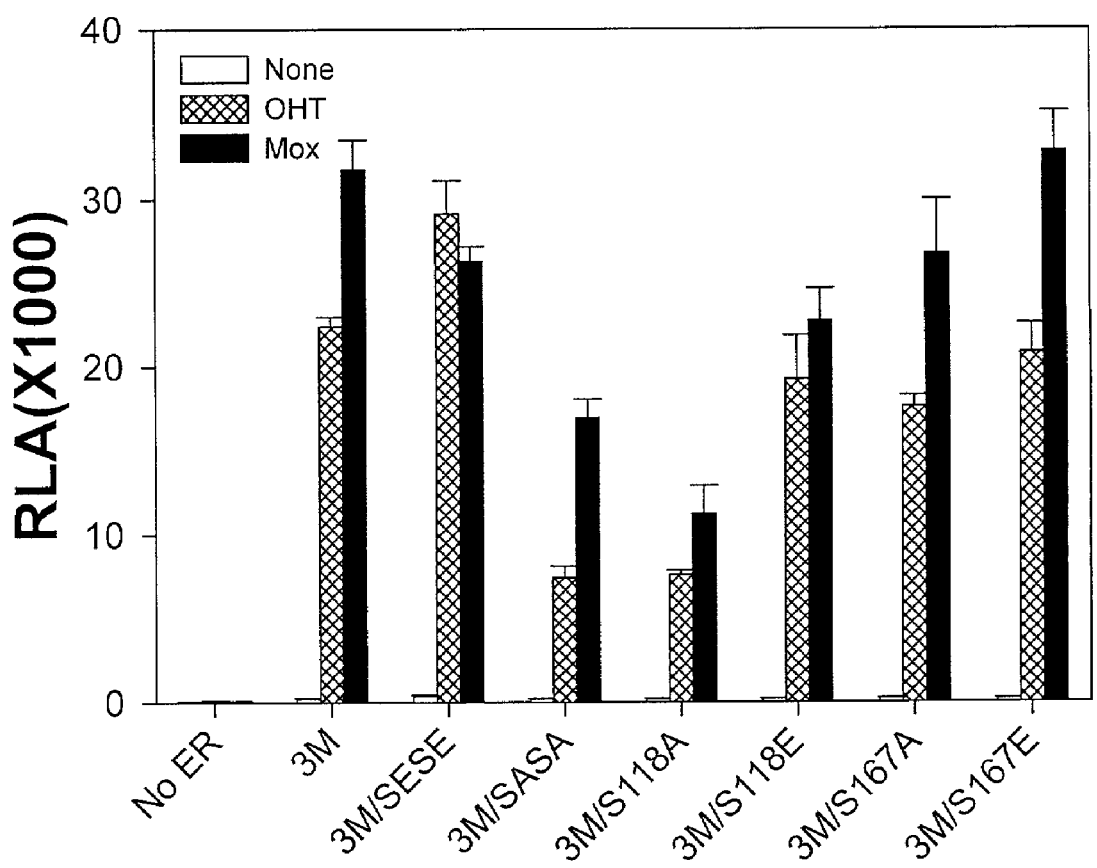
FIG. 7 shows a graph the illustrates that phosphrylation of Serine 118 is necessary for enhanced transactivation by ER3M bound with OHT on the pS2 PAL reporter construct.

In FIG. 7, 100 ng of ATL4/PAL-LUC and 5 ng of *Renilla* luciferase expression plasmid as an internal standard were co-transfected into HepG2 cells with either no ER expression plasmid (No ER) or with 2.5 ng of expression plasmid for ER mutants. Transactivation in the presence of ethanol vehicle (open bars), 10 nM OHT (cross-hatched bars) or 10 nM MOX (filled bars) were determined. The data represent the mean±S.E. of three independent transfections.

Example 10

OHT Transactivation on ATL8/PAL-LUC

Figure 8:
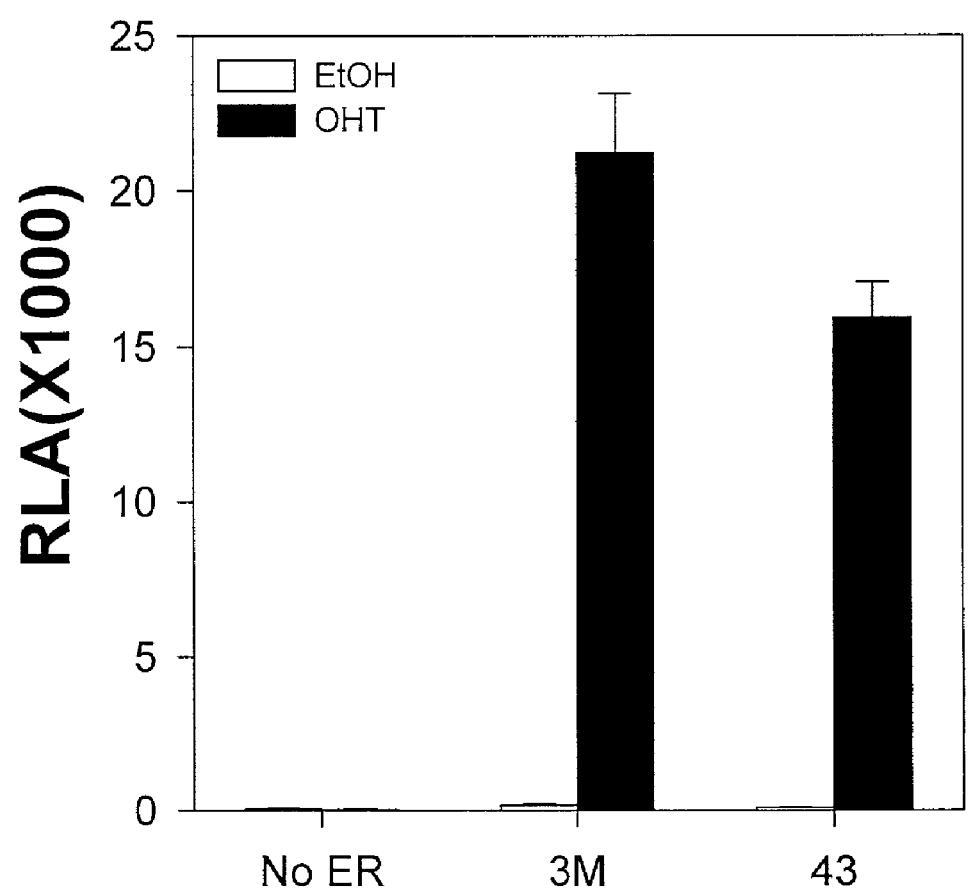
FIG. 8 shows a graph that illustrates that the fold induction on the construct ATL8/PAL-LUC by OHT is higher than that seen with the ATL4/PAL-LUC construct (FIG. 4).

To achieve higher fold induction by OHT, ATL8/PAL-LUC was constructed and tested in HepG2 cells. FIG. 8 shows transactivation by OHT of this reporter with ER mutants 3M and 4.3. In the absence of transfected ER expression plasmid (No ER), there was no OHT induction, indicating that reporter gene expression was ER-dependent. With ER mutants 3M and 4.3, OHT increased reporter gene expression by 117- and 172-fold, respectively. These increased inductions are higher than those seen with ATL4/PAL-LUC and these mutants (FIG. 4).

In FIG. 8, 50 ng of ATL8/PAL-LUC reporter gene and 5 ng of *Renilla* luciferase expression plasmid as an internal standard were co-transfected either with no ER expression plasmid (No ER) or with 2.5 ng of ER mutants 3M or 4.3. Transactivation was determined in the presence of ethanol vehicle (open bars), and 10 nM OHT (filled bars). The data represent the mean±S.E. of three independent transfections.

Example 11

Figure 9:
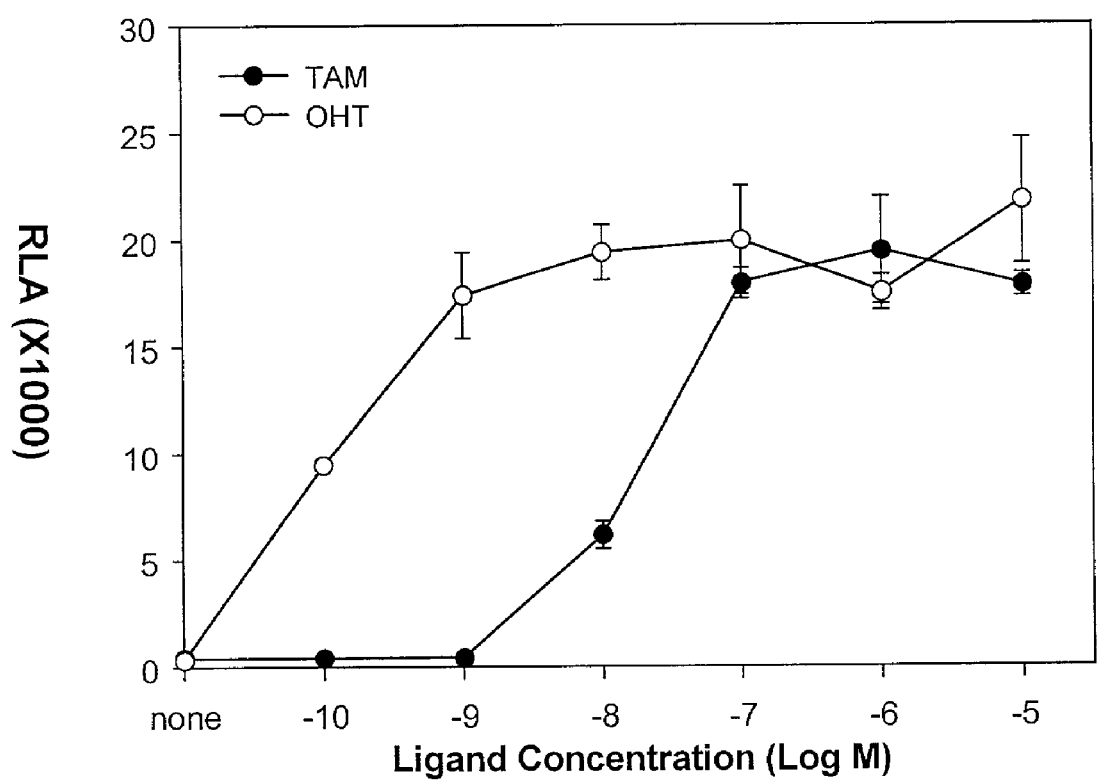
FIG. 9 shows a graph that when ER3M is used, tamoxifen at high concentrations, like its active metabolite, OHT, is a potent agonist on the ATL8/PAL-LUC reporter.

At High Concentrations, Tamoxifen and OHT Exhibit Similar Activation of pS2 PAL ERE Tamoxifen is used routinely to treat breast cancer, but at higher doses than the OHT concentrations used in these studies (Peyrade et al., 1996). To determine if tamoxifen and OHT have similar abilities to activate transcription from the synthetic pS2 PAL ERE, transient transfections were performed, and a range of OHT and tamoxifen concentrations were tested for their ability to transactivate luciferase expression. Consistent with previous studies using the cERE (Zhang et al., 1999), OHT elicited half maximal transactivation at ~0.1 nM (FIG. 9). Tamoxifen elicited half maximal activation at ~30 nM. The maximal levels of transactivation seen with tamoxifen and with OHT were similar. These data suggest that the structural differences between tamoxifen and OHT contribute to their different abilities to bind to the ER, but do not affect their ability to transactivate from the pS2 PAL ERE.

In FIG. 9, 100 ng of ATL8/PAL-LUC reporter and 5 ng of the expression plasmid encoding ER3M were co-transfected into HepG2 cells. Five ng of *Renilla* luciferase expression plasmid was used as an internal standard. OHT or tamoxifen was added to the culture medium to the indicated final concentrations, and the cells were harvested after 48 hours and assayed for luciferase activity. The data represent the mean±S.E. for three independent transfections.

Example 11

Fusion of VP16 to ER3M

Figure 10:
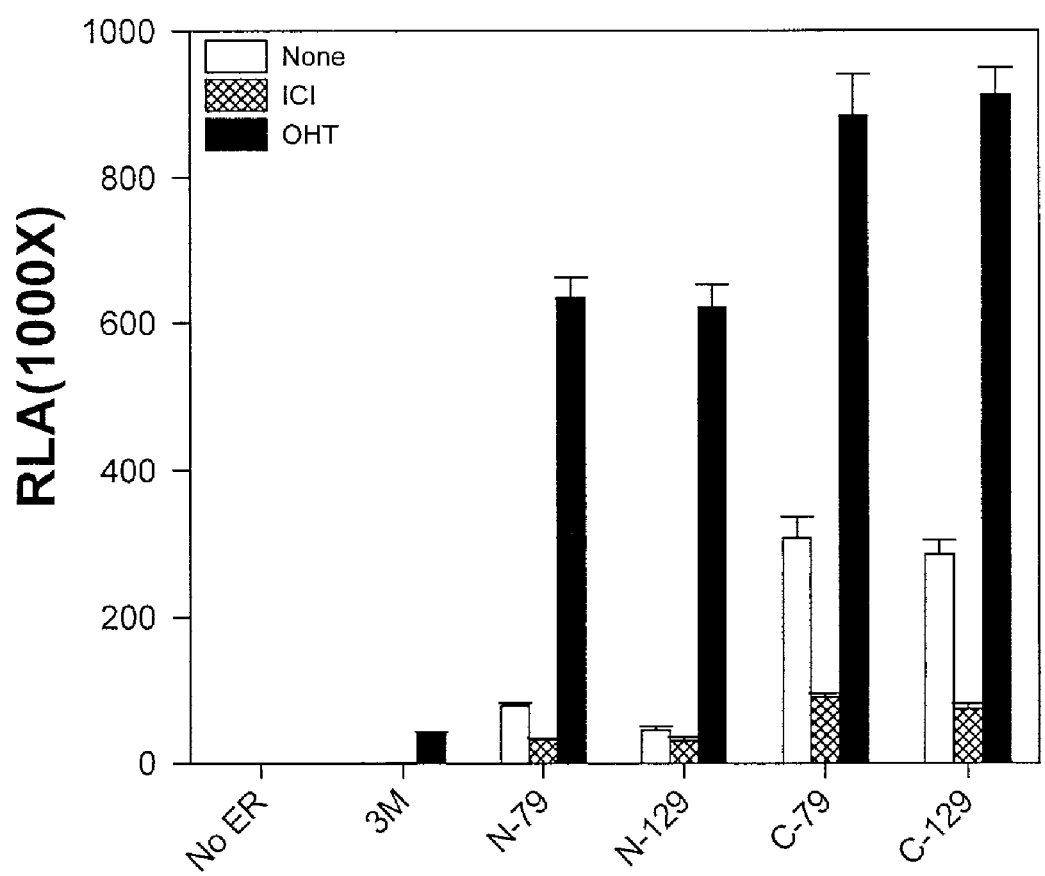
FIG. 10 shows a graph that demonstrates that the fusion of 79 or 129 carboxy residues of VP16 to ER3M greatly enhances transactivation by OHT; ICI 182,780 inhibits transactivation by the unliganded fusion proteins.

Eight copies of PAL sequences in the ATL8 reporter increased the signal produced by wild type ER, which has a very low affinity for the PAL (FIG. 4), but failed to dramatically increase the fold induction or total transactivation produced by OHT bound to ER3M and 4.3 (FIGS. 4 and 8). A stronger transactivator would be therefore be necessary to achieve higher levels of transactivation. The strongest known transcription activator for attachment to eukaryotic gene regulatory proteins is VP16 (Triezenberg et al., 1988). This transactivator functions in a broad range of different cell lines. Fusing the 79 amino acid core VP16 sequence and the extended 129 amino acid VP16 sequence to the amino terminal end (termed N-79 or N-129, respectively), or the carboxy terminal end (termed C-79 and C-129, respectively) of the ER3M mutant resulted in chimeric ERs. The same CMV promoter as for ER3M drove all these chimeras expression, so that they could be compared to ER3M. These chimeras were compared to ER3M for their ability to activate transcription in the presence and absence of OHT or the pure antiestrogen, ICI 182,780. Transactivation with the four different fusion proteins in the presence of OHT was much higher than with ER3M, increasing from 15-fold with N-129 to 22-fold with C-129 (FIG. 10). While transactivation in the presence of OHT increased, basal transactivation also increased dramatically, and the fold induction by OHT with these fusion proteins is low, from less than three-fold with C-79 to 13.8-fold with N-129 (FIG. 10). This dramatically increased basal transactivation was decreased by addition of ICI 182,780 (FIG. 10), suggesting that traces of estrogen in the culture medium were partly responsible for basal activity.

In FIG. 10, 50 ng of ATL8/PAL-LUC and 5 ng of *Renilla* luciferase expression plasmid as an internal standard were co-transfected with either no ER expression plasmid (No ER), 4 ng of expression plasmids encoding ER3M, or the four fusion proteins into HepG2 cells. Transactivation in the presence of ethanol vehicle (open bars), 10 nM ICI 182,780 (cross-hatched bars) and OHT (filled bars) was determined. The data represent the mean±S.E.M for three independent transfections.

Example 12

Figure 11:
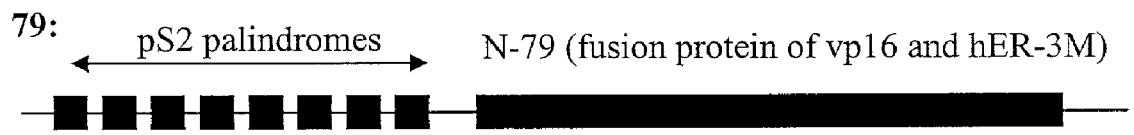
FIG. 11 shows schematics of the ATL8/PAL-N-79 and ATL8/PAL-LUC constructs used for auto-regulated gene expression. Eight copies of pS2 PAL control the expression of both the fusion protein (N-79) and the reporter gene.
Figure 11:
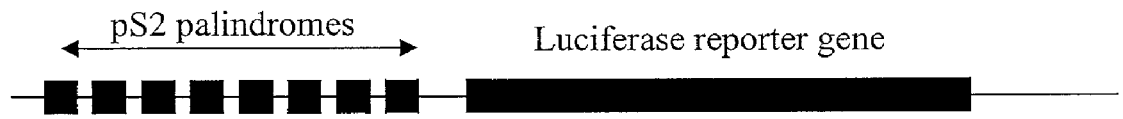

Tight Regulation of Protein Production Using an Autoregulated 4-Hydroxytamoxifen Expression System Since the expression of the fusion proteins used so far was driven by the highly active CMV promoter, their higher level of basal transactivation might be due to their expression in the absence of OHT. To produce a more tightly controlled regulatory system with negligible basal expression in the absence of added OHT, an autoregulated expression system was developed. We therefore constructed and tested a plasmid containing 8 copies of pS2 PAL driving expression of N-79 (a chimera of the ER3M mutant and the N-terminal 79 amino acid transactivator from VP16; FIG. 11, ATL8/PAL-N-79). A second plasmid also containing 8 copes of pS2 PAL drives expression of the reporter gene (FIG. 11, ATL8/PAL-LUC). In the absence of OHT, basal transcription from the promoter leads to production of extremely low levels of N-79. Without OHT to elicit strong transcription activation when bound to the N-79 chimera, there is negligible activation of the luciferase test gene (FIG. 11, ATL8/PAL-LUC) whose expression is also driven by 8 copies of pS2 PAL. When OHT is added to the culture medium, transactivation by the N-79 chimera bound to the 8 pS2 PAL elements in its own expression plasmid is greatly increased, resulting in increased levels of N-79 protein. Since this newly-synthesized protein binds to the 8 pS2 PAL elements and further increases its own production, an upwardly cycling autoregulated system for production of the regulatory protein results. The OHT:N-79 protein also binds to the 8 pS2 PAL elements driving production of the mRNA that encodes the luciferase test gene.

Figure 12:
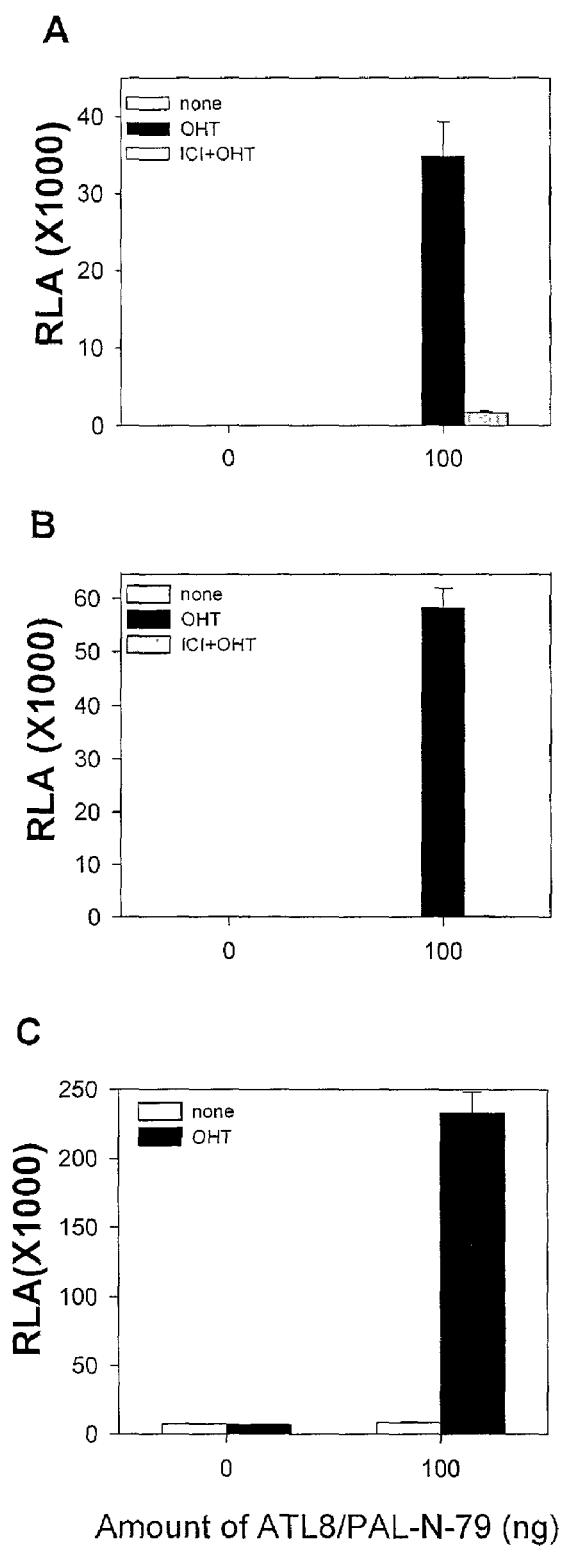
FIGS. 12A–12C present graphs that show that the auto-regulated expression system is tightly controlled and functions in many different cell types, including HepG2 cells (FIG. 12A), 231 human breast cancer cells (FIG. 12B) and CHO—S cells (FIG. 12C).

This system has two important advantages over a system for constitutive expression of N-79: (i) Because only very low levels of unliganded N-79 are present in the absence of OHT, there is extremely low basal expression in the absence of OHT. The increase in luciferase activity upon addition of OHT was 813-fold in 231 human breast cancer cells (FIG. 12B) and 1027-fold in HepG2 human hepatoblastoma cells (FIG. 12A). (ii) The system can be used in diverse cell types. Because the potent VP16 transactivator is active in a wide variety of cell lines, excellent activity was obtained in both 231 and HepG2 cells. In CHO—S cells, a 28-fold induction was also observed (FIG. 12, C). In the presence of a 100-fold excess of ICI 182,780 over OHT, transactivation by OHT was blocked, indicating that ICI 182,780 is still an antogonist to the fusion protein.

In FIG. 12, 100 ng of ATL8/PAL-LUC reporter, 5 ng of *Renilla* luciferase expression plasmid as an internal standard and the indicated amount of ATL8/PAL-N-79 plasmid were co-transfected into HepG2 cells (panel A); 1,000 ng ATL8/PAL-LUC reporter, 5 ng of *Renilla* luciferase expression plasmid as an internal standard and the indicated amount ATL8/PAL-N-79 plasmid were co-transfected into 231 cells (panel B); and 900 ng of ATL8/PAL-LUC reporter, 1 ng of *Renilla* luciferase expression plasmid as an internal standard and the indicated amount ATL8/PAL-N-79 plasmid were co-transfected into CHO—S cells (panel C). The transactivation in the presence of ethanol vehicle (open bars); 10 nM of OHT (filled bars); or 10 nM OHT and 1,000 nM ICI 182,780 (grey bars) were determined. The data represent the mean±S.E.M. of three independent transfections.

Example 13

Figure 13:
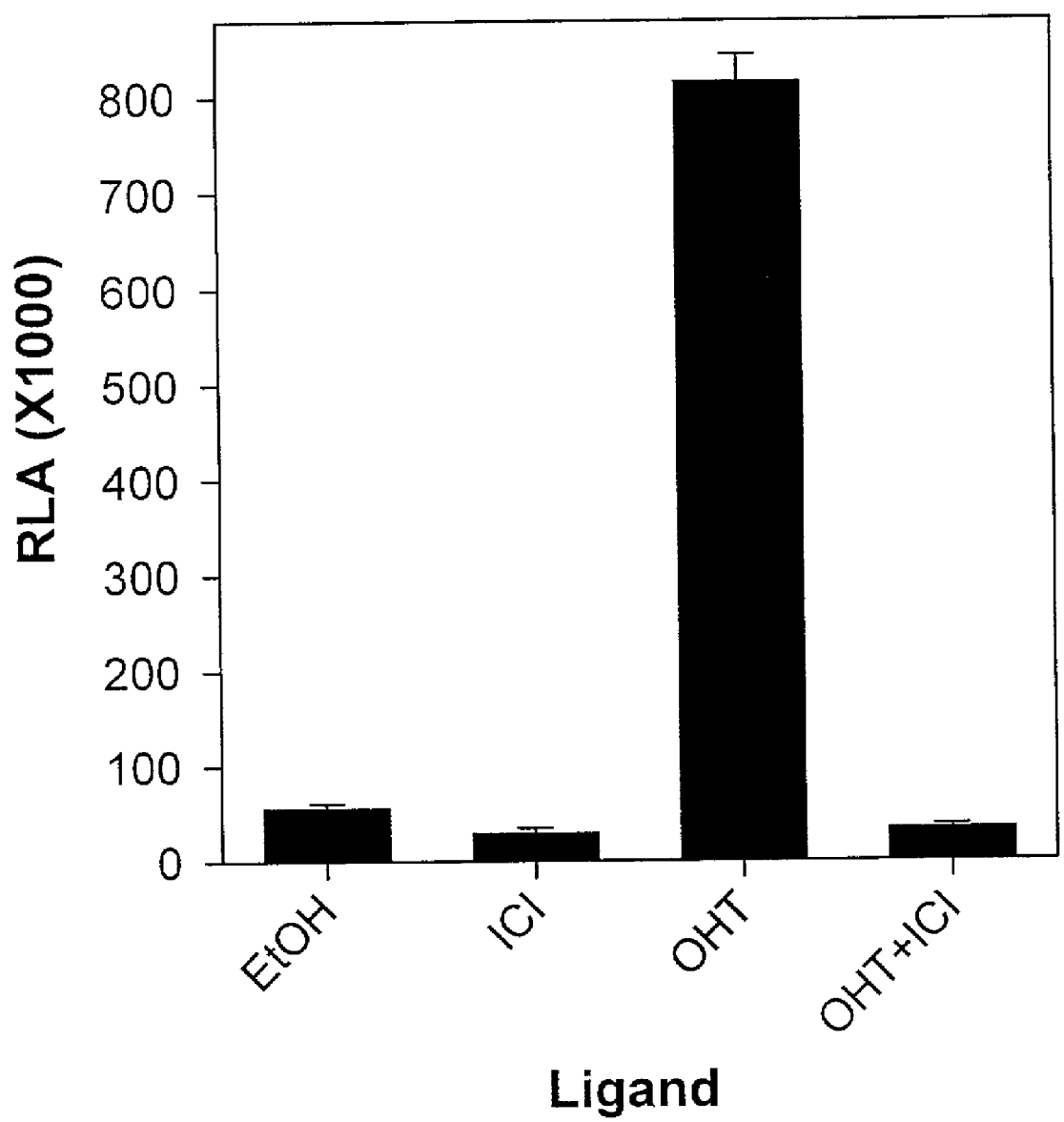
FIG. 13 shows a graph that shows that the ICI 182,780 blocks transactivation by added OHT and by the trace amounts of residual estrogen in cell culture medium.
Figure 14:
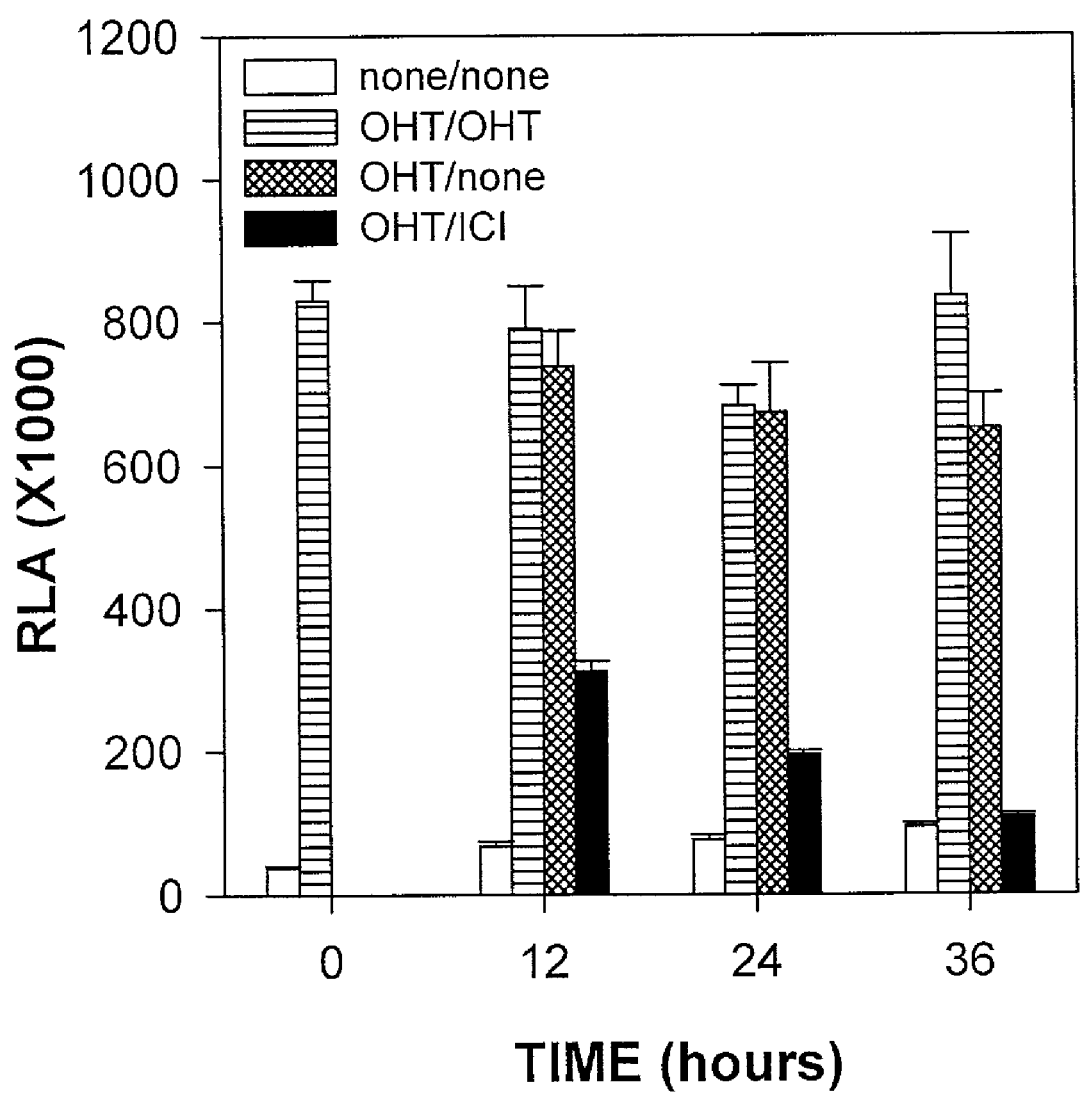
FIG. 14 presents a graph that shows that ICI 182,780 can be used as an antagonist to turn off a previously activated pS2 PAL promoter, reducing activation to basal levels after 36 hours of administration.

ICI 182,780 Prevents OHT from Activating Transcription by Binding to the ER-3M-VP16 Fusion Protein Previously-described regulated gene expression systems have only one regulating factor that either increases or decreases gene expression. An inhibitor that would block the activity of the regulating factor would be desirable in a regulated expression system. One problem in such systems is the difficulty of removing regulating factors from cells in culture and tissues. ICI 182,780 has been established as a pure antagonist and blocks ER translocation into the nucleus (Htun et al., 1999). When ER3M is expressed in MCF-7 cells (FIG. 5), and ER3M-VP16 fusion protein is expressed in HepG2 cells (FIG. 10), ICI 182,780 prevents traces of estrogen in the culture medium from activating reporter genes. In the results obtained when using the autoregulated system shown in FIG. 12, ICI 182,780 dramatically blocked the OHT stimulation of reporter gene expression in both HepG2 cells and 231 breast cancer cells. These data suggested the possibility of using ICI 182,780 as an inhibitor in this gene expression system. To further confirm this data and to test whether ICI 182,780 could suppress expression from a previously activated pS2 PAL reporter gene, HepG2 cells and the CMV promoter driving N-79 were used. In these cells, the reporter system results in very high transactivation. FIG. 13 shows that 10 nM ICI 182,780 can reduce basal transactivation by almost half, and a 100-fold excess of ICI can completely block 10 nM OHT stimulation of ATL8/PAL-LUC expression. In FIG. 14, 10 nM OHT was used to stimulate ATL8/PAL-LUC expression for 36 hours, and then OHT was attempted to be removed by washing the cells. Reporter gene activity in the presence of ethanol vehicle (OHT/none), 10 nM OHT (OHT/OHT) and or 100 nM ICI (OHT/ICI) at different time points were compared. There was almost no difference between the samples exposed to OHT/OHT and OHT/none, suggesting that it is quite difficult to remove OHT from the cells by washing and medium replacement. By adding ICI 182,780, which competes with residual OHT and exchanges with OHT bound to the ER3M-VP16 fusion protein, 12 and 24 hours after removal of OHT, reporter gene activity was reduced 58% and 71% (relative to no ligand; OHT/none), respectively. Thirty-six hours later, reporter acitivity almost reached basal levels (none/none). These data indicate that ICI 182,780 can be used as a antogonist to turn OFF the pS2 PAL promoter.

These data demonstrate that simply washing cells is insufficient to turn off the activated promoter: sufficient residual OHT maintains transcription unabated. When an excess of ICI 182,780 is added, it exchanges with OHT bound to the ER3M-VP16 chimera and prevents it from activating transcription. Since the expression system was activated before addition of the ICI 182,780, even though there is a complete shut-off of new transcription in the presence of ICI 182,780, there is substantial residual luciferase activity. As this protein is degraded and no new luciferase is synthesized in the presence of ICI 182,780, luciferase activity returns to basal levels. Thus, addition of ICI 182,780 to the culture medium shuts off expression from the TAS, allowing this system to go from OFF to ON, and then back to OFF in response to small molecules.

In FIGS. 13 and 14, HepG2 cells were co-transfected by calcium phosphate co-precipitation (Ausubel et al., 1987). Transfections contained 50 ng of ATL8/PAL-luciferase reporter, 4 ng of CMV-N-79, 5 ng of the *Renilla* luciferase internal standard and 1,950 ng of PTZ18U DNA as carrier. In FIG. 13, after glycerol shock, cells were maintained in medium containing either ethanol vehicle alone, 10 nM ICI 182,780, 10 nM OHT, or 10 nM OHT with 1,000 nM ICI 182,780. Forty-eight hours after transfection, cell extracts were prepared and dual luciferase activity measured. The data represent the mean±S.E for relative luciferase activity (RLA) from three separate transfections. In FIG. 14, after glycerol shock, the cells were maintained in medium containing either ethanol vehicle (none/none, open bars) or 10 n-M OHT (OHT/OHT, striped bars) for 36 hours. Samples were taken for later assay at this point, which is designated 0 hours (This represents basal activity and OHT activated samples). To test whether the OHT activated promoter could be silenced, the medium was removed, the cells were maintained in fresh medium without any ligand for 12 minutes and then the medium was removed. Control cells were maintained in medium containing ethanol vehicle (none/none). The cells previously induced with OHT were then maintained in medium containing either 10 nM OHT (OHT/OHT), ethanol vehicle (OHT/none, speckled bars), or 100 nM ICI 182,780 (OHT/ICI, filled bars). Cells were harvested at 12, 24 and 36 hours, extracts were prepared and assayed for luciferase activity. The data represent the average of of three seperate transfections±S.E.

Example 14

Summary of TAS's

The combination of the 4.3 and 3M ER mutants that exhibit increased affinity for pS2 PAL relative to wild-type ER, and the observations made using the synthetic pS2 PAL ERE provides a novel ligand-dependent regulatory system with several attractive and useful features. (1) The level of regulation using the pS2 PAL reporters and the ER mutants is impressive, with 70–1000-fold, OHT-mediated activation of transcription on different versions of pS2 PAL reporters. (2) When OHT is bound to ER, the ER3M and ER 4.3 mutants are specific for pS2 PAL. There is little OHT-mediated transcription from the cERE, and the 3M and 4.3 mutants showed no detectable binding to, or transcription from, the Bcl2 and TGF α1 EREs. (3) Tamoxifen's long-term use as a breast cancer therapeutic and chemopreventive agent provides a wealth of information on clinical effects. (4) An antagonist, ICI 182,780, can be used to shut off TAS gene expression at a desired time. This allows for production of a timed pulse of a protein of interest.

REFERENCES

WO 90/10448. 1990. Covalent conjugates of lipid and oligonucleotide.
WO 91/06629. 1991. Oligonucleotide analogs with novel linkages.
Ali, S., D. Metzger, J. M. Bornert, and P. Chambon. 1993. Modulation of transcriptional activation by ligand-dependent phosphorylation of the human oestrogen receptor A/B region. Embo J. 12:1153–60.
Austin, C. P., and C. L. Cepko. 1990. Cellular migration patterns in the developing mouse cerebral cortex. Development. 110:713–732.
Ausubel, F. M., R. Brent, R. E. Kingston, D. D. Moore, et al. 1987. Current protocols in molecular biology. John Wiley & Sons, New York.
Baim, S. B., M. A. Labow, A. J. Levine, and T. Shenk. 1991. A chimeric mammalian transactivator based on the lac repressor that is regulated by temperature and isopropyl beta-D-thiogalactopyranoside. Proc Natl Acad Sci USA. 88:5072–6.
Barkhem, T., C. Andersson-Ross, M. Hoglund, and S. Nilsson. 1997. Characterization of the "estrogenicity" of tamoxifen and raloxifene in HepG2 cells: regulation of gene expression from an ERE controlled reporter vector versus regulation of the endogenous SHBG and PS2 genes. J Steroid Biochem Mol Biol. 62:53–64.
Bartel, D. P., and J. W. Szostak. 1993. Isolation of new ribozymes from a large pool of random sequences [see comment]. Science. 261:1411–8.
Bechtold, N., and G. Pelletier. 1998. In planta Agrobacterium-mediated transformation of adult Arabidopsis thaliana plants by vacuum infiltration. Methods Mol Biol. 82:259–66.

Becker, D. M., and L. Guarente. 1991. High-efficiency transformation of yeast by electroporation. Methods Enzymol. 194:182–187.
Beggs, J. D. 1978. Transformation of yeast by a replicating hybrid plasmid. Nature. 275:104–109.
Belshaw, P. J., S. N. Ho, G. R. Crabtree, and S. L. Schreiber. 1996. Controlling protein association and subcellular localization with a synthetic ligand that induces heterodimerization of proteins. Proc Natl Acad Sci USA. 93:4604–7.
Berns, A., R. Mandag, and H. Te Riele. WO 93/04169. 1993. GENE TARGETING IN ANIMAL CELLS USING ISOGENIC DNA CONSTRUCTS.
Bodine, D. M., K. T. McDonagh, N. E. Seidel, and A. W. Nienhuis. 1991. Survival and retrovirus infection of murine hematopoietic stem cells in vitro: effects of 5-FU and method of infection. Exp. Hematol. 19:206–212.
Bradley. 1987. Teratocarcinomas and Embryonic Stem Cells: A Practical Approach. Oxford University Press, Inc., Oxford. 268 pp.
Bradley, A. 1991. Modifying the mammalian genome by gene targeting. Curr Opin Biotechnol. 2:823–9.
Braselmann, S., P. Graninger, and M. Busslinger. 1993. A selective transcriptional induction system for mammalian cells based on Gal4-estrogen receptor fusion proteins. Proc Natl Acad Sci USA. 90:1657–61.
Capecchi, M. R. 1980. High efficiency transformation by direct microinjection of DNA into cultured mammalian cells. Cell. 22:479.
Carter, P. 1986. Site-directed mutagenesis. Biochem J. 237:1–7.
Cech, T. R., F. L. Murphy, and A. J. Zaug. U.S. Pat. No. 5,116,742. 1992. RNA ribozyme restriction endoribonucleases and methods.
Cech, T. R., A. J. Zaug, and M. D. Been. U.S. Pat. No. 4,987,071. 1991. RNA ribozyme polymerases, dephosphorylases, restriction endoribonucleases and methods.
Cepko, C. L., B. E. Roberts, and R. E. Mulligan. 1984. Construction and applications of a highly transmissible murine retrovirus shuttle vector. Cell. 37:1053–1062.
Chaney, W. G., D. R. Howard, J. W. Pollard, S. Sallustio, et al. 1986. High-frequency transfection of CHO cells using Polybrene. Somatic Cell Mol. Genet 12:237.
Chen, C., and H. Okayama. 1988. Calcium phosphate-mediated gene transfer: A highly efficient system for stably transforming cells with plasmid DNA. BioTechniques. 6:632–638.
Chen, S. H., H. D. Shine, J. C. Goodman, R. G. Grossman, et al. 1994. Gene therapy for brain tumors: regression of experimental gliomas by adenovirus-mediated gene transfer in vivo. Proc Natl Acad Sci USA. 91:3054–7.
Chusacultanachai, S., K. A. Glenn, A. O. Rodriguez, E. K. Read, et al. 1999. Analysis of estrogen response element binding by genetically selected steroid receptor DNA binding domain mutants exhibiting altered specificity and enhanced affinity. J Biol Chem. 274:23591–8.
Cohen, S. M. N., A. C. Y. Chang, and L. Hsu. 1972. Nonchromosomal antibiotic resistance in bacteria: Genetic transformation of Escherichia coli by R-factor DNA. Proc. Natl. Acad. Sci. USA. 69:2110.
Danielian, P. S., R. White, J. A. Lees, and M. G. Parker. 1992. Identification of a conserved region required for hormone dependent transcriptional activation by steroid hormone receptors. Embo J. 11:1025–33.
David, M. 1995. Transcription factors in interferon signaling. Pharmacol Ther. 65:149–61.

Deuschle, U., R. A. Hipskind, and H. Bujard. 1990. RNA polymerase II transcription blocked by *Escherichia coli* lac repressor. *Science.* 248:480–3.

Elroy-Stein, O., and B. Moss. 1990. Cytoplasmic expression system based on constitutive synthesis of bacteriophage T7 RNA polymerase in mammalian cells. *Proc. Natl. Acad. Sci. USA.* 87:6743–6747.

Eppstein, D. A., E. B. Fraser-Smith, and T. R. Mattews. U.S. Pat. No. 4,522,811. 1985. Serial injection of muramyldipeptides and liposomes enhances the anti-infective activity of muramyldipeptides Serial injection of muramyldipeptides and liposomes enhances the anti-infective activity of muramyldipeptides.

Escudero, J., and B. Hohn. 1997. Transfer and integration of T-DNA without cell injury in the host plant. *Plant Cell.* 9:2135–2142.

Evans, R., R. D. Palmiter, and R. L. Brinster. U.S. Pat. No. 4,870,009. 1989. Method of obtaining gene product through the generation of transgenic animals.

Fekete, D. M., and C. L. Cepko. 1993. Retroviral infection coupled with tissue transplantation limits gene transfer in the chick embryo. *Proc. Natl. Acad. Sci. USA.* 90:2350–2354.

Felgner, P. L., T. R. Gadek, M. Holm, R. Roman, et al. 1987. Lipofectin: A highly efficient, lipid-mediated DNA/transfection procedure. *Proc. Natl. Acad. Sci. USA.* 84:7413–7417.

Filmus, J., J. Remani, and M. H. Klein. 1992. Synergistic induction of promoters containing metal- and glucocorticoid-responsive elements. *Nucleic Acids Res.* 20:2755–60.

Finer, J. J., K. R. Finer, and T. Ponappa. 1999. Particle bombardment-mediated transformation. *Current Topics in microbiology and immunology.* 240:59–80.

Fromm, M., L. P. Taylor, and V. Walbot. 1985. Expression of genes transferred into monocot and dicot plant cells by electroporation. *Proc. Natl. Acad. Sci. USA.* 82:5824–5828.

Fujita, T., H. Shubiya, T. Ohashi, K. Yamanishi, et al. 1986. Regulation of human interleukin-2 gene: Functional DNA sequences in the 5' flanking region for the gene expression in activated T lymphocytes. *Cell.* 46:401–407.

Gautier, C., F. Morvan, B. Rayner, T. Huynh-Dinh, et al. 1987. Alpha-DNA. IV: Alpha-anomeric and beta-anomeric tetrathymidylates covalently linked to intercalating oxazolopyridocarbazole. Synthesis, physicochemical properties and poly (rA) binding. *Nucleic Acids Res.* 15:6625–41.

Gennaro, A. R. 2000. Remington: The science and practice of pharmacy. Lippincott, Williams & Wilkins, Philadelphia, Pa.

Gietz, R. D., R. A. Woods, P. Manivasakam, and R. H. Schiestl. 1998. Growth and transformation of *Saccharomyces cerevisiae*. In Cells: A laboratory manual. Vol. I.D. Spector, R. Goldman, and L. Lemwand, editors. Cold Spring Harbor Press, Cold Spring Harbor, N.Y.

Gingrich, J. R., and J. Roder. 1998. Inducible gene expression in the nervous system of transgenic mice. *Annu Rev Neurosci.* 21:377–405.

Gossen, M., and H. Bujard. 1992. Tight control of gene expression in mammalian cells by tetracycline-responsive promoters. *Proc Natl Acad Sci USA.* 89:5547–51.

Gossen, M., S. Freundlieb, G. Bender, G. Muller, et al. 1995. Transcriptional activation by tetracyclines in mammalian cells. *Science.* 268:1766–9.

Graham, F. L., and A. J. van der Eb. 1973. A new technique for the assay of infectivity of human adenovirus 5 DNA. *Virology.* 52:456-.

Hanahan, D. 1983. Studies on transformation of Escherichia coli with plasmids. *J. Mol. Biol.* 166:557–580.

Hansen, G., and M.-D. Chilton. 1999. Lessons in gene transfer to plants by a gifted microbe. *Curr. Top. Microbiol. Immunol.* 240:21–57.

Hansen, G., and M. S. Wright. 1999. Recent advances in the transformation of plants. *Trends Plant Sci.* 4:226–231.

Haseloff, J., and W. L. Gerlach. 1988. Simple RNA enzymes with new and highly specific endoribonuclease activities. *Nature.* 334:585–91.

Helene, C. 1991. The anti-gene strategy: control of gene expression by triplex-forming-oligonucleotides. *Anticancer Drug Des.* 6:569–84.

Helene, C., N. T. Thuong, and A. Harel-Bellan. 1992. Control of gene expression by triple helix-forming oligonucleotides. The antigene strategy. *Ann N Y Acad Sci.* 660:27–36.

Hinnen, A., J. B. Hicks, and G. R. Fink. 1978. Transformation of yeast. Proc. Natl. Acad. Sci USA. 75:1929–1933.

Hoffman, F. 1996. Laser microbeams for the manipulation of plant cells and subcellular structures. *Plant Sci* 113:1–11.

Hogan, B., Beddington, R., Costantini, F., Lacy, E. 1994. Manipulating the Mouse Embryo A Laboratory Manual. Cold Spring Harbor Laboratory Press. 500 pp.

Htun, H., L. T. Holth, D. Walker, J. R. Davie, et al. 1999. Direct visualization of the human estrogen receptor alpha reveals a role for ligand in the nuclear distribution of the receptor. *Mol Biol Cell.* 10:471–86.

Hyrup, B., and P. E. Nielsen. 1996. Peptide nucleic acids (PNA): synthesis, properties and potential applications. *Bioorg Med Chem.* 4:5–23.

Inoue, H., Y. Hayase, A. Imura, S. Iwai, et al. 1987a. Synthesis and hybridization studies on two complementary nona(2'-O-methyl)ribonucleotides. *Nucleic Acids Res.* 15:6131–48.

Inoue, H., Y. Hayase, S. Iwai, and E. Ohtsuka. 1987b. Sequence-dependent hydrolysis of RNA using modified oligonucleotide splints and RNase H. *FEBS Lett.* 215:327–30.

Ishiura, M., S. Hirose, T. Uchida, Y. Hamada, et al. 1982. Phage particle-mediated gene transfer to cultured mammalian cells. *Molecular and Cellular Biology.* 2:607–616.

Ito, H., Y. Fukuda, K. Murata, and A. Kimura. 1983. Transformation of intact yeast cells treated with alkali cations. *J. Bacteriol.* 153:163–168.

Kato, S., H. Endoh, Y. Masuhiro, T. Kitamoto, et al. 1995. Activation of the estrogen receptor through phosphorylation by mitogen-activated protein kinase. *Science.* 270:1491–4.

Kaufman, R. J., P. Murtha, D. E. Ingolia, C.-Y. Yeung, et al. 1986. Selection and amplification of heterologous genes encoding adenosine deammase in mammalian cells. *Proc. Natl. Acad Sci. USA.* 83:3136–3140.

Kawai, S., and M. Nishizawa. 1984. New procedure for DNA transfection with polycation and dimethyl sulfoxide. *Mol. Cell. Biol.* 4:1172.

Kothary, R., S. Clapoff, S. Darling, M. D. Perry, et al. 1989. Inducible expression of an hsp68-lacZ hybrid gene mi transgenic mice. *Development.* 105:707–14.

Kucherlapati, R. S., B. H. Koller, and O. Smithies. WO 91/01140. 1991. HOMOLOGOUS RECOMBINATION FOR UNIVERSAL DONOR CELLS AND CHIMERIC MAMMALIAN HOSTS.

Kuhn, R., F. Schwenk, M. Aguet, and K. Rajewsky. 1995. Inducible gene targeting in mice. *Science.* 269:1427–9.

Kuo, W. L., B. D. Gehm, M. R. Rosner, W. Li, et al. 1994. Inducible expression and cellular localization of insulin-degrading enzyme in a stably transfected cell line. *J Biol Chem.* 269:22599–606.

Labow, M. A., S. B. Baim, T. Shenk, and A. J. Levine. 1990. Conversion of the lac repressor into an allosterically regulated transcriptional activator for mammalian cells. *Mol Cell Biol.* 10:3343–56.

Lakso, M., B. Sauer, B. Mosinger, E. J. Lee, et al. 1992. Targeted oncogene activation by site-specific recombination in transgenic mice. *Proc Natl Acad Sci USA.* 89:6232–6.

Le Mouellic, H., and P. Brullet. WO 90/11354. 1990. Process for the specific replacement of a copy of a gene present in the receiver genome via the integration of a gene.

Leder, P., and T. A. Stewart. U.S. Pat. No. 4,736,866. 1988. Transgenic non-human animals.

Leduc, N., and e. al. 1996. Isolated maize zygotes mimic in vivo embryogenic development and express microinjected genes when cultured in vitro. *Dev. Biol.* 10:190–203.

Lemaitre, M., B. Bayard, and B. Lebleu. 1987. Specific antiviral activity of a poly(L-lysine)-conjugated oligodeoxyribonucleotide sequence complementary to vesicular stomatitis virus N protein mRNA initiation site. *Proc Natl Acad Sci USA.* 84:648–52.

Lemischka, I. R., D. H. Raulet, and R. C. Mulligan. 1986. Developmental potential and dynamic behavior of hematopoietic stem cells. *Cell.* 45:917–927.

Letsinger, R. L., G. R. Zhang, D. K. Sun, T. Ikeuchi, et al. 1989. Cholesteryl-conjugated oligonucleotides: synthesis, properties, and activity as inhibitors of replication of human immunodeficiency virus in cell culture. *Proc Natl Acad Sci USA.* 86:6553–6.

Levenson, A. S., W. H. Catherino, and V. C. Jordan. 1997. Estrogenic activity is increased for an antiestrogen by a natural mutation of the estrogen receptor. *J Steroid Biochem Mol Biol.* 60:261–8.

Levenson, A. S., and V. C. Jordan. 1998. The key to the antiestrogenic mechanism of raloxifene is amino acid 351 (aspartate) in the estrogen receptor. *Cancer Res.* 58:1872–5.

Li, E., T. H. Bestor, and R. Jaenisch. 1992. Targeted mutation of the DNA methyltransferase gene results in embryonic lethality. *Cell.* 69:915–26.

Littlefield, J. W. 1964. Selection of hybrids from matings of fibroblasts in vitro and their presumed recombinants. *Science.* 145:709–710.

Lopata, M. A., D. W. Cleveland, and B. Sollner-Webb. 1984. High-level expression of a chloramphenicol acetyltransferase gene by DEAEdextran-mediated DNA transfection couled with a dimethylsulfoxide or glycerol shock treatment. *Nucleic Acids Research.* 12:5707.

Luckow, V. A. 1991. Cloning and expression of heterologous genes in insect cells with baculovirus vectors. In Recombinant DNA technology and applications. A. Prokop, R. K. Bajpai, and C. Ho, editors. McGraw-Hill, New York. 97–152.

Maher, L. J. 1992. DNA triple-helix formation: an approach to artificial gene repressors? *Bioessays.* 14:807–15.

Mandel, M., and A. Higa. 1970. Calcium-dependent bacteriophage DNA infection. *J. Mol. biol.* 53:159–162.

Martin, M. B., T. F. Franke, G. E. Stoica, P. Chamboi, et al. 2000. A role for Akt in mediating the estrogenic functions of epidermal growth factor and insulin-like growth factor I. *Endocrinology.* 141:4503–11.

Martinez, E., and W. Wahli. 1989. Cooperative binding of estrogen receptor to imperfect estrogen-responsive DNA elements correlates with their synergistic hormone-dependent enhancer activity. *Embo J.* 8:3781–91.

Mattick, S., K. Glenn, G. de Haan, and D. J. Shapiro. 1997. Analysis of ligand dependence and hormone response element synergy in transcription by estrogen receptor. *J Steroid Biochem Mol Biol.* 60:285–94.

McInerney, E. M., and B. S. Katzenellenbogen. 1996. Different regions in activation function-1 of the human estrogen receptor required for antiestrogen- and estradiol-dependent transcription activation. *J Biol Chem.* 271:24172–8.

Miller, A. D., and C. Buttimore. 1986. Redesign of retrovirus packaging cell lines to avoid recombination leading to helper virus production. *Mol. Cell biol.* 6:2895–2902.

Miller, L. K. 1988. Baculoviruses as gene expression vectors. *Annu. Rev. Microbiol.* 42:177–199.

Nabel, E. G., and G. J. Nabel. U.S. Pat. No. 5,328,470. 1994. Treatment of diseases by site-specific instillation of cells or site-specific transformation of cells and kits therefor.

Neumann, E., M. Schaefer-Ridder, Y. Wang, and P. H. Hofschneider. 1982. Gene transfer into mouse lyoma cells by electroporation in high electric fields. *EMBO J.* 1:841–845.

No, D., T. P. Yao, and R. M. Evans. 1996. Ecdysone-inducible gene expression in mammalian cells and transgenic mice. *Proc Natl Acad Sci USA.* 93:3346–51.

Nunez, A. M., M. Berry, J. L. Imler, and P. Chambon. 1989. The 5' flanking region of the pS2 gene contains a complex enhancer region responsive to oestrogens, epidermal growth factor, a tumour promoter (TPA), the c-Ha-ras oncoprotein and the c-jun protein. *Embo J.* 8:823–9.

O'Gorman, S., D. T. Fox, and G. M. Wahl. 1991. Recombinase-mediated gene activation and site-specific integration in mammalian cells. *Science.* 251:1351–5.

O'Reilly, D. R., L. K. Miller, and V. A. Luckow. 1992. Baculovirus expression vectors. W. H. Freeman and Company, New York.

Ou-Lee, T. M., R. Turgeon, and R. Wu. 1986. Uptake and expression of a foreign gene linked to either a plant virus or Drosophila promoter in protoplasts of rice, wheat and sorghum. *Proc. Natl. Acad. Sci. USA.* 83:6815–6819.

Palmer, T. D., R. A. Hock, W. R. A. osborne, and A. D. Miller. 1987. Efficient retrovirus-mediated transfer and expression of a human adenosine deaminase gene in diploid skin fibroblasts from an adenosie-deficient human. *Proc. Natl Acad. Sci. USA.* 84:1055–1059.

Pardridge, W., and P. Schimmel. WO89/10134. 1989. Chimeric peptides for neuropeptide delivery through the blood-brain barrier.

Pear, W., G. Nolan, M. Scott, and D. Baltimore. 1993. Production of high-titer helper-free retroviruses by transient transfection. *Proc. Natl. Acad. Sci. USA.* 90:8392–8396.

Perry-O'Keefe, H., X. W. Yao, J. M. Coull, M. Fuchs, et al 1996. Peptide nucleic acid pre-gel hybridization: an alternative to southern hybridization. *Proc Natl Acad Sci USA.* 93:14670–5.

Peyrade, F., M. Frenay, M. C. Etienne, F. Ruch, et al. 1996. Age-related difference in tamoxifen disposition. *Clin Pharmacol Ther.* 59:401–10.

Ponglikitmongkol, M., J. H. White, and P. Chambon. 1990. Synergistic activation of transcription by the human estrogen receptor bound to tandem responsive elements. *Embo J.* 9:2221–31.

Potter, H. 1988. Electroporation in biology: Methods, applications,, and instrumentation. *Analytical Biochemistry.* 174:361–373.

Potter, H., L. Weir, and P. Leder. 1984. Enhancer-dependent expression of human kappa immunoglobulin genes introduced into mouse pre-B lymphocytes by electroporation. *Proc. Natl. Acad. Sci. USA.* 81:7161–7165.

Rassoulzadegan, M., B. Binetruy, and F. Cuzin. 1982. High frequency of gene transfer after fusion between bacteria and eukaryotic cells. *Nature.* 295:257.

Rhodes, C. A., D. A. Pierce, I. J. Mettler, D. Mascarenhas, et al. 1988. Genetically transformed maize plants from protoplasts. *Science.* 240:204–207.

Rose, J. K., L. Buonocore, and M. Whitt. 1991. A new cationic liposome reagent mediating nearly quantitative transfection of animal cells. *BioTechniques.* 10:520–525.

Sandri-Goldin, R. M., A. L. Goldin, J. C. Glorioso, and M. Levine. 1981. High-frequency transfer of cloned herpes simplex virus type I sequences to mammalian cells by protoplast fusion. *Mol. Cell. Biol.* 1:7453–752.

Saunders, J. A., B. F. Matthews, and P. D. Miller. 1989. Plant gene transfer using electrofusion and electroporation. In Electroporation and electrofusion in cell biology. E. Neumann, A. E. Sowers, and C. A. Jordan, editors. Plenum Press, New York. 343–354.

Schaffner, W. 1980. Direct transfer of cloned genes from bacteria to mammalian cells. *Proc. Natl. Acad. Sci. USA.* 77:2163.

Schweinfest, C. W., C. L. Jorcyk, S. Fujiwara, and T. S. Papas. 1988. A heat-shock-inducible eukaryotic expression vector. *Gene.* 71:207–10.

Selden, R. F., K. Burke-Howie, M. E. Rowe, H. M. Goodman, et al. 1986. Human growth hormone as a reporter gene in regulation studies employing transient gene expression. *Molecular and Cellular Biology.* 6:3173–3179.

Shang, Y., X. Hu, J. DiRenzo, M. A. Lazar, et al 2000. Cofactor dynamics and sufficiency in estrogen receptor-regulated transcription. *Cell.* 103:843–52.

Shiau, A. K., D. Barstad, P. M. Loria, L. Cheng, et al. 1998. The structural basis of estrogen receptor/coactivator recognition and the antagonism of this interaction by tamoxifen. *Cell.* 95:927–37.

Shigekawa, K., and W. J. Dower. 1988. Electroporation of eukaryotes and prokaryotes: A general approach to the introduction of macomolecules into cells. *BioTechniques.* 6:742–751.

Shillito, R. 1999. Methods of genetic transformations: Electroporation and polyethylene glycol treatment. In Molecular improvement of cereal crop. I. Vasil, editor. Kluwer, Dordrecht, The Netherlands. 9–20.

Simonsen, C. C., and A. D. Levinson. 1983. Isolation and expression of an altered mouse dlhydrofolate reductase cDNA. *Proc. Natl. Acad. Sci. USA.* 80:2495–2499.

Southern, P. J., and P. Berg. 1982. Transformation of mammalian cells to antibiotic resistanced with a bacterial gene under control of the SV40 early region promoter. *J. Mol. Appl. Gen.* 1:327–341.

Spencer, D. M., T. J. Wandless, S. L. Schreiber, and G. R. Crabtree. 1993. Controlling signal transduction with synthetic ligands. *Science.* 262:1019–24.

Stein, C. A., and J. S. Cohen. 1988. Oligodeoxynucleotides as inhibitors of gene expression: a review. *Cancer Res.* 48:2659–68.

Thomas, K. R., and M. R. Capecchl. 1987. Site-directed mutagenesis by gene targeting in mouse embryo-derived stem cells. *Cell.* 51:503–12.

Thompson, J. A., and e. al. 1995. Maize transformation utilizing silicon carbide whiskers: A review. *Euphytica.* 85:75–80.

Touraev, A., and e. al. 1997. Plant male germ line transformation. *Plant J.* 12:949–956.

Trick, H. N., and e. al. 1997. Recent advances in soybean transformation. *Plant Tissue Cult. Biotechnol.* 3:9–26.

Triezenberg, S. J., R. C. Kingsbury, and S. L. McKnight. 1988. Functional dissection of VP16, the trans-activator of herpes simplex virus immediate early gene expression. *Genes Dev.* 2:718–29.

Turner, D. L., E. Y. Snyder, and C. L. Cepko. 1990. Lineage-independent determination of cell type in the embryonic mouse retina. *Neuron.* 4:833–845.

van der Krol, A. R., J. N. Mol, and A. R. Stuitje. 1988b. Modulation of eukaryotic gene expression by complementary RNA or DNA sequences. *Biotechniques.* 6:958–76.

van der Krol, A. R., J. N. Mol, and A. R. Stuitje. 1988a. Modulation of eukaryotic gene expression by complementary RNA or DNA sequences. *Biotechniques.* 6:958–76.

Wagner, T. E., and P. C. Hoppe. U.S. Pat. No. 4,873,191. 1989. Genetic transformation of zygotes.

Wang, Y., B. W. O'Malley, Jr., S. Y. Tsai, and B. W. O'Malley. 1994. A regulatory system for use in gene transfer. *Proc Natl Acad Sci USA.* 91:8180–4.

Webb, P., G. N. Lopez, R. M. Ulit, and P. J. Kushiner. 1995. Tamoxifen activation of the estrogen receptor/AP-1 pathway: potential origin for the cell-specific estrogen-like effects of antiestrogens. *Mol Endocrinol.* 9:443–56.

Webb, P., P. Nguyen, C. Valentine, R. V. Weatherman, et al. 2000. An antiestrogen-responsive estrogen receptor-alpha mutant (D351Y) shows weak AF-2 activity in the presence of tamoxifen. *J Biol Chem.* 275:37552–8.

Wells, J. A., M. Vasser, and D. B. Powers. 1985. Cassette mutagenesis: an efficient method for generation of multiple mutations at defined sites.*Gene.* 34:315–23.

Whitt, M. A., L. Buonocore, J. K. Rose, V. Ciccarone, et al. 1990. TransfectACE reagent promotes transient transfection frequencies greater than 90%. *Focus.* 13:8–12.

Wigler, M., A . Pellicer, S. Silversittein, and R. Axel . 1978. Biochemical transfer of single-copy eucaryotic genes using total cellular DNA as donor. *Cell.* 14:725.

Williams, D. A., I. R. Lemischka, D. G. Nathan, and R. C. Mulligan. 1984. Introduction of a new genetic material into pluripotent haematopoietic stem cells of the mouse. *Nature.* 310:476–480.

Wilmut, I., A. E. Schnieke, J. McWhir, A. J. Kind, et al. 1997. Viable offspring derived from fetal and adult mammalian cells. *Nature.* 385:810–3.

Wong, T. K., and E. Neumann. 1982. Electric field mediated gene transfer. *Biochemical and Biophysical Research Communications.* 107:584–587.

Zhang, C. C., S. Krieg, and D. J. Shapiro. 1999. HMG-1 stimulates estrogen response element binding by estrogen receptor from stably transfected HeLa cells. *Mol Endocrinol.* 13:632–43.

Zhang, Y., C. Riesterer, A. M. Ayrall, F. Sablitzky, et al. 1996. Inducible site-directed recombination in 1 0 mouse embryonic stem cells. *Nucleic Acids Res.* 24:543–8.

Zhou, G., and e. al. 1983. Introduction of exogenous DNA into cotton embryos. *Methods Enzymol.* 101:433–481.

Zoller, M. J., and M. Smith. 1987. Oligonucleotide-directed mutagenesis: a simple method using two oligonucleotide primers and a single-stranded DNA template. *Methods Enzymol.* 154:329–50.

Zon, G. 1988. Oligonucleotide analogues as potential chemotherapeutic agents. *Pharm Res.* 5:539–49.

Zuo, J., and N. H. Chua. 2000. Chemical-inducible systems for regulated expression of plant genes. *Curr Opin Biotechnol.* 11: 146–51.

The invention claimed is:

1. An isolated polynucleotide, comprising:
   a first polynucleotide; and
   a second polynucleotide operably linked to the first polynucleotide;
   wherein when the first polynucleotide is inserted into a promoter region of a gene, enhances transcription of the gene, when the first polynucleotide is bound by a mutant estrogen receptor to which is bound 4-hydroxytamoxifen,
   the first polynucleotide comprises nucleotides 2–6 and 10–14 of SEQ ID NO:75, and
   the mutant estrogen receptor has the amino acid sequence of SEQ ID NO:4.

2. The polynucleotide of claim 1, wherein the first polynucleotide comprises a nucleic acid sequence selected from the group consisting of SEQ ID NOS:75, 78, 80 and 82.

3. A vector, comprising the polynucleotide of claim 2.

4. An isolated or cultured cell, comprising the polynucleotide of claim 2.

5. The polynucleotide of claim 1, wherein the second polynucleotide comprises a nucleic acid sequence encoding a polypeptide selected from the group consisting of SEQ ID NOS:4, 6, 8, 10, 12, 14, 16, 18, 20, 22, 24, 66, 68, 70 and 72.

6. The polynucleotide of claim 5, wherein the first polynucleotide comprises a nucleic acid sequence selected from the group consisting of SEQ ID NOS:75, 78, 80 and 82.

7. A vector, comprising the polynucleotide of claim 6.

8. An isolated or cultured cell, comprising the polynucleotide of claim 6.

9. A vector, comprising the polynucleotide of claim 5.

10. An isolated or cultured cell, comprising the polynucleotide of claim 5.

11. The polynucleotide of claim 1, wherein the second polynucleotide encodes a therapeutic polypeptide or an antibody.

12. A vector, comprising the polynucleotide of claim 11.

13. An isolated or cultured cell, comprising the polynucleotide of claim 11.

14. The polynucleotide of claim 11, wherein the first polynucleotide comprises a nucleic acid sequence selected from the group consisting of SEQ ID NOS:75, 78, 80 and 82.

15. A vector, comprising the polynucleotide of claim 14.

16. An isolated or cultured cell, comprising the polynucleotide of claim 14.

17. The polynucleotide of claim 11, wherein the second polynucleotide comprises a nucleic acid sequence encoding a polypeptide selected from the group consisting of SEQ ID NOS:4, 6, 8, 10, 12, 14, 16, 18, 20, 22, 24, 66, 68, 70 and 72.

18. A vector, comprising the polynucleotide of claim 17.

19. An isolated or cultured cell, comprising the polynucleotide of claim 17.

20. The polynucleotide of claim 1, wherein the second polynucleotide is an antisense polynucleotide.

21. A vector, comprising the polynucleotide of claim 20.

22. An isolated or cultured cell, comprising the polynucleotide of claim 20.

23. The polynucleotide of claim 20, wherein the first polynucleotide comprises a nucleic acid sequence selected from the group consisting of SEQ ID NOS:75, 78, 80 and 82.

24. A vector, comprising the polynucleotide of claim 23.

25. An isolated or cultured cell, comprising the polynucleotide of claim 23.

26. The polynucleotide of claim 20, wherein the second polynucleotide comprises a nucleic acid sequence encoding a polypeptide selected from the group consisting of SEQ ID NOS:4, 6, 8, 10, 12, 14, 16, 18, 20, 22, 24, 66, 68, 70 and 72.

27. A vector, comprising the polynucleotide of claim 26.

28. An isolated or cultured cell, comprising the polynucleotide of claim 26.

29. A vector, comprising the polynucleotide of claim 1.

30. An isolated or cultured cell, comprising the polynucleotide of claim 1.

* * * * *